US011993646B2

United States Patent
Hyde et al.

(10) Patent No.: US 11,993,646 B2
(45) Date of Patent: *May 28, 2024

(54) COMPOSITIONS AND METHODS FOR MODIFIED B CELLS EXPRESSING REASSIGNED BIOLOGICAL AGENTS

(71) Applicant: KOTA BIOTHERAPEUTICS, LLC, Bellevue, WA (US)

(72) Inventors: Roderick A. Hyde, Redmond, WA (US); Wayne R. Kindsvogel, Seattle, WA (US); Gary L. McKnight, Bothell, WA (US)

(73) Assignee: KOTA BIOTHERAPEUTICS, LLC, Bellevue, WA (US)

(*) Notice: Subject to any disclaimer, the term of this patent is extended or adjusted under 35 U.S.C. 154(b) by 742 days.

This patent is subject to a terminal disclaimer.

(21) Appl. No.: 16/994,837

(22) Filed: Aug. 17, 2020

(65) Prior Publication Data

US 2021/0095010 A1    Apr. 1, 2021

Related U.S. Application Data

(63) Continuation of application No. 15/924,898, filed on Mar. 19, 2018, now Pat. No. 10,745,468, which is a continuation-in-part of application No. 15/178,715, filed on Jun. 10, 2016, now Pat. No. 10,233,424, which is a continuation-in-part of application No. 14/549,685, filed on Nov. 21, 2014, now Pat. No. 9,512,213, which is a continuation of application No. 13/374,351, filed on Dec. 22, 2011, now Pat. No. 9,175,072.

(51) Int. Cl.
| | |
|---|---|
| C12N 5/10 | (2006.01) |
| A61K 39/00 | (2006.01) |
| C07K 16/00 | (2006.01) |
| C07K 16/10 | (2006.01) |
| C07K 16/12 | (2006.01) |
| C07K 16/18 | (2006.01) |
| C07K 16/30 | (2006.01) |
| C07K 16/44 | (2006.01) |
| C12N 5/0781 | (2010.01) |
| G01N 33/68 | (2006.01) |

(52) U.S. Cl.
CPC ............ *C07K 16/18* (2013.01); *A61K 39/00* (2013.01); *C07K 16/00* (2013.01); *C07K 16/1018* (2013.01); *C07K 16/109* (2013.01); *C07K 16/1271* (2013.01); *C07K 16/3069* (2013.01); *C07K 16/44* (2013.01); *C12N 5/0635* (2013.01); *G01N 33/6854* (2013.01); *A61K 2039/505* (2013.01); *A61K 2039/5156* (2013.01); *C07K 2317/14* (2013.01); *C07K 2317/33* (2013.01); *C07K 2317/76* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 5,087,557 | A | 2/1992 | McClure |
| 5,202,238 | A | 4/1993 | Fell, Jr. et al. |
| 5,997,859 | A | 12/1999 | Barber et al. |
| 6,570,061 | B1 | 5/2003 | Rajewsky et al. |
| 6,576,464 | B2 | 6/2003 | Gold et al. |
| 6,841,383 | B2 | 1/2005 | Reff et al. |
| 7,015,034 | B2 | 3/2006 | Lawman et al. |
| 7,166,704 | B2 | 1/2007 | Batra et al. |
| 7,262,028 | B2 | 8/2007 | Van Berkel et al. |
| 7,378,276 | B2 | 5/2008 | Ettinger et al. |
| 7,429,486 | B2 | 9/2008 | Van Berkel et al. |
| 7,629,171 | B2 | 12/2009 | Meagher et al. |
| 7,741,077 | B2 | 6/2010 | Grawunder et al. |
| 7,875,280 | B2 | 1/2011 | Schneewind et al. |
| 7,927,834 | B2 | 4/2011 | Van Berkel et al. |
| 7,939,059 | B2 | 5/2011 | Yang et al. |
| 7,993,864 | B2 | 8/2011 | Brown et al. |
| 8,013,128 | B2 | 9/2011 | Gudas et al. |
| 8,101,181 | B2 | 1/2012 | Ruben et al. |

(Continued)

FOREIGN PATENT DOCUMENTS

| | | |
|---|---|---|
| CN | 1227607 A | 9/1999 |
| CN | 1468123 A | 1/2004 |

(Continued)

OTHER PUBLICATIONS

Milone et al.; "Chimeric Receptors Containing CD137 Signal Transduction Domains Mediate Enhanced Survival of T Cells and Increased Antileukemic Efficacy In Vivo"; Molecular Therapy; Aug. 2009; pp. 1453-1464; vol. 17, No. 8; The American Society of Gene & Cell Therapy.

Yu et al.; "Human mb-1 Gene: Complete cDNA Sequence and Its Expression in B Cells Bearing Membrane Ig of Various Isotypes"; The Journal of Immunology; bearing a date of Jan. 15, 1992; pp. 633-637; vol. 148, No. 2; The American Association of Immunologists; Printed in U.S.A.

Xia, Y., et al., "IL-2 augments the therapeutic efficacy of adoptively transferred B cells which directly kill tumor cells . . . " Oncotarget 7(37):60461-60474, Aug. 9, 2016.

(Continued)

*Primary Examiner* — Michail A Belyavskyi
(74) *Attorney, Agent, or Firm* — AEON Law, PLLC; Adam L. K. Philipp; Ki Yong O

(57) ABSTRACT

Compositions and methods are disclosed herein for producing one or more immunoglobulins in an isolated cytotoxic B lymphocyte cell line. An isolated cell line includes an isolated B lymphocyte cell line capable of expressing at least one exogenously incorporated membrane immunoglobulin capable of binding to a first antigen and at least one endogenous secreted immunoglobulin capable of binding to a second antigen, and further capable of expressing at least one exogenously incorporated recombinant B cell receptor that signals for expression of cytotoxic effector molecules.

23 Claims, 16 Drawing Sheets

(56) References Cited

U.S. PATENT DOCUMENTS

| | | |
|---|---|---|
| 9,175,072 B2 | 11/2015 | Hyde et al. |
| 2005/0170398 A1 | 8/2005 | Van Berkel et al. |
| 2005/0208120 A1 | 9/2005 | Salvatore |
| 2007/0071717 A1 | 3/2007 | Weiner et al. |
| 2007/0116690 A1 | 5/2007 | Yang et al. |
| 2010/0261180 A1 | 10/2010 | Trapani et al. |
| 2011/0177073 A1 | 7/2011 | Van Berkel et al. |
| 2013/0154277 A1 | 6/2013 | Willems |
| 2013/0164277 A1 | 6/2013 | Hyde et al. |
| 2013/0164784 A1 | 6/2013 | Hyde et al. |
| 2015/0203572 A1 | 7/2015 | Hyde et al. |
| 2015/0225470 A1 | 8/2015 | Zhang et al. |
| 2015/0283177 A1 | 10/2015 | Hyde et al. |
| 2016/0355783 A1 | 12/2016 | Hyde et al. |
| 2017/0173180 A1 | 6/2017 | Li |
| 2018/0215817 A1 | 8/2018 | Hyde et al. |

FOREIGN PATENT DOCUMENTS

| | | |
|---|---|---|
| WO | 2006136008 A1 | 12/2006 |
| WO | 2010070263 A1 | 6/2010 |
| WO | WO-2010070263 | 6/2010 |
| WO | WO-2011050985 | 5/2011 |
| WO | 2013096568 A1 | 6/2013 |
| WO | WO2013-096568 | 6/2013 |
| WO | 2017214376 A1 | 12/2017 |

OTHER PUBLICATIONS

Xu, H., et al., "Development and Characterization of Anti-Gal B Cell Receptor Transgenic Gal-/-Mice," Transplantation 73(10):1549-1557, May 27, 2002.

Xu, Y., et al., "No receptor stands alone: IgG B-cell receptor intrinsic and extrinsic mechanisms contribute to antibody memory," Cell Research 24:651-664, May 20, 2014.

Zhang, G., et al., "Supression of human prostate tumor growth by a unique prostate-specific monoclonal antibody F77 . . . " PNAS USA, 107(2):732-737, Jan. 12, 2010.

Zheng, Q., et al., "Precise gene deletion and replacement using the CRISPR/Cas9 system in human cells," BioTechniques 57(3):115-124, Sep. 2014.

Zimmerman, U., et al., "Electromanipulation of Mammalian Cells: Fundamentals and Application," IEEE Transactions on Plasma Science 28(1):72-82, Feb. 2000.

Kwakkenbos, M.J., et al., "Generation of stable monoclonal antibody-producing BCR+ human memory B cells by genetic programming," Nature Medicine 16(1):123-128, Jan. 2010.

Li, Q., et al., "Adoptive Transfer of Tumor Reactive B Cells Confers Host T-Cell Immunity and Tumor Regression," Clinical Cancer Research 17(15):1-9, 2011.

Li, Q., et al., "In Vivo Sensitized and In Vitro Activated B Cells Mediate Tumor Regression in Cancer . . . " Journal of Immunology 183:3195-3203, Aug. 10, 2009.

PCT International Search Report; International App. No. PCT/US2012/070840; dated Apr. 29, 2013; pp. 1-3; and Search History (4 pages).

Casucci, M., and Bondanza, A., "Suicide Gene Therapy to Increase the Safety of Chimeric Antigen Receptor-Redirected T Lymphocytes," Journal of Cancer 2:378-382, Jul. 1, 2011.

Corti, D., et al., "A Neutralizing Antibody Selected from Plasma Cells That Binds to Group 1 and Group 2 Influenza A Hemagglutinins," Science 333:850-856, Aug. 12, 2011.

Corti, D., et al., "Heterosubtypic neutralizing antibodies are produced by individuals immunized . . . " Journal of Clinical Investigation 120(5):1663-1673, May 2010.

Croft, M., et al., "The Significance of OX40 and OX40L to T cell Biology and Immune Disease," Immunology Review 229(1):173-191, May 2009.

Cruz-Guilloty, F., et al., "Runx3 and T-box proteins cooperate to establish the transcriptional program of effector CTLs," J Experimental Medicine 206(1):51-59, Jan. 12, 2009.

DNP-KLH (Keyhole Limpet Hemocyanin), Product Information Sheets, BTI Catalog #: D-5060, pp. 1-2, Biosearch Technologies, Inc., Novato, California, © 2005.

Durand, J., et al., "Regulatory B Cells with a Partial Defect in CD40 Signaling and Overexpressing Granzyme B . . . " Journal of Immunology 1195:5035-5044, Oct. 2, 2015.

Early kinetic screening of hybridomas for confident antibody selection using Biacore . . . Prod. Info. Sht., pp. 1-8, Biacore Sys, App Note 84, GE Healthcare, Uppsala, SE May 2007.

Early, P.W., et al., "Immunoglobulin heavy chain gene organization in mice: Analysis of a myeloma genomic clone . . . " Pnas USA Genetics, 76(2):857-861 Feb. 1979.

Ekiert, D.C., et al., "Antibody Recognition of a Highly Conserved Influenza Virus Epitope," Science 324:246-251, Apr. 10, 2009.

European Supplementary Search Report for EP Patent Application No. 19771532.9 dated Jan. 5, 2022, 7 pages.

Le Cong, et al., "Multiplex Genome Engineering Using CRISPR/Cas Systems," Science 339 (6121): 819-823, Feb. 15, 2013. (abstract).

Lorenz, U., et al., "Functional Antibodies Targeting IsaA of *Staphylococcus aureus* Augment Host Immune Response . . . " Antimicrobial Agents and Chemotherapy 55(1):165-173 Jan. 2011.

Lund, F.E., "Cytokine-producing B lymphocytes—key regulators of immunity," Current Opinion Immunology 20(3):332-338, Jun. 2008.

Okada, T., et al., "Chemokine Requirements for B Cell Entry to Lymph Nodes and Peyer's Patches," Journal of Experimental Medicine 196(1):65-75, Jul. 1, 2002.

Pansri, P., et al., "A compact phage display human scFv library for selection of antibodies to a wide variety of antigens," BMC Biotechnology 9(6):1-16, Jan. 29, 2009.

Parrish-Novak, J., et al., "Interleukin-21 and the IL-21 receptor: novel effectors of NK and T cell responses," Journal of Leukocyte Biology 72:856-863, Nov. 2002.

Price, P.W., et al., "Engineered cell surface expression of membrane immunoglobulin as a means to identify . . . " Journal of Immunological Methods 343:28-41, 2009.

Rentenaar, R.J., et al., "Immune responsiveness in renal transplant recipients: Mycophenolic acid severely depresses humoral immunity . . . " Kidney International 62:319-328, 2002.

Sackstein, R., et al., "T-lymphocyte homing: an underappreciated yet critical hurdle for successful cancer . . . " Laboratory Investigation 97:669-697 USCAP, Inc., Mar. 27, 2017.

Schmidt, C., et al., "Signaling of the BCR is regulated by a lipid rafts-localised transcription factor, Bright," The EMBO Journal 28:711-724, Feb. 12, 2009.

Schneider, C., et al., "A One-step Purification of Membrane Proteins Using a High Efficiency . . . " Journal of Biological Chemistry 257(18)10766-10769, Sep. 25, 1982.

Shi, N., et al., "Interaction Between The Gut Microbiome and Mucosal Immune System," Military Medical Research 4(14):1-7, 2017.

Sorenmo K.U., et al., "CD40-Activated B Cell Cancer Vaccine Improves Second Clinical Remission and Survival in Privately Owned Dogs . . . " PLoS One 6(88):1-8, Aug. 31, 2011.

Suk, E-K., et al., "A comprehensively molecular haplotype-resolved genome . . . " Genome Research, pp. 1-14, Cold Spring Harbor Laboratory Press, Aug. 3, 2011.

Takacs, K., et al., "The regulated long-term delivery of therapeutic proteins by using antigen-specific" PNAS USA 1101(46):16298-101(46):16298-16303, Nov. 16, 2004.

Tangye, S.G., and Good, K.L., "Human IgM+CD27+ B Cells: Memory B Cells or "Memory" B Cells?" The Journal of Immunology 179:13-19, May 14, 2007.

Tiller, T., et al., "Efficient generation of monoclonal antibodies from single human B cells by single cell . . . " Journal of Immunological Methods 329(1-2):112-124 Jan. 2008.

Tyler, B.M., et al., "mRNA for surface immunoglobulin chains encodes a highly conserved transmembrane sequence . . . " PNAS USA 79:2008-2012, Mar. 1982.

Visintin, M., et al., "Selection of antibodies for intracellular function using a two-hybrid in vivo system," PNAS USA 96(21):11723-11728, Oct. 12, 1999.

(56) References Cited

OTHER PUBLICATIONS

Wrammert, J., et al., Rapid Cloning of High Affinity Human Monoclonal Antibodies Against Influenza Virus, Nature 453(7195):667-671, May 29, 2008.
Biosearch Technologies; DNP-KLH (Keyhole Limpet Hemocyanin); Production Information; pp. 1-2; bearing a date of 2005.
European Patent Office, Supplementa,y European Search Report, Pursuant to Rule 62 EPC; App. No. EP •12859056; dated Apr. 10, 2015 (received by our Agent on Apr. 17, 2015); pp. 1-6.
Vettermann, C., et al., "Allelic exclusion of immunoglobulin genes: models and mechanisms," Immunological Reviews 237(1):22-42, Sep. 19, 2010.
Wienands, J., and Engels, N., "The Memory Function of the B Cell . . . " B Cell Receptor Signaling 393:107-121, pt Current Topics in Microbi and Immuno (vol. 393) Sep. 12, 2015.
Molecular Cloning: A Laboratory Manual, 2nd Ed., J.F. Sambrook and D.W. Russell, eds., Cold Spring Harbor Press, Cold Spring Harbor, N.Y., 1989.
Cerutti, A., et al., "Engagement of CD153 (CD30 Ligand) by CD30+ T Cells Inhibits Class Switch DNA Recombination and Antibody . . . " Journal of Innuno. 165(2):786794 Jul. 1, 2000.
Electroporation Guide, Bulletin 5700, Rev. A, BioRad, Inc., Hercules, CA.
Extended European Search Report, pursuant to Rule 62 EPC for App. No. EP 17811004.5, dated Dec. 20, 2019 (received by our Agent on Dec. 30, 2019), EPO pp. 1-7.
Abbas, A.K., et al., "Cellular and Molecular Immunology: with Student Consult Online Access," 7th Ed, pp. 1-8, Elsivier Saunders, Philadelphia, PA, May 9, 2011.
Amaxa® Human B Cell Nucleofector®Kit, Product Information Sheet, pp. 1-4, Lonza Cologne AG, Cologne, Germany, © 2009.
Arimoto-Miyamoto, K., et al., "Optimal stimulation for CD70 induction on human monocyte-derived dendritic cells . . . " Immunology 130:137-149, Nov. 18, 2009.
Balazs, A.B., et al., "Antibody-based protection against HIV infection by vectored immunoprophylaxis," Nature 481(7379):81-84, Macmillan Publishers Limited, Nov. 30, 2011.
Bensinger, W., et al., "Autologous transplantation with peripheral blood mononuclear cells . . . " Blood 81(11):3158-3163, Jun. 1, 1993.
Bhatt, A.P., et al., "The Role of the Microbiome in Cancer Development and Therapy," CA Cancer Journal Clin 67(4):326-344, Jul./Aug. 2017.
Bovia, F., et al., "Efficient transduction of primary human B lymphocytes and nondividing myeloma B cells . . . " Blood 101(5):1727-1733, Mar. 1, 2003.
Bueno, C., et al., "Reprogramming human B cells into induced pluripotent stem cells and its enhancement . . . " Leukemia, pp. 1-9, Macmillan Publishers Limited, Nov. 27, 2015.
Cabinian, A., et al., "Transfer of Maternal Immune Cells by Breastfeeding: Maternal Cytotoxic T Lymphocytes Present in Breast Milk . . . " PLoS One 11(6):e0156762, Jun. 10, 2016.
Casey, K.A., and Mescher, M.F., "IL-21 Promotes Differentiation of Naïve CD8 T Cells to a Unique Effector Phenotype," Journal of Immunology 178:7640-7648, Mar. 7, 2007.
Extended European Search report dated Apr. 15, 2017, for European App. No. 12859056.9 (PCT/US2012/070840), EPO.
Eyquem, J., et al., "Targeting a CAR to the TRAC locus with CRISPR/Cas9 Enhances Tumour Rejection," Nature, 543(7643):113-117, Mar. 2017.
Farra, R., et al., "First-in-Human Testing of a Wirelessly Controlled Drug Delivery Microchip," Science Translational Medicine 4(122):1-12, Feb. 22, 2012.
Hagn, M., and Jahrsdörfer, B., "Why do human B cells secrete granzyme B? Insights into a novel B-cell differentiation pathway," OncoImmunology 1(8):1368-1375, Sep. 9, 2015.
Hagn, M., et al., "Human B cells differentiate into granzyme B-secreting cytotoxic B . . . " Immunology and Cell Biology 90:457-467, Australasian Soc for Immunology, Aug. 2, 2012.
International Search Report dated Jun. 26, 2019, for PCT/US2019/022572, filed Mar. 15, 2019, pp. 1-8.
Kalos, M., et al., "Supplementary Materials for T Cells with Chimeric Antigen Receptors Have Potent Antitumor Effects . . . " Sci Transl Med 3:1-25, Aug. 2011.
Kelly-Quintos, C., et al., "Characterization of the Opsonic and Protective Activity against *Staphylococcus* . . . " Infection and Immunity 74(5):2742-2750, May 2006.
Khurana, S., et al., "Antigenic fingerprinting of H5N1 Avian Influenza Using Convalescent Sera and Monoclonal Antibodies Reveals . . . " PLoS One 6(4):1-8, Apr. 29, 2011.
Kim, J.H., et al., "High Cleavage Efficiency of a 2A Peptide Derived from Porcine Teschovirus-1 in Human Cell Lines, Zebrafish and Mice," PLoS One 6(4):1-8, Apr. 29, 2011.

Secreted and Membrane γ-H Chain Gene with Alternate Polyadenylation Sites

Maternal Chromosome 14 Membrane γ-H Chain Gene

Paternal Chromosome 14 with Secreted γ-H Chain Gene

Integration of Anti-PCLA Single Chain Antibody Gene at Rearranged Kappa Light Chain Locus Rearranged Kappa Light Chain Gene Integration of the CXCR3 Gene at the Rearranged Ig Heavy-Chain Locus Rearranged IgM (Mu) Heavy Chain Gene Integration of the Human IL-10 Gene at the Rearranged Ig H-Chain Locus Expression Vector for Anti-MOG Membrane IgG Antibody Disruption and replacement of gamma H-chain gene AAV vector with Bicistronic Construct Edited Gamma H-chain Gene with Bicistronic Construct

COMPOSITIONS AND METHODS FOR MODIFIED B CELLS EXPRESSING REASSIGNED BIOLOGICAL AGENTS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

The present application constitutes a continuation of U.S. patent application Ser. No. 15/924,898, now U.S. Pat. No. 10,745,468, titled COMPOSITIONS AND METHODS FOR MODIFIED B CELLS EXPRESSING REASSIGNED BIOLOGICAL AGENTS, naming Roderick A. Hyde, Wayne R. Kindsvogel, and Gary L. McKnight as inventors, filed Mar. 19, 2018, which is a continuation-in-part of U.S. patent application Ser. No. 15/178,715, now U.S. Pat. No. 10,233,424, titled COMPOSITIONS AND METHODS INCLUDING CYTOTOXIC B LYMPHOCYTE CELL LINE EXPRESSING EXOGENOUS MEMBRANE IMMUNOGLOBULIN DIFFERENT FROM SECRETED IMMUNOGLOBULIN, naming Roderick A. Hyde, Wayne R. Kindsvogel, and Gary L. McKnight as inventors, filed Jun. 10, 2016, which is a continuation-in-part of U.S. patent application Ser. No. 14/549,685, now U.S. Pat. No. 9,512,213, titled COMPOSITIONS AND METHODS INCLUDING RECOMBINANT B LYMPHOCYTE CELL LINE INCLUDING AN EXOGENOUSLY INCORPORATED NUCLEIC ACID EXPRESSING AN EXOGENOUS MEMBRANE IMMUNOGLOBULIN REACTIVE TO A FIRST ANTIGEN AND INCLUDING AN ENDOGENOUS GENE EXPRESSING AN ENDOGENOUS SECRETED IMMUNOGLOBULIN REACTIVE TO A SECOND ANTIGEN, naming Roderick A. Hyde and Wayne R. Kindsvogel as inventors, filed Nov. 21, 2014, which is a continuation of U.S. patent application Ser. No. 13/374,351, now U.S. Pat. No. 9,175,072, titled COMPOSITIONS AND METHODS INCLUDING RECOMBINANT B LYMPHOCYTE CELL LINE INCLUDING AN EXOGENOUSLY INCORPORATED NUCLEIC ACID EXPRESSING AN EXOGENOUS MEMBRANE IMMUNOGLOBULIN REACTIVE TO A FIRST ANTIGEN AND INCLUDING AN ENDOGENOUS GENE EXPRESSING AN ENDOGENOUS SECRETED IMMUNOGLOBULIN REACTIVE TO A SECOND ANTIGEN, naming Roderick A. Hyde and Wayne R. Kindsvogel as inventors, filed Dec. 22, 2011.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

Compositions and methods are disclosed herein for producing an immunoglobulin in a recombinant B lymphocyte cell line. Compositions and methods are disclosed herein for treating a disease in a vertebrate subject with an immunotherapeutic product. The immunotherapeutic product can include the recombinant B lymphocyte cell line that produces one or more antibodies. The immunotherapeutic product can include the recombinant B lymphocyte cell line that is an exceptional antigen presenting cell.

Compositions and methods are disclosed for providing a therapeutically effective amount of one or more modified B lymphocytes to a patient suspected or known to have a disease, disorder, or condition of the immune system including, but not limited to, infectious disease, auto-immune disease, cancer, neuro-physiological disease or disorders, or other pathological conditions. In an embodiment, a cohort of modified B lymphocytes is provided, as described herein. In an embodiment, a monoclonal administration of modified B lymphocytes is provided, as described herein. In an embodiment, a polyclonal administration of modified B lymphocytes is provided, as described herein.

Compositions and methods are disclosed herein for producing one or more immunoglobulins in an isolated modified B cell that may be part of a B lymphocyte cell line. Compositions and methods are disclosed herein for producing one or more immunoglobulins in the isolated modified B cell or B lymphocyte cell line that direct cell signaling by membrane immunoglobulin in the isolated modified B cell or B lymphocyte cell line. Immune cell therapy in a vertebrate subject can include administering to the vertebrate subject the isolated modified B cell or B lymphocyte cell line that synthesizes secreted immunoglobulins and membrane immunoglobulins each having different target antigens. Immune cell therapy in a vertebrate subject can include administering to the vertebrate subject antigen presenting cells comprised of the isolated modified B cell or B lymphocyte cell line that direct antigen internalization and processing to produce exceptional antigen presenting cells. The isolated modified B cell or B lymphocyte cell line can produce antigen presenting cells that are exceptional or superior at capturing, internalizing and presenting the antigen recognized by the endogenous or exogenously derived membrane immunoglobulin. Compositions and methods are disclosed herein for treating a disease in a vertebrate subject with an immunotherapeutic product. The immunotherapeutic product can include the isolated modified B cell or B lymphocyte cell line having an endogenously-derived or exogenously derived membrane immunoglobulin reactive to a first antigen (e.g., capable of binding to a first antigen) wherein the isolated modified B cell or B lymphocyte cell line produces one or more secreted immunoglobulins reactive to a second antigen or produces a reassigned biological agent. The immunotherapeutic product can include the isolated modified B cell or B lymphocyte cell line that can be a monoclonal B lymphocyte cell line or polyclonal B lymphocyte cell line that produces one or more secreted immunoglobulins. The immunotherapeutic product can include the isolated B lymphocyte cell line that produces one or more secreted antibodies, e.g., antibodies that recognize different epitopes on the same antigen. The immunotherapeutic product can include the isolated B lymphocyte cell line that produces reassigned biological agents (e.g., cytokines, cytotoxins, chemokines, receptors, ligands, immunomodulatory, immune effector molecules, transcription factors, etc.). The immunotherapeutic product can include the isolated B lymphocyte cell line as one or more antigen presenting cells.

Thus, the reassigned biological agent can include an agent (such as a cytokine or ligand) that is typically not expressed by naturally occurring B lymphocytes, or is not expressed under certain circumstances or conditions by naturally occurring B lymphocytes. Our modified B lymphocytes are able to express the reassigned biological agent due to the engineering of that B lymphocyte, which may include constitutive expression of the reassigned biological agent, or may include inductive expression under specific circumstances or conditions (for example, "triggering" of expression by receptor/ligand binding on the surface of the modified B lymphocyte).

The isolated B lymphocyte cell line can include an immunotherapeutic product administered to a vertebrate subject to develop long-lived isolated B lymphocytes in the vertebrate subject for immune surveillance of chronic disease. The immunotherapeutic product can include the isolated B lymphocyte cell line having a reassigned biological agent to modulate immunity for therapy of chronic or acute disease (for example, IL-10 for multiple sclerosis or IL-2 for influenza). The immunotherapeutic product can include the isolated B lymphocyte cell line having an endogenously-derived or exogenously derived membrane immunoglobulin that can be administered to a vertebrate subject to provide an antigen presenting cell to the vertebrate subject.

In an embodiment, an isolated modified B cell includes at least one reassigned biological agent incorporated at an active Ig gene location (e.g., H or L chain) in a memory B cell. In an embodiment, the reassigned biological agent is under the control of the Ig promoter/enhancer elements and the endogenous antibody (secreted and/or membrane) of the isolated modified B cell is disrupted. In an embodiment, the isolated modified B cell has an exogenous membrane Ig (B cell receptor) that binds to an antigen and induces expression of the reassigned biological agent. In an embodiment, the exogenous membrane Ig (B cell receptor) and reassigned biological agent can both be expressed at the same active Ig locus (e.g., H chain).

An isolated cell line as described herein can include an isolated B lymphocyte cell line capable of expressing at least one exogenously incorporated membrane immunoglobulin reactive to a first antigen and at least one endogenous secreted immunoglobulin reactive to a second antigen. The isolated B lymphocyte cell line is capable of expressing at least one endogenous membrane immunoglobulin reactive to the second antigen. The at least one exogenously incorporated membrane immunoglobulin can include one or more exogenously incorporated membrane immunoglobulin polypeptides. The at least one exogenously incorporated membrane immunoglobulin can include at least one exogenously incorporated nucleic acid encoding the at least one membrane immunoglobulin, wherein the cell line is capable of expressing the at least one membrane immunoglobulin. The at least one exogenously incorporated membrane immunoglobulin comprises at least two exogenously incorporated nucleic acid encoding the at least one membrane immunoglobulin. The at least one exogenously incorporated membrane immunoglobulin can include nucleic acids encoding two heavy chain (H) immunoglobulins and two light chain (L) immunoglobulins. The at least one exogenously incorporated membrane immunoglobulin can include nucleic acids encoding one heavy chain (H) immunoglobulin and one light chain (L) immunoglobulin. The at least one exogenously incorporated membrane immunoglobulin can include nucleic acids encoding one single chain Fv (SCFv) immunoglobulin (e.g., SCFv fused with immunoglobulin constant region domains). The exogenously incorporated nucleic acid encoding the at least one membrane immunoglobulin can be present in one or more chromosomal loci in the isolated B lymphocyte cell line. The exogenously incorporated nucleic acid in the isolated B lymphocyte cell line is capable of disrupting expression of the endogenous immunoglobulin. For example, disruption of endogenous H or L chain expression may knock out production of member IgG and/or secreted IgG and more generally may knock out endogenous antibody synthesis.

In an embodiment, inserting the exogenously incorporated membrane immunoglobulin, exogenously incorporated secreted immunoglobulin, or exogenously incorporated cytotoxicity effector molecule at an active site (e.g. using CRISPR technology as described herein) allows for a hijacking of the endogenous machinery (e.g., upon rearrangement of the regions, the promoter and enhancer elements are brought into close proximity).

The at least two exogenously incorporated nucleic acids encoding the at least one of the membrane immunoglobulin can be present in Ig H chain and Ig L chain chromosomal loci in the isolated B lymphocyte cell line. The at least one exogenously incorporated nucleic acid encoding the at least one membrane immunoglobulins can be present in one or more non-Ig L chain or non-Ig H chain chromosomal loci in the isolated B lymphocyte cell line. The at least one exogenously incorporated nucleic acid encoding the at least one membrane immunoglobulin can be present in an extrachromosomal replicating genetic element in the isolated B lymphocyte cell line. The at least one exogenously incorporated nucleic acid encoding the at least one membrane immunoglobulin can be derived from a B lymphocyte cell line. The at least one exogenously incorporated membrane immunoglobulin activated by the first antigen is capable of controlling expression of the at least one endogenous secreted immunoglobulin reactive to the second antigen. The isolated B lymphocyte cell line can include at least one of naïve B lymphocyte, immature B lymphocyte, transitional B lymphocyte, mature B lymphocyte, B1 B lymphocyte, marginal zone B lymphocyte, follicular B lymphocyte, memory B lymphocyte, plasmablast, or plasma cell. The isolated B lymphocyte cell line can include a polyclonal population of B lymphocytes. The isolated B lymphocyte cell line can include a monoclonal population of B lymphocytes. The membrane immunoglobulin can include at least one of a membrane anchor, a cytoplasmic domain, a hinge region and an extracellular ligand-binding domain.

In an embodiment, the exogenously incorporated nucleic acid encoding the at least one membrane immunoglobulin can be integrated into one or more locations along the genes encoding the B cell receptor. In an embodiment, the exogenously incorporated nucleic acid encoding the at least one membrane immunoglobulin can be integrated into one or more locations in the Ig loci (e.g., the heavy chain or light chain immunoglobulins as described above).

An isolated recombinant cell line as described herein can include an isolated B lymphocyte cell line capable of expressing at least one exogenously incorporated membrane immunoglobulin reactive to a first antigen and at least one exogenously incorporated nucleic acid encoding secreted immunoglobulin reactive to a second antigen. The isolated B lymphocyte cell line is capable of expressing at least one exogenously incorporated nucleic acid encoding membrane immunoglobulin reactive to the second antigen. The isolated B lymphocyte cell line is capable of expressing at least one exogenously incorporated nucleic acid encoding a secreted immunoglobulin reactive to a third antigen. The second antigen and the third antigen can be different epitopes of a single antigenic polypeptide. The at least one exogenously incorporated membrane immunoglobulin can include at least one exogenously incorporated membrane immunoglobulin polypeptide. The at least one exogenously incorporated membrane immunoglobulin can include at least one exogenously incorporated nucleic acid encoding at least one membrane immunoglobulin polypeptide, wherein the cell line is capable of expressing the at least one membrane immunoglobulin polypeptide. The at least one exogenously incorporated nucleic acid encoding the at least one membrane immunoglobulin can be present in one or more chromosomal loci in the isolated B lymphocyte cell line. The at least two exogenously incorporated nucleic acids encoding the at least one membrane immunoglobulins can be present in Ig H chain and Ig L chain chromosomal loci in the isolated B lymphocyte cell line. The at least one exogenously incorporated nucleic acids encoding the at least one membrane immunoglobulin can be present in one or more non-Ig L or non-Ig H chromosomal loci in the isolated B lymphocyte cell line. The at least one exogenously incorporated nucleic acids encoding the at least one membrane immunoglobulin can be present in an extrachromosomal replicating genetic element in the isolated B lymphocyte cell line. The nucleic acid encoding the at least one membrane immunoglobulin can be derived from a B lymphocyte cell line. The at least one exogenously incorporated membrane immunoglobulin activated by the first antigen is capable of controlling expression of the at least one exogenously incorporated secreted immunoglobulin reactive to the second antigen. The isolated B lymphocyte cell line can include at least one of naïve B lymphocyte, immature B lymphocyte, transitional B lymphocyte, mature B lymphocyte, B1 B lymphocyte, marginal zone B lymphocyte, follicular B lymphocyte, memory B lymphocyte, plasmablast, or plasma cell. The isolated B lymphocyte cell line can include a polyclonal population of B lymphocytes. The isolated B lymphocyte cell line can include a monoclonal population of B lymphocytes. The membrane immunoglobulin can include at least one of a membrane anchor, a cytoplasmic domain, a hinge region, and an extracellular ligand-binding domain.

In an embodiment, a modified B lymphocyte includes structural or functional features for exhibiting cellular cytotoxicity. For example, in an embodiment, a modified B lymphocyte cell or cell line produces one or more antibodies and has one or more B cell receptors (membrane immunoglobulins as described herein) that are specific to target antigens, such as tumor antigens (including but not limited to, antigens that are mutant forms of "normal" cellular antigens, as well as antigens that are modified by way of post-translational modifications, and antigens that are expressed in an abnormal way or in an abnormal level). In an embodiment, a modified B lymphocyte cell or cell line is capable of mounting a complete immune response with both humoral as well as cellular immune components. Thus, cytotoxicity expression can include secreted antibody or antibodies. Cytotoxicity expression can also include direct cell-to-cell contact that induces death (e.g., by lysis, necrosis, apoptosis, etc.). One of the goals of various embodiments is to provide highly specific, highly effective killing of target cells by the modified B lymphocytes described herein. In an embodiment, the target cells include cancer cells (e.g., tumor or other cancer cells). In an embodiment, the target cells include cells that are related to autoimmune disease or infection. In an embodiment, the target cells include donor or host cells that are reactive to donor cells from a cell, tissue, or organ transplant (e.g., graft-versus-host disease). In an embodiment, the target cells include cells related to pathological inflammation or infection.

A method for producing an immunoglobulin in an isolated B lymphocyte cell line as described herein can include isolating from a vertebrate subject exposed to, e.g., by infection, or immunized with at least one second antigen, a B lymphocyte cell line expressing at least one endogenous secreted immunoglobulin reactive to the at least one second antigen; introducing into the isolated B lymphocyte cell line at least one exogenous membrane immunoglobulin reactive to at least one first antigen to produce a recombinant B lymphocyte cell line; and selecting the isolated B lymphocyte cell line expressing the membrane immunoglobulin reactive to the at least one first antigen and expressing the at least one endogenous secreted immunoglobulin reactive to the at least one second antigen. The method of claim can include administering the at least one first antigen to stimulate the recombinant B lymphocyte cell line; and assessing production of the at least one endogenous secreted immunoglobulin reactive to the at least one second antigen in the recombinant B lymphocyte cell line. In the method, introducing into the at least one isolated recombinant B lymphocyte cell line at least one exogenous membrane immunoglobulin reactive to the at least one first antigen can include introducing at least one exogenous membrane immunoglobulin polypeptide reactive to the at least one first antigen. Introducing into the at least one isolated recombinant B lymphocyte cell line at least one exogenous membrane immunoglobulin reactive to the at least one first antigen can include introducing at least one exogenous nucleic acid encoding at least one membrane immunoglobulin reactive to the at least one first antigen. The method can include exposing the recombinant B lymphocyte cell line to the at least one first antigen to activate the recombinant B lymphocyte cell line to express the endogenous secreted immunoglobulin reactive to the at least one second antigen. The method can include isolating the endogenous secreted immunoglobulin reactive to the at least one second antigen from the recombinant B lymphocyte cell line or from a culture of the recombinant B lymphocyte cell line. In the method, activating the at least one exogenously incorporated membrane immunoglobulin with the first antigen is capable of controlling expression of the at least one exogenously incorporated nucleic acid encoding at least one secreted immunoglobulin reactive to the second antigen. The isolated B lymphocyte cell line can include at least one of naïve B lymphocytes, immature B lymphocytes, transitional B lymphocytes, mature B lymphocytes, follicular B lymphocytes, memory B lymphocytes, plasmablasts, or plasma cells. The isolated B lymphocyte cell line can include at least one memory B lymphocyte.

In an embodiment, the isolated B lymphocyte cell line that has been modified by way of a chimeric B cell receptor or recombinant B cell receptor includes utilizing scFv fragments in construction of the modified B cell receptor. In an embodiment, as described herein, transcription factors can also be constructed (e.g., on a separate vector) to be part of the modified B cell line(s).

A method for treating a subject that is afflicted with a disease or disorder (e.g., an autoimmune disease, cancer, or infection, etc.) includes administering a therapeutically effective amount of an isolated modified B lymphocyte cell line as disclosed herein. It is recognized that a therapeutically effective amount of cells to be given to a subject can be determined utilizing standard methods for immunotherapy and cell therapy programs.

A method for treating a disease in a vertebrate subject with an immunotherapeutic product as described herein can include isolating from a vertebrate subject exposed to, e.g., by infection, or immunized with at least one second antigen, a B lymphocyte cell line expressing at least one endogenous secreted immunoglobulin reactive to the at least one second antigen; introducing into the isolated B lymphocyte cell line at least one exogenous membrane immunoglobulin reactive to at least one first antigen to produce a recombinant B lymphocyte cell line; and selecting the recombinant B lymphocyte cell line expressing the membrane immunoglobulin reactive to the at least one first antigen and expressing the at least one endogenous secreted immunoglobulin reactive to the at least one second antigen for administration to one or more vertebrate subjects. The method can include administering the at least one first antigen to stimulate the recombinant B lymphocyte cell line; and testing for the presence of the at least one endogenous secreted immunoglobulin reactive to the at least one second antigen in the recombinant B lymphocyte cell line. The method can include administering to the vertebrate subject a pharmaceutical composition including the isolated B lymphocyte cell line; and administering to the vertebrate subject the at least one first antigen to stimulate the isolated B lymphocyte cell line to produce the at least one endogenous secreted immunoglobulin reactive to the at least one second antigen. The method can include confirming the presence of the at least one endogenous secreted immunoglobulin reactive to the at least one second antigen in a bloodstream of the vertebrate subject. The method can include administering the at least one first antigen to stimulate the recombinant B lymphocyte cell line; testing for the presence of the at least one endogenous secreted immunoglobulin reactive to the at least one second antigen; and administering to the vertebrate subject a pharmaceutical composition including the stimulated recombinant B lymphocyte cell line. The recombinant B lymphocyte cell line can be autologous to one of the one or more vertebrate subjects. The recombinant B lymphocyte cell line can be allogeneic to the one or more vertebrate subjects.

A method for producing at least one immunoglobulin in an isolated cell line as described herein can include introducing into at least one isolated B lymphocyte cell line at least one exogenous membrane immunoglobulin reactive to at least one first antigen to produce at least one first isolated B lymphocyte cell line; selecting the at least one first isolated B lymphocyte cell line expressing the membrane immunoglobulin reactive to the at least one first antigen; introducing into the at least one first isolated B lymphocyte cell line at least one exogenous nucleic acid encoding one or more secreted immunoglobulins reactive to at least one second antigen to produce at least one isolated recombinant B lymphocyte cell line; and selecting the at least one isolated recombinant B lymphocyte cell line expressing the one or more secreted immunoglobulin reactive to the at least one second antigen. The method can include selecting the at least one isolated recombinant B lymphocyte cell line expressing the at least one exogenous membrane immunoglobulin reactive to the at least one first antigen. The method can include administering the at least one first antigen to stimulate the at least one isolated recombinant B lymphocyte cell line; and testing for the presence of the one or more secreted immunoglobulins reactive to the at least one second antigen in the at least one isolated recombinant B lymphocyte cell line. The method can include introducing into the at least one first isolated B lymphocyte cell line at least one exogenous membrane immunoglobulin reactive to the at least one second antigen. The method can include introducing into the at least one isolated recombinant B lymphocyte cell line at least one exogenous nucleic acid sequence encoding one or more secreted immunoglobulins reactive to at least one third antigen to produce at least one isolated second recombinant B lymphocyte cell line; and selecting the at least one isolated second recombinant B lymphocyte cell line expressing the at least one secreted immunoglobulin reactive to the at least one second antigen and the at least one secreted immunoglobulin reactive to the at least one third antigen. The method can include administering the at least one first antigen to stimulate the at least one isolated second recombinant B lymphocyte cell line; and testing for the presence of the at least one exogenous secreted immunoglobulin reactive to the at least one third antigen in the recombinant B lymphocyte cell line. In the method, introducing into the at least one isolated B lymphocyte cell line the at least one exogenous membrane immunoglobulin reactive to the at least one first antigen can include introducing at least one exogenous membrane immunoglobulin reactive to the at least one first antigen. Introducing into the at least one isolated B lymphocyte cell line the at least one exogenous membrane immunoglobulin reactive to the at least one first antigen can include introducing an exogenous nucleic acid encoding at least one membrane immunoglobulin reactive to the at least one first antigen. Introducing into the at least one first isolated B lymphocyte cell line the at least one exogenous membrane immunoglobulin reactive to the at least one second antigen can include introducing at least one exogenous membrane immunoglobulin polypeptide reactive to the at least one second antigen. Introducing into the at least one first isolated B lymphocyte cell line the at least one exogenous membrane immunoglobulin reactive to the at least one second antigen can include introducing at least one exogenous nucleic acid encoding at least one membrane immunoglobulin reactive to the at least one second antigen. The method can include exposing the at least one isolated recombinant B lymphocyte cell line to the at least one first antigen, and testing for the activation of the at least one isolated recombinant B lymphocyte cell line to express the exogenous secreted immunoglobulin reactive to the at least one second antigen. The method can include isolating the exogenous secreted immunoglobulin reactive to the at least one second antigen from the at least one isolated recombinant B lymphocyte cell line or from a culture of the at least one isolated recombinant B lymphocyte cell line. In the method, activating the at least one exogenously incorporated membrane immunoglobulin with the first antigen is capable of controlling expression of the at least one exogenously incorporated nucleic acid encoding at least one secreted immunoglobulin reactive to the second antigen. The at least one isolated B lymphocyte cell line can include at least one of naïve B lymphocytes, immature B lymphocytes, transitional B lymphocytes, mature B lymphocytes, marginal zone B lymphocytes, B1 B lymphocytes, follicular B lymphocytes, memory B lymphocytes, plasmablasts, or plasma cells. The at least one isolated B lymphocyte cell line can include at least one memory B lymphocyte.

A method for treating a disease in a vertebrate subject with an immunotherapeutic product as described herein can include introducing into at least one isolated B lymphocyte cell line at least one exogenous membrane immunoglobulin reactive to at least one first antigen to produce at least one first isolated B lymphocyte cell line; selecting the at least one first isolated B lymphocyte cell line expressing the membrane immunoglobulin reactive to the at least one first antigen; introducing into the at least one first isolated B lymphocyte cell line at least one exogenous nucleic acid encoding one or more secreted immunoglobulins reactive to at least one second antigen to produce at least one isolated recombinant B lymphocyte cell line; selecting the at least one isolated recombinant B lymphocyte cell line expressing the secreted one or more immunoglobulin reactive to the at least one second antigens for administration to one or more vertebrate subjects. The method can include selecting the at least one isolated recombinant B lymphocyte cell line expressing the at least one exogenous membrane immunoglobulin reactive to the at least one first antigen. The method can include administering the at least one first antigen to stimulate the at least one isolated recombinant B lymphocyte cell line; and testing for the presence of the one or more secreted immunoglobulin reactive to the at least one second antigen in the at least one isolated recombinant B lymphocyte cell line. The method can include administering to the vertebrate subject a pharmaceutical composition including the at least one isolated recombinant B lymphocyte cell line; and administering to the vertebrate subject the at least one first antigen to stimulate the at least one isolated recombinant B lymphocyte cell line to produce the one or more exogenous secreted immunoglobulin reactive to the at least one second antigen. The method can include confirming the presence of the at least one exogenous secreted immunoglobulin reactive to the at least one second antigen in a bloodstream of the vertebrate subject. The method can include administering the at least one first antigen to stimulate the at least one isolated recombinant B lymphocyte cell line to produce the one or more exogenous secreted immunoglobulin reactive to the at least one second antigen; and administering to the vertebrate subject a pharmaceutical composition including the stimulated at least one isolated recombinant B lymphocyte cell line. The method can include introducing into the at least one first isolated B lymphocyte cell line at least one exogenous membrane immunoglobulin reactive to the at least one second antigen. The method can include introducing into the at least one isolated recombinant B lymphocyte cell line at least one exogenous nucleic acid encoding one or more secreted immunoglobulins reactive to at least one third antigen to produce at least one isolated second recombinant B lymphocyte cell line; and selecting the at least one isolated second recombinant B lymphocyte cell line expressing at least one of the secreted immunoglobulin reactive to the at least one second antigen and the secreted immunoglobulin reactive to the at least one third antigen. The method can include administering to the vertebrate subject a pharmaceutical composition including the at least one isolated second recombinant B lymphocyte cell line; and administering to the vertebrate subject the at least one first antigen to stimulate the at least one isolated second recombinant B lymphocyte cell line to produce the one or more exogenous secreted immunoglobulin reactive to the at least one second antigen and the one or more exogenous secreted immunoglobulin reactive to the at least one third antigen. The method can include confirming the presence of the at least one exogenous secreted immunoglobulin reactive to the at least one second antigen and the one or more exogenous secreted immunoglobulin reactive to the at least one third antigen in a bloodstream of the vertebrate subject. The method can include administering to the vertebrate subject the at least one first antigen to stimulate the at least one isolated second recombinant B lymphocyte cell line to produce the one or more exogenous secreted immunoglobulin reactive to the at least one second antigen and the one or more exogenous secreted immunoglobulin reactive to the at least one third antigen; and administering to the vertebrate subject a pharmaceutical composition including the stimulated at least one isolated second recombinant B lymphocyte cell line. The recombinant B lymphocyte cell line can be autologous to one of the one or more vertebrate subjects. The recombinant B lymphocyte cell line can be allogeneic to the one or more vertebrate subjects.

A method for producing at least one immunoglobulin in an isolated cell line as described herein can include introducing into at least one first isolated B lymphocyte cell line at least one exogenous nucleic acid encoding one or more secreted immunoglobulins reactive to at least one first antigen to produce at least one isolated recombinant B lymphocyte cell line; selecting the at least one isolated recombinant B lymphocyte cell line expressing the one or more secreted immunoglobulin reactive to the at least one first antigen; introducing into the at least one isolated B lymphocyte cell line at least one exogenous membrane immunoglobulin reactive to at least one second antigen to produce at least one first isolated B lymphocyte cell line; and selecting the at least one first isolated B lymphocyte cell line expressing the membrane immunoglobulin reactive to the at least one second antigen.

A method for treating a disease in a vertebrate subject with an immunotherapeutic product as described herein can include introducing into at least one first isolated B lymphocyte cell line at least one exogenous nucleic acid encoding one or more secreted immunoglobulins reactive to at least one first antigen to produce at least one isolated recombinant B lymphocyte cell line; selecting the at least one isolated recombinant B lymphocyte cell line expressing the secreted one or more immunoglobulin reactive to the at least one first antigens; introducing into the at least one isolated B lymphocyte cell line at least one exogenous membrane immunoglobulin reactive to at least one second antigen to produce at least one first isolated B lymphocyte cell line; and selecting the at least one first isolated B lymphocyte cell line expressing the membrane immunoglobulin reactive to the at least one second antigen for administration to the vertebrate subject.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
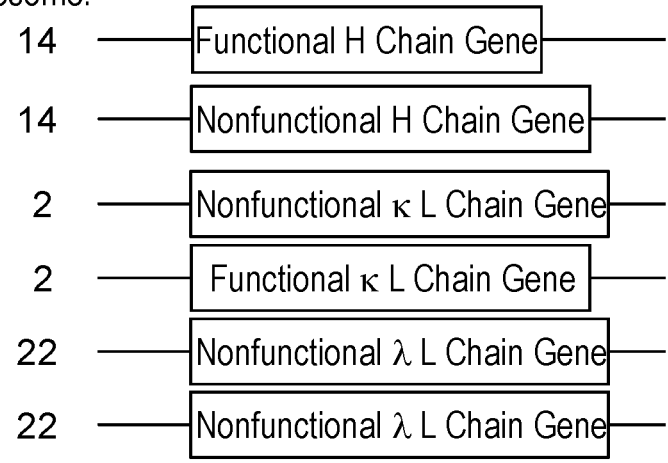
FIG. 1 is a schematic of a diagrammatic view of hypothetical immunoglobulin genes for memory B lymphocytes.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Compositions and methods are disclosed herein for producing one or more immunoglobulins in an isolated B lymphocyte cell line. Compositions and methods are disclosed herein for producing one or more immunoglobulins in the isolated B lymphocyte cell line that direct cell signaling by membrane immunoglobulin in the isolated B lymphocyte cell line. Immune cell therapy in a vertebrate subject can include administering to the vertebrate subject the isolated B lymphocyte cell line that synthesizes secreted immunoglobulins and membrane immunoglobulins each having different target antigens. Immune cell therapy in a vertebrate subject can include administering to the vertebrate subject antigen presenting cells comprised of the isolated B lymphocyte cell line that directs antigen internalization and processing to produce exceptional antigen presenting cells. The isolated B lymphocyte cell line can produce antigen presenting cells that are exceptional or superior at capturing, internalizing and presenting the antigen recognized by the endogenous or exogenously derived membrane immunoglobulin. Compositions and methods are disclosed herein for treating a disease in a vertebrate subject with an immunotherapeutic product. The immunotherapeutic product can include the isolated B lymphocyte cell line having an endogenously-derived or exogenously derived membrane immunoglobulin reactive to a first antigen wherein the isolated B lymphocyte cell line produces one or more secreted immunoglobulins reactive to a second antigen. The immunotherapeutic product can include the isolated B lymphocyte cell line that can be a monoclonal B lymphocyte cell line or polyclonal B lymphocyte cell line that produces one or more secreted antibodies and/or a reassigned biological agent. The immunotherapeutic product can include the isolated B lymphocyte cell line that produces one or more secreted antibodies, e.g., antibodies that recognize different epitopes on the same antigen. The immunotherapeutic product can include the isolated B lymphocyte cell line as one or more antigen presenting cells.

The isolated B lymphocyte cell line can include an immunotherapeutic product administered to a vertebrate subject to develop long-lived isolated B lymphocytes in the vertebrate subject for immune surveillance of chronic disease. The immunotherapeutic product can include the isolated B lymphocyte cell line having an endogenously-derived or exogenously derived membrane immunoglobulin that can be administered to a vertebrate subject to provide an antigen presenting cell to the vertebrate subject.

An isolated cell line as described herein can include an isolated B lymphocyte cell line capable of expressing at least one exogenously incorporated membrane immunoglobulin reactive to a first antigen and at least one endogenous secreted immunoglobulin reactive to a second antigen. The at least one exogenously incorporated membrane immunoglobulin can include an exogenously incorporated membrane immunoglobulin polypeptide. The at least one exogenously incorporated membrane immunoglobulin can include an exogenously incorporated nucleic acid encoding a membrane immunoglobulin polypeptide, wherein the cell line is capable of expressing the membrane immunoglobulin polypeptide.

An isolated recombinant cell line as described herein can include an isolated B lymphocyte cell line capable of expressing at least one exogenously incorporated membrane immunoglobulin reactive to a first antigen and at least one exogenously incorporated nucleic acid encoding secreted immunoglobulin reactive to a second antigen.

An isolated recombinant cell line as described herein can include an isolated B lymphocyte cell line capable of expressing at least one exogenously incorporated gene integrated at an active, rearranged immunoglobulin gene under the control of immunoglobulin variable region promoters and immunoglobulin enhancers. For example, expression of a gene for a reassigned biological agent integrated at a rearranged immunoglobulin H-chain gene under the control of a variable heavy chain promoter and the immunoglobulin mu enhancer.

An isolated recombinant B cell line as described herein can include the capability of expressing a reassigned biological agent, such as a protein, glycoprotein, proteoglycan, nucleic acid (RNA, DNA, PNA, etc.), or other biological agent that is not ordinarily expressed from the Ig chromosomal loci for Ig H-chain and Ig L-chain in a naturally occurring B cell. For example, the recombinant B cells described herein can include the capability of expressing at least one cytokine, cytokine receptor, small molecule, protein, monosaccharide, disaccharide, polysaccharide, or other biological agent. In an embodiment, the reassigned biological agent can include at least one enzyme, G-protein-coupled receptor, or ligand. In an embodiment, the reassigned biological agent can include at least one of tumor necrosis factor (TNF), TNF-related apoptosis-inducing ligand (TRAIL/Apo2L), OX-40, CD95 (FasL/Apo-1L), gamma interferon (γ-IFN), perforin, interleukin-21 (IL-21), IL-12, IL-15, IL-10, IL-22, IL-2, IL-3, IL-4, IL-5, IL-6, IL-7, IL-12, IL-15, IL-17, IL-18, IL-23, pathogen-associated molecular patterns (PAMPs), damage-associated molecular patterns (DAMPs), CXCL-1, CXC, CC, GM-CSF, G-CSF, M-CSF, stem cell factor, TGF-beta, INFgamma, INFalpha, TNFalpha, or other cytokine. In an embodiment, the reassigned biological agent can include at least one of a tumor-associated antigen, cell surface antigen or viral antigen. For example, tumor associated antigens can include: MUC-1, MUC-16, prostate cancer membrane antigen (PCMA), epidermal growth factor receptor 2 (HER2), B cell maturation antigen (BCMA), CD38, CD30, MAGE A1, NY-ESO-1 and CD44v6. Viral antigens can include: HIV-1 proteins: gag, env, gp41, gp120, RNA-dependent DNA polymerase; influenza hemagglutinin; and hepatitis C virus proteins: NS3, NS4 and NS5. In an embodiment, the reassigned biological agent includes a bacterial component configured to induce other B cells to become IgA producing plasma cells. In an embodiment, the isolated modified B cell is utilized in the gut of a subject to work cooperatively or competitively with the microbiome in order to maintain health or alter a disease state in the subject. See e.g., Shi et al., Mil. Med. Res. 2017; 4:14, online Apr. 27, 2017, which is incorporated herein by reference. In an embodiment, the disease state includes disease that affects the gut. In an embodiment, the disease state includes disease that affects another system of the subject's body, including a system disease.

In an embodiment, expression of an agent can be initiated by engagement of the modified B cell's immunoglobulin receptor (BCR). For example, transcription of the reassigned biological agent is initiated in the cascade of events following appropriate antigen binding occurring with the modified B cell's BCR as described. Antigen binding to membrane IgG leads to tyrosine phosphorylation on Igα and Igβ (signal transduction proteins comprising the BCR) which initiate signaling pathways that activate and translocate intracellular messengers and transcription factors (e.g., NF-AT, Ras/Erk, Bright and BTK) which lead to memory B cell activation and Ig gene expression. (See e.g., Wienands et al., *Current Topics in Microbiology and Immunology* 393: 107-121, 2016 and Schmidt et al., *EMBO J.* 28: 711-724, 2009 which are incorporated herein by reference.)

In an embodiment, the modified B lymphocyte is modified to express at least one reassigned biological agent without further modification. In an embodiment, the modified B lymphocyte is modified to constitutively express the at least one reassigned biological agent. As described herein, the reassigned biological agent includes secreted molecules (e.g., cytokines, chemokines, cytotoxins, etc.) and can play a role in a larger immunological response (e.g. stimulating T cells, NK cells, macrophages, epithelial cells, other B cells, neutrophils, basophils, eosinophils, etc.). In an embodiment, the modified B lymphocyte is modified to inductively express the at least one reassigned biological agent (e.g., expression of the at least one reassigned biological agent can be driven by receptor-ligand binding, by transcription factor, by protein production of another biological reaction, etc.). In an embodiment, the modified B lymphocyte is also modified in other ways as described herein (e.g., to express an exogenous membrane immunoglobulin receptor and/or to express an exogenous secreted immunoglobulin receptor and/or to express cytotoxic agents, etc.).

In an embodiment, as described herein, the reassigned biological agent can include an agent that a naturally occurring B lymphocyte would not ordinarily express at all but due to its modification, the modified B lymphocyte is capable of expressing the reassigned biological agent. In an embodiment, as described herein, the reassigned biological agent can include an agent that a naturally occurring B lymphocyte would not ordinarily express in specific circumstances or conditions but due to its modification, the modified B lymphocyte is capable of expressing the reassigned biological agent under those specific circumstances or conditions. For example, under certain circumstances, a naturally occurring regulatory B lymphocyte expresses and secretes IL-10 or TFG-beta 1, while a naturally occurring effector B lymphocyte produces cytokines such as IL-2, IL-4, TNFalpha, IL-6, or INFgamma. The determination of a regulatory B lymphocyte or effector B lymphocyte is based on the exposure of those particular cells to antigen and/or other cytokines and immune modulators. (See, e.g., Lund, *Curr. Opin. Immunol.* 2008 June; 20(3):332-338, which is incorporated by reference herein.)

With regard to our modified B lymphocytes, a B lymphocyte that would (under naturally occurring circumstances) express IL-2, can instead be modified to secrete IL-10, for example. Thus, the IL-10 would fulfill the role of a reassigned biological agent. Conversely, if a naturally occurring B lymphocyte would (under naturally occurring circumstances) express IL-10, but it is modified to constitutively or inductively secrete IL-2 regardless of the particular immunological conditions, then IL-2 would fulfill the role of a reassigned biological agent. Thus, the modification of a reassigned biological agent acts as a powerful tool to direct immune responses both in the modified B lymphocytes themselves, as well as the other players in the immune reaction (epithelial cells, neurons, other immune cells, etc.). This can be particularly useful, for example, with regard to "misplaced" immune reactions such as with tumor immunology (e.g., tumor suppression of standard immune response to tumor antigens), infectious disease (e.g., viral evasion of standard immune surveillance) or autoimmunity (e.g., heightened inflammation or highly reactive immune response to "self" or "no danger" antigens), etc.

A method for producing an immunoglobulin in an isolated B lymphocyte cell line as described herein can include isolating from a vertebrate subject exposed to, e.g., by infection, or immunized with at least one second antigen, a B lymphocyte cell line expressing at least one endogenous secreted immunoglobulin reactive to the at least one second antigen; introducing into the isolated B lymphocyte cell line at least one exogenous membrane immunoglobulin reactive to at least one first antigen to produce a recombinant B lymphocyte cell line; and selecting the isolated B lymphocyte cell line expressing the membrane immunoglobulin reactive to the at least one first antigen and expressing the at least one endogenous secreted immunoglobulin reactive to the at least one second antigen. As described herein, the modification A method for treating a disease in a vertebrate subject with an immunotherapeutic product as described herein can include isolating from a vertebrate subject exposed to, e.g., by infection, or immunized with at least one second antigen, a B lymphocyte cell used to generate a cell line expressing at least one endogenous secreted immunoglobulin reactive to the at least one second antigen; introducing into the isolated B lymphocyte cell at least one exogenous membrane immunoglobulin reactive to at least one first antigen to produce a recombinant B lymphocyte cell line; and selecting the recombinant B lymphocyte cell line expressing the membrane immunoglobulin reactive to the at least one first antigen and expressing the at least one endogenous secreted immunoglobulin reactive to the at least one second antigen for administration to one or more vertebrate subjects.

A method for producing at least one immunoglobulin in an isolated cell line as described herein can include introducing into at least one isolated B lymphocyte cell at least one exogenous membrane immunoglobulin reactive to at least one first antigen to produce at least one first isolated B lymphocyte cell line; selecting the at least one first isolated B lymphocyte cell line expressing the membrane immunoglobulin reactive to the at least one first antigen; introducing into the at least one first isolated B lymphocyte cell line at least one exogenous nucleic acid encoding one or more secreted immunoglobulins reactive to at least one second antigen to produce at least one isolated recombinant B lymphocyte cell line; and selecting the at least one isolated recombinant B lymphocyte cell line expressing the one or more secreted immunoglobulin reactive to the at least one second antigen.

A method for treating a disease in a vertebrate subject with an immunotherapeutic product as described herein can include introducing into at least one isolated B lymphocyte cell at least one exogenous membrane immunoglobulin reactive to at least one first antigen to produce at least one first isolated B lymphocyte cell line; selecting the at least one first isolated B lymphocyte cell line expressing the membrane immunoglobulin reactive to the at least one first antigen; introducing into the at least one first isolated B lymphocyte cell line at least one exogenous nucleic acid encoding one or more secreted immunoglobulins reactive to at least one second antigen to produce at least one isolated recombinant B lymphocyte cell line; selecting the at least one isolated recombinant B lymphocyte cell line expressing the secreted one or more immunoglobulin reactive to the at least one second antigens for administration to one or more vertebrate subjects.

A method for producing at least one immunoglobulin in an isolated cell line as described herein can include introducing into at least one first isolated B lymphocyte cell at least one exogenous nucleic acid encoding one or more secreted immunoglobulins reactive to at least one first antigen to produce at least one isolated recombinant B lymphocyte cell line; selecting the at least one isolated recombinant B lymphocyte cell line expressing the one or more secreted immunoglobulin reactive to the at least one first antigen; introducing into the at least one isolated B lymphocyte cell line at least one exogenous membrane immunoglobulin reactive to at least one second antigen to produce at least one first isolated B lymphocyte cell line; and selecting the at least one first isolated B lymphocyte cell line expressing the membrane immunoglobulin reactive to the at least one second antigen.

A method for treating a disease in a vertebrate subject with an immunotherapeutic product as described herein can include introducing into at least one first isolated B lymphocyte cell at least one exogenous nucleic acid encoding one or more secreted immunoglobulins reactive to at least one first antigen to produce at least one isolated recombinant B lymphocyte cell line; selecting the at least one isolated recombinant B lymphocyte cell line expressing the secreted one or more immunoglobulin reactive to the at least one first antigens; introducing into the at least one isolated B lymphocyte cell line at least one exogenous membrane immunoglobulin reactive to at least one second antigen to produce at least one first isolated B lymphocyte cell line; and selecting the at least one first isolated B lymphocyte cell line expressing the membrane immunoglobulin reactive to the at least one second antigen for administration to the vertebrate subject.

An isolated recombinant cell line includes an isolated B lymphocyte cell line capable of expressing at least one endogenous membrane immunoglobulin reactive to a first antigen and at least one exogenously incorporated nucleic acid encoding at least one secreted immunoglobulin reactive to a second antigen.

In an embodiment, a modified B lymphocyte includes structural or functional features for exhibiting cellular cytotoxicity. For example, in an embodiment, a modified B lymphocyte cell or cell line produces one or more antibodies and has one or more B cell receptors (membrane immunoglobulins as described herein) that are specific to target antigens, such as tumor antigens (including but not limited to, antigens that are mutant forms of "normal" cellular antigens, as well as antigens that are modified by way of post-translational modifications, and antigens that are expressed in an abnormal way or in an abnormal level). In an embodiment, a modified B lymphocyte cell or cell line is capable of mounting a complete immune response with both humoral as well as cellular immune components.

In an embodiment, a modified B lymphocyte that exhibits cytotoxicity is competent to express (directly or indirectly) at least one of perforin, granzymes, and other cytotoxic components. For example, in an embodiment, the B cell receptor (membrane bound immunoglobulin) signals to elicit cytotoxic effectors when, engaged with a tumor cell (i.e. the B cell receptor engages with an antigen of a tumor cell). In an embodiment, the modified lymphocyte is competent to secrete an antibody that is cytotoxic (e.g., by way of fixing complement or engaging ADCC [antibody-dependent cell-mediated cytotoxicity]) for the same tumor cell(s).

In an embodiment, a modified B lymphocyte cell is derived from B cells following vaccination with tumor antigens, for example, or from donor peripheral blood lymphocytes by modification of expression of at least one of antibody or B cell receptor (e.g., chimeric B cell receptor or recombinant B cell receptor).

In an embodiment, a modified B lymphocyte cell is modified to express cytotoxicity by way of expression of a recombinant B cell receptor or a chimeric receptor with scFv and membrane immunoglobulin for extracellular transmembrane and cytoplasmic domains along with a cytoplasmic domain from IL21 receptor and TLR or another signaling molecule to elicit expression of granzyme, perforin, etc. from the modified B lymphocyte cell.

For example, in the case of HIV infection, the modified B lymphocyte cell is able to mount a humoral as well as cytotoxic immune reaction. For example, the modified B lymphocyte cell can secrete neutralizing antibody for HIV particles or virally-infected cells. Optionally, in addition to the neutralizing antibody, the modified B lymphocyte cell can directly induce apoptosis or otherwise directly kill HIV infected cells (e.g. infected T cells in the lymph nodes, known as "reservoirs" of infected T cells not destroyed under current HIV anti-viral therapies.

Likewise, the modified B lymphocyte cell can target auto-immune cells (e.g. multiple sclerosis cells, arthritis cells, etc.) that can be identified as self-reactive. In an embodiment, the modified B lymphocyte cell induces apoptosis or otherwise directly kills such self-reactive cells. In an embodiment, these self-reactive cells include at least one of B cells, T cells, macrophages, or other immune cells. In an embodiment, these self-reactive cells include inflammatory cells In an embodiment, a modified B lymphocyte cell is modified to express a recombinant B cell receptor or chimeric B cell receptor specific for a first antigen and an antibody recognizing a second antigen, providing increased specificity as well as increased cellular cytotoxicity and antibody-mediated killing of the target cells (e.g. tumor cells, auto-immune cells, infected cells, inflammatory cells, necrotic cells, regulatory cells (e.g., regulatory T cells, regulatory B cells and myeloid-derived suppressor cells).

In an embodiment, a modified B lymphocyte cell with chimeric B cell receptor or recombinant B cell receptor has been modified to specifically react to one or more target cells, and exhibit cytotoxicity for the one or more target cells. In an embodiment, the modified B lymphocyte cell or cell line is engineered specifically for reaction with one or more tumor cells or tumor cell types. In an embodiment, the modified B lymphocyte cell or cell line is engineered through laboratory techniques and optionally through use of computer data and/or modeling of various components of the B lymphocytes.

In an embodiment, the modified B lymphocyte cell with a chimeric B cell receptor or recombinant B cell receptor includes a modified receptor that is competent to transduce signals that induce expression of cytotoxic effector molecules, when the receptor is engaged.

In an embodiment, the recombinant B cell receptor or chimeric B cell receptor includes a heterologous extracellular, trans-membrane and cytoplasmic signaling domain(s) that elicit expression of cytotoxic effector molecules.

In an embodiment, the recombinant B cell receptor or chimeric B cell receptor includes a cytoplasmic domain derived from at least one of the common gamma chain, IL-21R, a Toll-like receptor (TLR) or CD40. In an embodiment, the recombinant B cell receptor or chimeric B cell receptor is competent to elicit expression of cytotoxic effector molecules, such as perforin, granzyme B, Fas ligand, TRAIL, or others. In an embodiment, the recombinant B cell receptor or chimeric B cell receptor is competent to elicit expression of a TNF family receptor in the target cell, such as TNFR1, Fas receptor, DR4, DR5, or other "death domain" receptor.

In an embodiment, the modified B cell secretes or expresses at least one of TNF-alpha ligand, lymphotoxin alpha or beta, OX40L, CD154, LIGHT, TL1-A, CD70, Siva, CD153, 4-1BB, RANKL, TWEAK, APRIL, BAFF, CAMLG, NGF, BDNF, NT-3, NT-4, GITR, TL1A, or EDA-A2.

For example, optimal stimulation for effective expression of CD70 on IFN-alpha-induced monocyte-derived dendritic cells, widely used for tumor immunotherapy, has been studied by exposure to various maturation-inducing factors (Toll-like receptor ligands, CD40 ligand and pro-inflammatory mediators, including prostaglandin E2). See Arimoto-Miyamoto et al., Immunol, 2010 May 130(1): 137-149, which is incorporated herein by reference. Further, the CD70-CD27 interaction diminished production of IL-10. Id.

For example, expression of CD153 on B cells in the presence of B cell receptor engagement and IL-4, results in Ig class switching, while CD154 expression contributes to CD153 expression. See Cerutti, et al., J Immunol 2000 Jul. 15; 165(2):786-794, which is incorporated herein by reference. The CD153 "switch" for expression of alternate or additional genes or expression cassettes can be built into the modified B cells described herein.

For example, OX40-OX40L interactions have been found to play a role in the development of several different inflammatory and autoimmune diseases, and which may be targeted for intervention. See for example, Croft, et al., Immunol Rev 2009 May, 229(1): 173-191, which is incorporated herein by reference.

In an embodiment, the recombinant B cell receptor or chimeric B cell receptor includes at least one extracellular domain specific for one or more target antigens. In an embodiment, the recombinant B cell receptor or chimeric B cell receptor includes a modified receptor that recognizes a first antigen, and secretes an antibody that recognizes a second antigen. In an embodiment, the recombinant B cell receptor or chimeric B cell receptor includes a modified receptor that recognizes a first epitope of one antigen and secretes an antibody that recognizes a second epitope of the same antigen. Thus, the modified B cells (with recombinant B cell receptor or chimeric B cell receptor) can be designed and engineered by laboratory techniques to be responsive to tumor cells with greater specificity and greater cytotoxic activity. In an embodiment, the modified B cells that exhibit cytotoxicity are further included in embodiments of B cells described herein that exhibit a chimeric B cell receptor or recombinant B cell receptor specific for one antigen and secrete antibodies specific for a different antigen than its B cell receptor. Such memory B cells can also include the targeted cytotoxicity characteristics as described herein.

In an embodiment, the target cells include cells that have been infected by virus, mycoplasma, bacteria, yeast, or other microorganism. In an embodiment, the target cells include tumor cells, such as primary tumor cells, circulating tumor cells, or metastatic tumor cells. In an embodiment, the target cells include auto-immune cells.

In an embodiment, a method of making the modified B lymphocyte cells includes engineering cells by way of laboratory techniques. In an embodiment, a method of using the modified B lymphocytes for treatment of disease includes administering a therapeutically effective amount of the modified B lymphocyte cells to a subject. Specific examples of methods of making the modified B lymphocyte cells are described in greater detail in the Prophetic Examples section herein.

In an embodiment, a modified B lymphocyte cell or cell line as described herein is engineered, and utilized for administration to a subject for treatment. As described herein, in an embodiment, the subject has active disease. In an embodiment, the subject has chronic disease. In an embodiment, the subject has been exposed to a disease-causing agent and may or may not yet have symptoms of disease. In an embodiment, the subject has latent disease.

A method for producing an immunoglobulin in a recombinant B lymphocyte cell line includes isolating from a vertebrate subject exposed to, e.g., by infection, or immunized with at least one first antigen, a B lymphocyte cell line expressing at least one endogenous membrane immunoglobulin reactive to the at least one first antigen; introducing into the isolated B lymphocyte cell line at least one exogenous nucleic acid encoding at least one of a secreted immunoglobulin reactive to at least one second antigen to produce a recombinant B lymphocyte cell line; and assaying for presence of the at least one exogenous secreted immunoglobulin reactive to the at least one second antigen to select the recombinant B lymphocyte cell line.

A method for treating a disease in a vertebrate subject with an immunotherapeutic product includes isolating from a vertebrate subject exposed to, e.g., by infection, or immunized with at least one first antigen, a B lymphocyte cell line expressing at least one endogenous membrane immunoglobulin reactive to the at least one first antigen; introducing into the isolated B lymphocyte cell line at least one of at least one exogenous nucleic acid encoding at least one secreted immunoglobulin reactive to at least one second antigen; assaying for presence of at least one exogenous secreted immunoglobulin reactive to the at least one second antigen to select the recombinant B lymphocyte cell line for administration to the vertebrate subject.

The isolated B lymphocytes can be used for immunotherapy:
  Long-lived isolated B lymphocytes can be used for immune surveillance of chronic disease.
  Isolated B lymphocytes having membrane immunoglobulin recognizing antigen can act as exceptional antigen presenting cells to present antigen to T lymphocytes.
  Immunotherapy with polyclonal autologous isolated B lymphocytes is a valuable protocol. For example, influenza immune B lymphocytes can be transfected en masse with retroviral vectors. Alternatively, one may immunize with a vaccine and transfect multiple isolated B lymphocytes, e.g., polyclonal B lymphocytes, recognizing different epitopes of the same antigen.

A number of protocols, as presented herein, may be utilized to produce an isolated B lymphocyte cell line as stated in more detail in the detailed description and examples. An isolated B lymphocyte cell line capable of expressing at least one endogenous membrane immunoglobulin reactive to a first antigen or capable of expressing at least one endogenous secreted immunoglobulin reactive to a first antigen can be developed by immunizing an individual with a model antigen, e.g., dinitrophenol (DNP) or an influenza antigen, to elicit memory B cells with endogenous membrane immunoglobulin, e.g., B cell receptors (BCR), reactive to the DNP model antigen or the influenza antigen and/or endogenous soluble immunoglobulin, e.g., antibody reactive to the DNP antigen or the influenza antigen.

An isolated B lymphocyte cell line capable of expressing at least one exogenous secreted immunoglobulin reactive to a broadly neutralizing influenza antigen can be developed by isolating human B cells from an individual who is immune to influenza virus infection and immortalizing the human B cells by infecting the isolated B cells with Epstein Barr virus (EBV). Methods to clone immunoglobulin heavy (H) chain and light (L) chain genes from the EBV-immortalized B lymphocyte cell line may be used. See e.g., U.S. Pat. No. 7,741,077 issued to Grawunder et al. on Jun. 22, 2010 and Early et al., Proc. Natl. Acad. Sci. USA 76: 857-861,1979, which are incorporated herein by reference. To promote homologous recombination the immunoglobulin genes encoding the H chain and L chain for a secreted anti-influenza antibody are cloned in plasmid targeting vectors to obtain targeted integration in the corresponding nonfunctional, germline Ig loci on chromosomes 14 and 2 respectively. Alternatively memory B cells obtained from a patient with a chronic viral infection can be genetically engineered by replacing their functional, expressed Ig genes with exogenous Ig genes encoding a membrane immunoglobulin, e.g., anti-DNP antibody. The Ig H and Ig L chain genes encoding the anti-DNP antibody may be inserted in the functional, expressed Ig gene loci on chromosomes 14 and 2 by using methods of homologous recombination. See e.g., U.S. Pat. Nos. 5,202,238, 6,570,061, and 6,841,383.

Memory B cells expressing anti-DNP membrane IgG can be engineered to express Ig genes encoding a secreted IgG antibody specific for influenza. The anti-influenza $IgG_1$ H chain gene (i.e., $\gamma_1$-H chain gene) may be engineered to remove coding sequences for the membrane spanning domain (™), the cytoplasmic amino acids (Cyt), and a polyA addition site to yield a $\gamma_1$-H chain gene encoding a secreted H chain only.

To obtain human immunoglobulin (Ig) genes encoding a specific antibody against cancer, e.g., PSA, or for infectious disease, a hybridoma cell line that produces the anti-PSA antibody is constructed. For example transgenic mice with human Ig genes (e.g., XenoMouse® available from Abgenix Inc., Fremont, CA) are immunized with PSA and their B cells are fused with a myeloma cell fusion partner, e.g. SP2/0 cells (available from American Type Culture Collection, Manassas, VA) to create hybridoma cell clones expressing human antibodies (see e.g., U.S. Pat. No. 8,013,128 Ibid.). Supernatants from the hybrid clones are screened using an immunoassay to detect human IgG antibodies which bind PSA protein. Hybridoma clones producing antibodies that recognize PSA are expanded and antibodies from each clone are tested using a Biacore™ A100 instrument (available from GE Healthcare, Piscataway, NJ) to measure antibody affinity and specificity for PSA (see e.g., GE Healthcare, Application Note 84, "Early kinetic screening of hybridomas . . . " which is incorporated herein by reference). Hybridomas expressing high affinity antibodies for PSA are selected for cloning of their human Ig genes, for example, by homologous recombination.

The engineered immunoglobulin genes encoding a membrane immunoglobulin are expressed in a mammalian cell line and the membrane IgG is purified from the cell line. For example, a kappa (κ) L chain gene and the modified γ-1 H chain gene are inserted in a lentiviral expression vector using standard recombinant DNA methods (see e.g., U.S. Patent Publication No. 2007/0116690 by Yang et al. published on May 24, 2007 which is incorporated herein by reference). The viral vector is used to transfect Chinese Hamster Ovary (CHO) cells (available from American Type Culture Collection, Manassas, VA) which are engineered to express the membrane immunoglobulin.

To insure that the recombinant memory B cells are safe for use in patients a suicide gene may be introduced into the B cells. To stop uncontrolled proliferation (and other adverse events) by the recombinant memory B cells, a suicide gene, herpes simplex virus-thymidine kinase gene (HSV-TK) is introduced using a retroviral expression vector. Methods to insert and express the HSV-TK gene and to activate a cytotoxic prodrug such as ganciclovir are known (see e.g., U.S. Pat. No. 6,576,464 issued to Gold and Lebkowski on Jun. 10, 2003 and U.S. Pat. No. 5,997,859 issued to Barber et al. on Dec. 7, 1999 which are incorporated herein by reference). To stop the growth of recombinant B cells deemed unsafe or contributing to an adverse event the B cells expressing HSV-TK are provided with 20 μM ganciclovir (available as Cytovene IV from Roche Laboratories, Nutley, NJ). Conversion of ganciclovir into a toxic metabolite by the B cells expressing HSV-TK results in their death. Cells not expressing HSV-TK are not harmed by ganciclovir.

In another embodiment, chemical inducers of dimerization (CID) can be used, in which a proapoptotic molecule is adapted to encompass one or more binding sites for a CID, which once reaching its target(s) causes their oligomerization with ensuing activation of the apoptotic pathway. In this manner, different apoptotic pathways can operate as suicide systems, including the death receptor Fas and the enzyme Caspase 9. Beside a very low risk for immunogenicity, these suicide genes share the advantages of non cell-cycle dependency, full clinical compatibility and optimal biodistribution, as CID are small molecule exquisitely designed for suicide purposes. See, for example, J Cancer. 2011; 2: 378-382, which is incorporated herein by reference.

The isolated cell line can include an isolated B lymphocyte cell line or an isolated recombinant B lymphocyte cell line that recognizes one or more antigens to an infectious bacterial or viral disease, e.g., influenza antigen. Table 1 includes examples of protocols for constructing the isolated B lymphocyte cell line or the isolated recombinant B lymphocyte cell lines including an exogenously-derived and/or endogenously-derived membrane immunoglobulin and exogenously-derived and/or endogenously-derived secreted immunoglobulin. The secreted immunoglobulin from the isolated recombinant B lymphocyte cell line can include one or more secreted anti-influenza broadly neutralizing antibodies (Flu BNAb). The anti-influenza broadly neutralizing antibodies can be directed to two or more epitopes on the same influenza antigen (Flu BNAb1 and Flu BNAb2). The secreted anti-influenza immunoglobulin from the isolated recombinant B lymphocyte cell line can include one or more secreted polyclonal antibodies (Flu $Ab_n$) to the influenza antigen.

memory B lymphocytes from a vertebrate subject. The isolated memory B lymphocytes are transfected with a nucleic acid vector including immunoglobulin genes encoding anti-DNP membrane immunoglobulin only and not anti-DNP secreted immunoglobulin. B lymphocytes with anti-DNP membrane immunoglobulin can be selected and transfected with immunoglobulin genes encoding two anti-influenza BNAbs to two different epitopes of the influenza antigen. The immunoglobulin genes encoding each BNAb can encode membrane and secreted forms of the BNAbs.

The isolated recombinant anti-influenza B lymphocytes can be transferred to a vertebrate subject to protect the vertebrate subject from influenza infection. The long-lived anti-influenza B lymphocytes can be activated at will to produce two anti-influenza BNAbs by injecting DNP-KLH into the vertebrate subject when flu symptoms arise or when a pandemic hits. The long-lived anti-influenza B lymphocytes can also be activated at will to produce two anti-influenza BNAbs by injecting influenza antigen into the vertebrate subject. Unlike Protocol 1, no secreted immunoglobulin to DNP-KLH will be produced when the B lymphocytes are activated by DNP-KLH or by influenza antigen.

B lymphocyte protocol 3 is a protocol to produce polyclonal isolated recombinant B lymphocytes. The protocol 3 immunizes a vertebrate subject with influenza vaccine, e.g., tripartite seasonal influenza vaccine. Memory B lymphocytes that express membrane immunoglobulin recognizing the influenza vaccine antigens are selected in the vertebrate subject. The selected polyclonal anti-influenza memory B lymphocytes are transfected with immunoglobulin genes encoding an anti-DNP membrane immunoglobulin.

The polyclonal anti-influenza B lymphocytes can be transferred to a vertebrate subject to protect the vertebrate subject from influenza infection. The polyclonal, long-lived anti-flu B cells can be activated en mass by injecting

| B lymphocyte cell line | Membrane Immunoglobulin | | Secreted Immunoglobulin 1 | | Membrane Immunoglobulin 2 | | Secreted Immunoglobulin 2 | |
|---|---|---|---|---|---|---|---|---|
| 1 | DNP-KLH | endog | Flu BNAb | exog | Flu BNAb | exog | DNP-KLH | endog |
| 2 | DNP-KLH | exog | Flu BNAb1 | exog | Flu BNAb1 | exog | Flu BNAb2 | exog |
| 3 | DNP-KLH | exog | Flu $Ab_n$ | endog | Flu $Ab_n$ | endog | None | none |
| 4 | Flu $Ab_n$ | endog | Flu $Ab_n$ | endog | Flu BNAb | exog | Flu BNAb | exog |

B lymphocyte protocol 1 is a protocol to produce isolated recombinant B lymphocytes. The protocol 1 immunizes a vertebrate subject with DNP-KLH (dinitrophenyl-Keyhole Limpet Hemocyanin) and select memory B lymphocytes including membrane immunoglobulin recognizing DNP and secreted immunoglobulin recognizing DNP. Anti-DNP B lymphocytes can be transfected with nucleic acid vector including immunoglobulin genes encoding membrane and secreted anti-influenza broadly neutralizing antibody (BNAb).

The isolated recombinant anti-influenza B lymphocytes can be transferred to a vertebrate subject to protect the vertebrate subject from influenza infection. The long-lived anti-influenza B lymphocytes can be activated at will by injecting DNP-KLH into the vertebrate subject when flu symptoms arise or when a pandemic hits.

B lymphocyte protocol 2 is a protocol to produce isolated recombinant B lymphocytes. The protocol 2 isolates DNP-KLH into the vertebrate subject when flu symptoms arise or when a pandemic hits. In addition individual B lymphocyte clones can be activated by their cognate influenza antigen.

B lymphocyte protocol 4 is a protocol to produce polyclonal isolated recombinant B lymphocytes. The protocol 4 immunizes a vertebrate subject with influenza vaccine, e.g., tripartite seasonal vaccine. Memory B lymphocytes that express membrane immunoglobulin recognizing the influenza vaccine antigens are selected in the vertebrate subject. Polyclonal anti-influenza B lymphocytes are transfected with immunoglobulin genes encoding anti-influenza BNAb in both membrane form and secreted form.

Figure 8A:
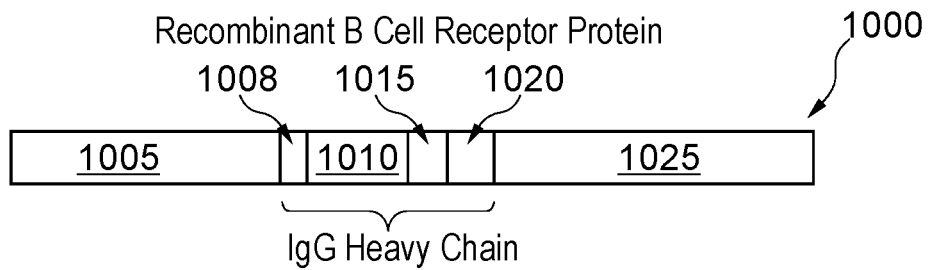
FIG. 8A is a schematic of a diagrammatic view of a recombinant B cell receptor protein.

The isolated recombinant polyclonal anti-influenza B lymphocytes can be transferred to a vertebrate subject to protect the vertebrate subject from influenza infection. The polyclonal, long-lived anti-influenza B lymphocytes can be activated en mass by injecting a full spectrum of influenza vaccine antigens into the vertebrate subject when flu symptoms arise or when a pandemic hits. Each B lymphocyte produces a BNAb and a clone-specific immunoglobulin reactive with influenza.

In some aspects, the isolated B lymphocyte cell line including at least one exogenously incorporated membrane immunoglobulin activated by the first antigen is capable of controlling expression of the at least one endogenous secreted immunoglobulin reactive to the second antigen. The exogenously incorporated membrane immunoglobulin acts as a receptor to a specified ligand, e.g., the first antigen. Binding of the first antigen to the exogenously incorporated membrane immunoglobulin controls signal transduction through the exogenously incorporated membrane immunoglobulin to control expression from the at least one endogenous secreted immunoglobulin reactive to the second antigen. Binding of the first antigen to the exogenously incorporated membrane immunoglobulin controls signal transduction through the membrane immunoglobulin to control activation of the B lymphocyte or differentiation of the B lymphocyte.

FIG. 1 is a schematic of a diagrammatic view of hypothetical immunoglobulin genes for memory B lymphocytes. Heavy (H) chain gene is on chromosome 14. Kappa (K) L chain gene is on chromosome 2. Lambda (λ) L chain gene is on chromosome 22. A functional allele and a nonfunctional allele are present on chromosomes 14 and 2. Both λ L chain alleles are depicted as nonfunctional. As shown in Example 3, the immunoglobulin genes encoding the H chain and L chain for an anti-PSA membrane antibody are cloned in targeting plasmid vectors to allow targeted integration in the corresponding nonfunctional Ig loci on chromosomes 14 and 2 respectively.

FIGS. 2A, 2B, and 2C are a schematic of a diagrammatic view of nonfunctional and functional immunoglobulin heavy chain genes on chromosomes 14. The genetic structure of maternal chromosome 14 germline configuration is shown in FIG. 2A. Exons for variable regions ($V_H$), D segments (D), J segments ($J_H$), IgM constant region ($C_H\mu$), secreted tailpiece (TP) and the μ membrane anchor (TM and Cyt) are shown in FIG. 2B. The genetic structure of paternal chromosome 14 functionally rearranged is shown with recombined V, D and J segments ($V_H D_1 J_2$) as shown in FIG. 2C. The genetic structure of secreted and membrane μ-H chains encoded and alternate polyadenylation sites are shown. Note that Ig gene structure is simplified with only one constant region ($C_H$) exon shown. Also promoter and enhancer sequences are omitted.

As shown in Example 3, the anti-PCLA immunoglobulin H and L chain genes are integrated into the Ig loci of the mature B cell which are functionally rearranged on chromosomes 14 and 2 respectively. See FIG. 2B for functionally rearranged H chain locus.

FIGS. 3A, 3B, and 3C are a schematic of a diagrammatic view of replacement of immunoglobulin genes with heavy chain genes engineered to express membrane IgG and secreted IgG. The genetic structure of secreted and membrane γ-H chain gene with alternate polyadenylation sites are shown in FIG. 3A. The genetic structure of maternal chromosome 14 with an engineered membrane γ-H chain gene is shown in FIG. 3B. The genetic structure of paternal chromosome 14 with an engineered secreted γ-H chain gene is shown in FIG. 3C. Note that Ig gene structure is simplified with only one constant region ($C_H$) exon shown. Also promoter and enhancer sequences are omitted.

As shown in Example 3, the anti-PCLA IgG H chain gene (i.e., γ-H chain gene) may be engineered to remove coding sequences for the membrane spanning domain (™) and the cytoplasmic amino acids (Cyt) to yield a γ-H chain gene encoding a secreted H chain only (FIG. 3C).

FIGS. 4A, 4B, 4C, 4D are a schematic of a diagrammatic view of protocols to produce recombinant B lymphocytes with membrane immunoglobulin to a first antigen and secreted immunoglobulin to a second antigen. FIG. 4A shows isolated memory B lymphocytes with endogenous DNA encoding anti-DNP membrane immunoglobulin and exogenous DNA encoding anti-Flu broadly neutralizing antibody (BNAb) secreted immunoglobulin. FIG. 4B shows isolated memory B lymphocytes with exogenous DNA encoding anti-DNP membrane immunoglobulin and exogenous DNA encoding anti-Flu broadly neutralizing antibody (BNAb) secreted immunoglobulin. FIG. 4C shows isolated memory B lymphocytes with endogenous DNA encoding anti-Flu Abs secreted immunoglobulin and exogenous DNA encoding anti-DNP membrane immunoglobulin. FIG. 4D shows isolated memory B lymphocytes with exogenous DNA encoding an anti-Flu BNAb secreted immunoglobulin and exogenous anti-DNP membrane immunoglobulin polypeptide delivered with liposomes.

FIG. 5 is a schematic of a diagrammatic view of a method 500 for producing at least one immunoglobulin in an isolated B lymphocyte cell line 501 that includes isolating 502 from a vertebrate subject immunized with at least one second antigen, a B lymphocyte cell expressing at least one endogenous secreted immunoglobulin reactive to the at least one second antigen; introducing 503 into the isolated B lymphocyte cell at least one exogenous membrane immunoglobulin reactive to at least one first antigen to produce a recombinant B lymphocyte cell line; expanding and selecting 504 the isolated B lymphocyte cell line expressing the membrane immunoglobulin reactive to the at least one first antigen and expressing the at least one endogenous secreted immunoglobulin reactive to the at least one second antigen.

FIG. 6 is a schematic of a diagrammatic view of a method 600 for producing at least one immunoglobulin in an isolated B lymphocyte cell line 601 that includes introducing 602 into at least one isolated B lymphocyte cell at least one exogenous membrane immunoglobulin reactive to at least one first antigen to produce at least one first isolated B lymphocyte cell line; expanding and selecting 603 the at least one first isolated B lymphocyte cell line expressing the membrane immunoglobulin reactive to the at least one first antigen; introducing 604 into the at least one first isolated B lymphocyte cell line at least one exogenous nucleic acid encoding one or more secreted immunoglobulins reactive to at least one second antigen to produce at least one isolated recombinant B lymphocyte cell line; and selecting 605 the at least one isolated recombinant B lymphocyte cell line expressing the one or more secreted immunoglobulin reactive to the at least one second antigen.

FIG. 7 is a schematic of a diagrammatic view of a method 700 for producing at least one immunoglobulin in a recombinant B lymphocyte cell line 701 that includes isolating 702 from a vertebrate subject immunized with at least one first antigen, a B lymphocyte cell expressing at least one endogenous membrane immunoglobulin reactive to the at least one first antigen; introducing 703 into the isolated B lymphocyte cell at least one exogenous nucleic acid encoding at least one of a secreted immunoglobulin reactive to at least one second antigen and expand the cell to produce a recombinant B lymphocyte cell line; and assaying 704 for presence of the at least one exogenous secreted immunoglobulin reactive to the at least one second antigen to select the recombinant B lymphocyte cell line.

FIG. 8A illustrates a recombinant B cell receptor protein 1000 with a single-chain variable fragment 1005 joined to IgG heavy chain domains that include a hinge segment 1008, joined to CH3 domain 1010, transmembrane 1015, and cytoplasmic 1020 domains attached to an IL-21 receptor cytoplasmic domain 1025.

Figure 8B:
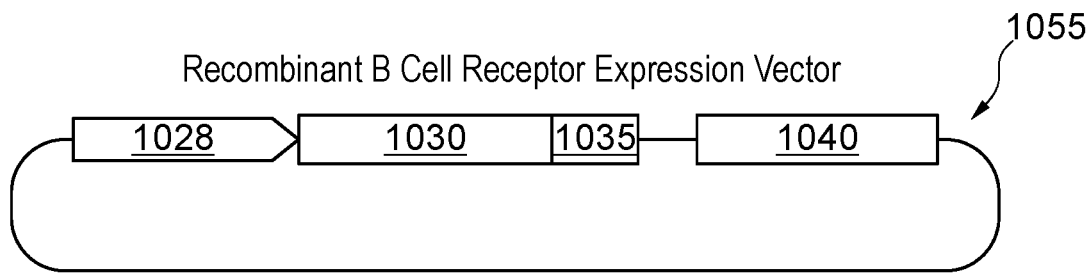
FIG. 8B is a schematic of a diagrammatic view of a recombinant B cell receptor expression vector.

FIG. 8B includes an illustration of a recombinant B cell receptor expression vector 1055 that includes a CMV promoter 1028 joined to a recombinant B cell receptor 1030 attached to a poly-A site 1035 and a neomycin resistance gene 1040.

Figure 8C:
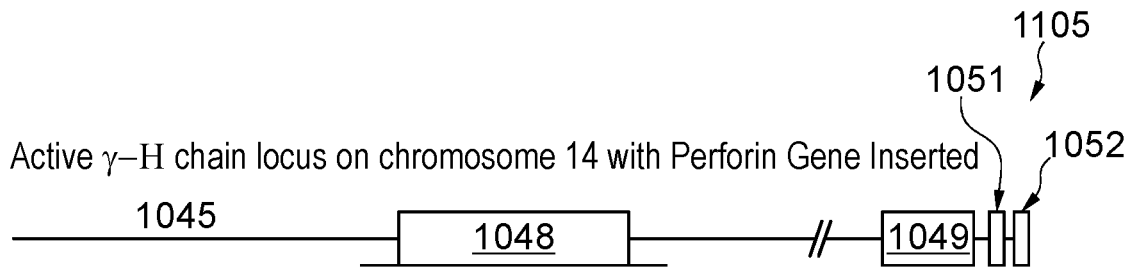
FIG. 8C is a schematic of a diagrammatic view of chromosome 14 with inserted gene.

FIG. 8C is an illustration of an active gamma heavy chain locus on chromosome 14 with perforin gene inserted 1105, including an Ig variable gene promoter 1045 joined to perforin cDNA 1048 and downstream an Ig alpha constant region 1049, with transmembrane domain 1051 and cytoplasmic domain 1052.

Figure 8D:
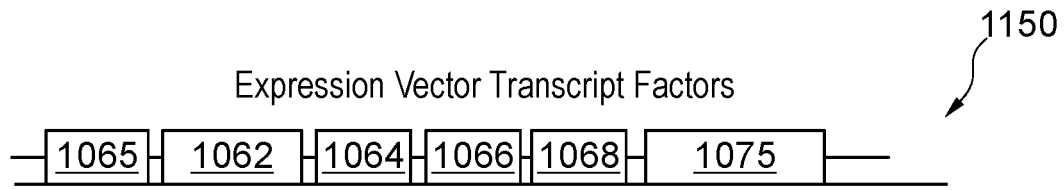
FIG. 8D is a schematic of a diagrammatic view of an expression vector with transcription factors.

FIG. 8D includes an illustration of a Sendai virus expression vector with transcription factor genes inserted 1150 including a viral NP gene 1065 joined to a viral P/V gene 1062, with three transcription factors T-bet 1064, RunX3 1066, and Eomes 1068 with the viral L gene 1075 at the 3-prime end.

Figure 9A:
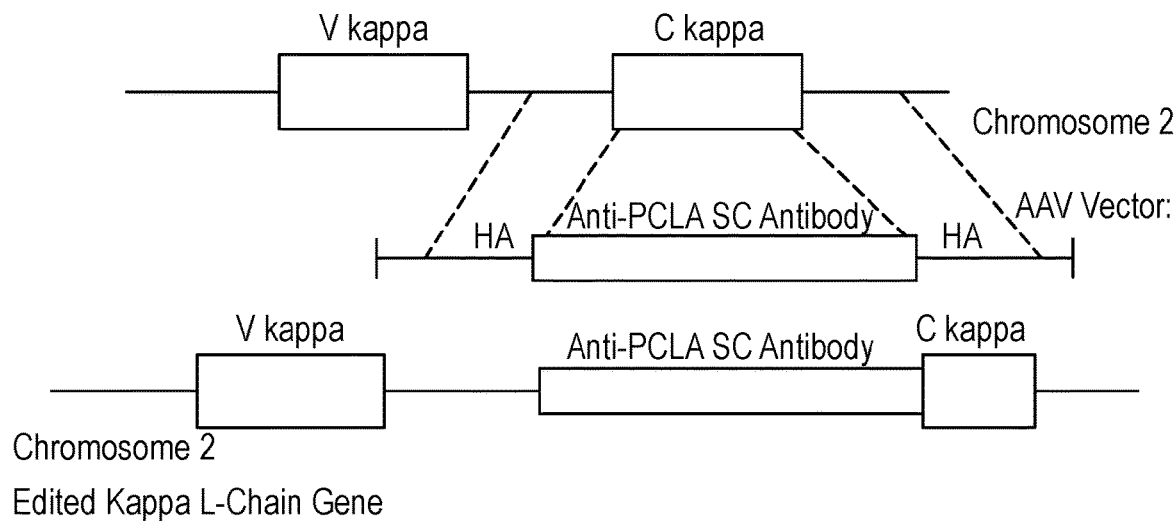
FIG. 9A is a schematic of a diagrammatic view of an example of integration of a desired expression construct at an endogenous site (light chain Ig).

FIG. 9A illustrates the integration of a single chain (SC) antibody gene at the active, rearranged kappa light chain locus on human chromosome 2. An adenovirus-associated viral (AAV) vector bearing the gene for an anti-prostate cancer lipid antigen (PCLA) SC antibody flanked by homology arms (HA) that target integration to the kappa constant region gene (C kappa). The results of CRISPR-mediated integration of the anti-PCLA SC Antibody gene in the Ckappa gene on chromosome 2 are shown.

Figure 9B:
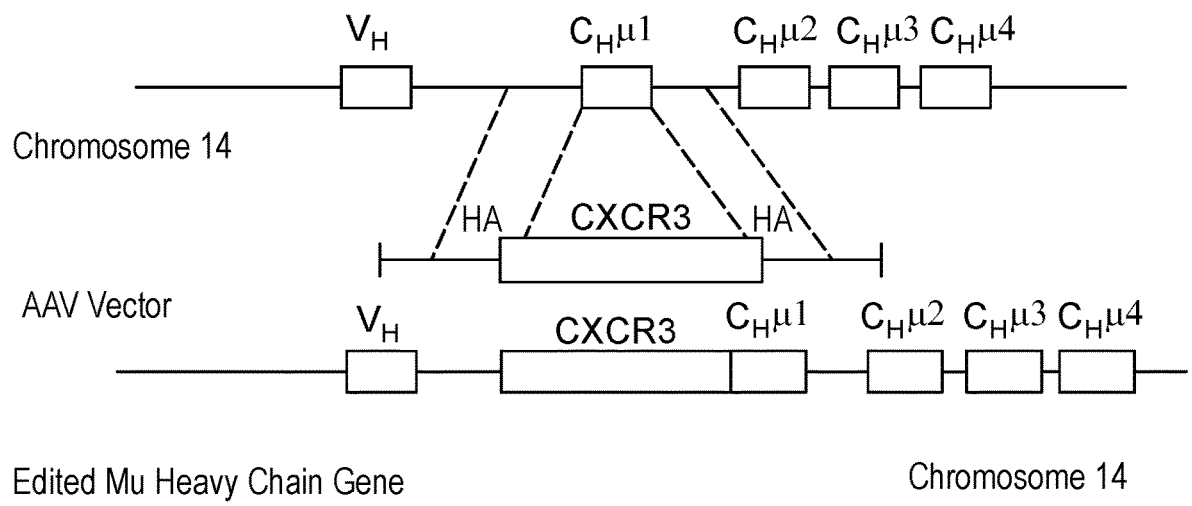
FIG. 9B is a schematic of a diagrammatic view of an example of integration of a desired expression construct at an endogenous site (heavy chain Ig).

FIG. 9B shows the targeted integration of a chemokine receptor gene (CXCR3) at the active, rearranged immunoglobulin (Ig) mu heavy-chain locus. An AAV vector bearing the gene for CXCR3 flanked by HA that target integration to the first exon ($C_H1$) of the Ig mu constant region gene. The edited Ig mu heavy chain gene on chromosome 14 is shown.

Figure 10:
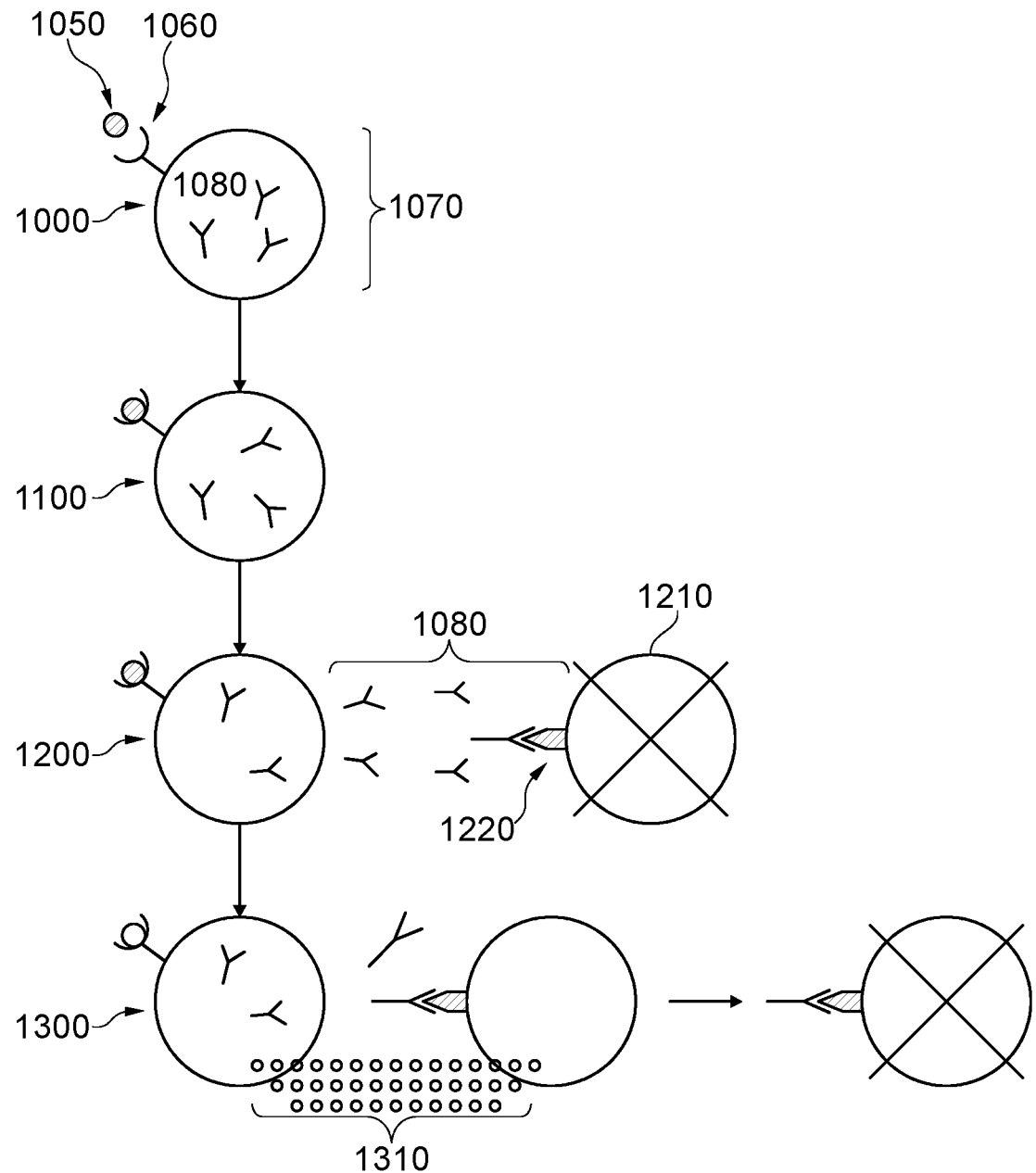
FIG. 10 is a schematic of a diagrammatic view of a modified B cell engineered to selectively engage a surface immunoglobulin with a first target antigen and subsequently secrete a predetermined antibody to a second target antigen with optional secretion of a reassigned biological agent and/or cytotoxic effector molecule(s).

FIG. 10 illustrates a method 1000 of activating the modified B cell 1070 engineered with a predetermined exogenous or endogenous membrane immunoglobulin 1060 to selectively engage a first target antigen 1050 and subsequently secrete a predetermined antibody 1080 to a second target antigen 1220 and/or secrete a reassigned biological agent and/or cytotoxic effector molecule(s) (1310) resulting in the death of target cell(s) 1210.

Referring to FIG. 10, the modified B cell includes engaging or allowing to engage 1100 an antigen (either engineered or naturally occurring) with the predetermined surface immunoglobulin 1060. In the next step 1200, receptor engagement 1100 leads to secretion of the predetermined (exogenously or endogenously incorporated) antibody 1080 configured to engage with the second target antigen 1220 on the target cell 1210. Finally, the next step 1300 includes the optional secretion of one or more cytotoxic molecules (which may be reassigned biological agents) 1310 for additional target cell destruction.

Figure 11:
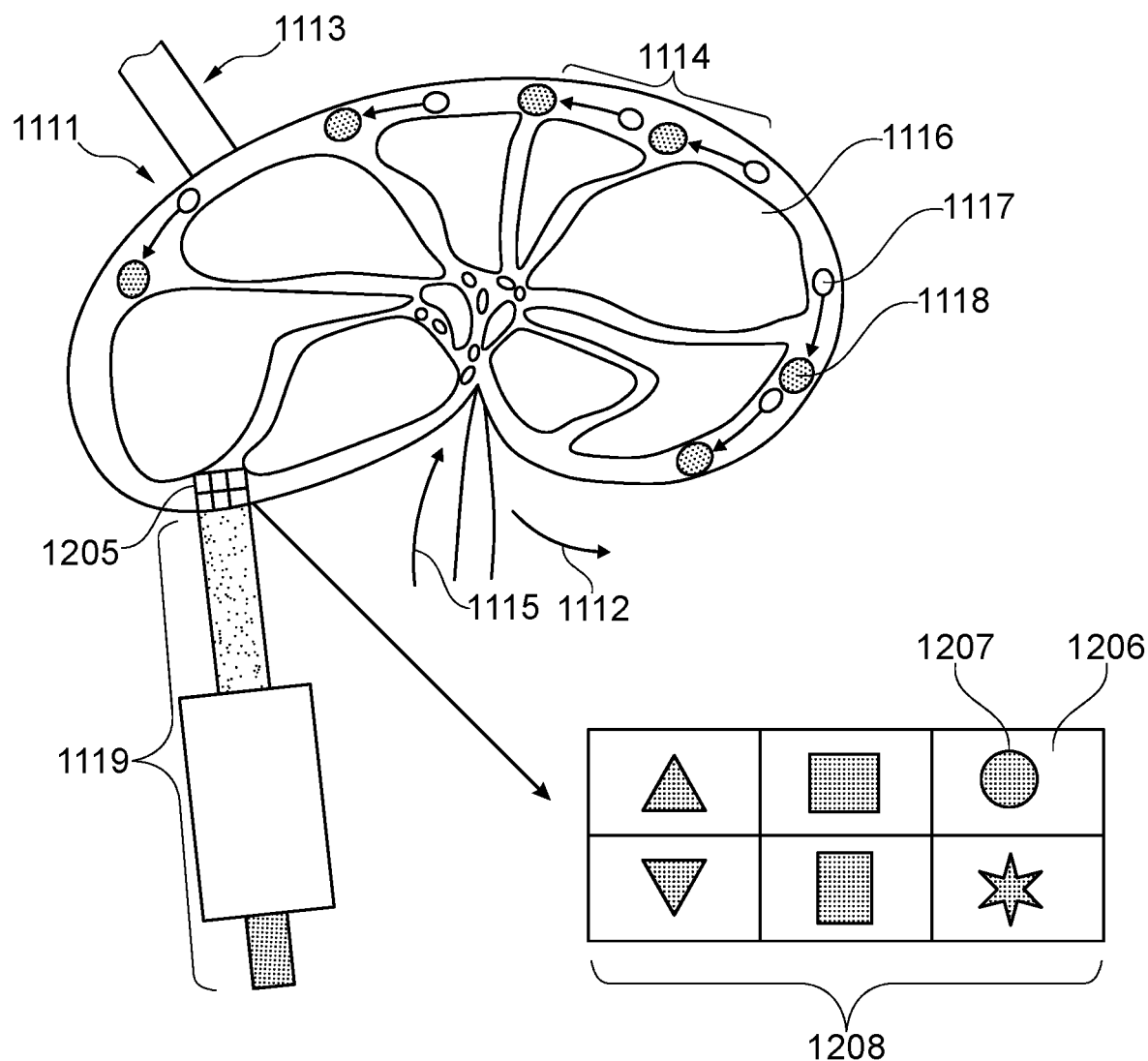
FIG. 11 is a schematic of a diagrammatic view of a lymph node with modified B cells having reactivity to selective antigens, as determined by the particular modification(s) of the B cells.

FIG. 11 illustrates a lymph node 1111 with modified B cells 1117 that recognize particular target antigens 1118 that contribute to activation of the modified B cells. As can be seen in the illustration, the medulla 1115 is rich in macrophages and plasma cells, while the cortex 1114 contains mostly inactivated B and T cells, as well as dendritic cells and macrophages. In an embodiment, the modified B cells are implanted into the lymph node 1111 for example, in the cortical area 1114 to be activated, or even if they are already activated. As illustrated in FIG. 11, the afferent lymph vessel 1113 and efferent lymph vessel 1112 brings immune system cells into and out of the lymph node 1111. In FIG. 11, the germinal centers 1116 include locations for mature B cells to proliferate, differentiate, and generate antibody. In an embodiment, the modified B cells can be implanted into one or more germinal centers 1116 of the subject's lymph node 1111.

In an embodiment, a B cell stimulation device 1205 can be implanted, for example in the cortical area or capsular space of the lymph node 1111. The B cell stimulation device 1205 can include an array of wells 1208 which can include, for example, different antigens and/or different concentrations of antigens and/or different adjuvants and/or different concentrations of adjuvants. For example, in one particular well 1206, a predetermined antigen 1207 (optionally with adjuvant) is remotely triggered to be released in the lymph node and eventually the predetermined antigen 1118 reaches the modified B cells 1117 for engagement. Such engagement can include priming (or being a "booster") of the modified B cells, or can be an initial activation of the modified B cells, or if desired, can be a tolerizing of the modified B cells (for example, with "self-antigen" related to an autoimmune disease). As illustrated in FIG. 11, the B cell stimulation device 1205 can include remotely triggering different antigens and/or concentrations over time 1119 and can act on naturally occurring B cells as well as modified B cells described herein. For example, over time 1119 the B cell stimulation device 1205 can release three different concentrations and/or antigens into the blood stream or lymph node.

Figure 12A:
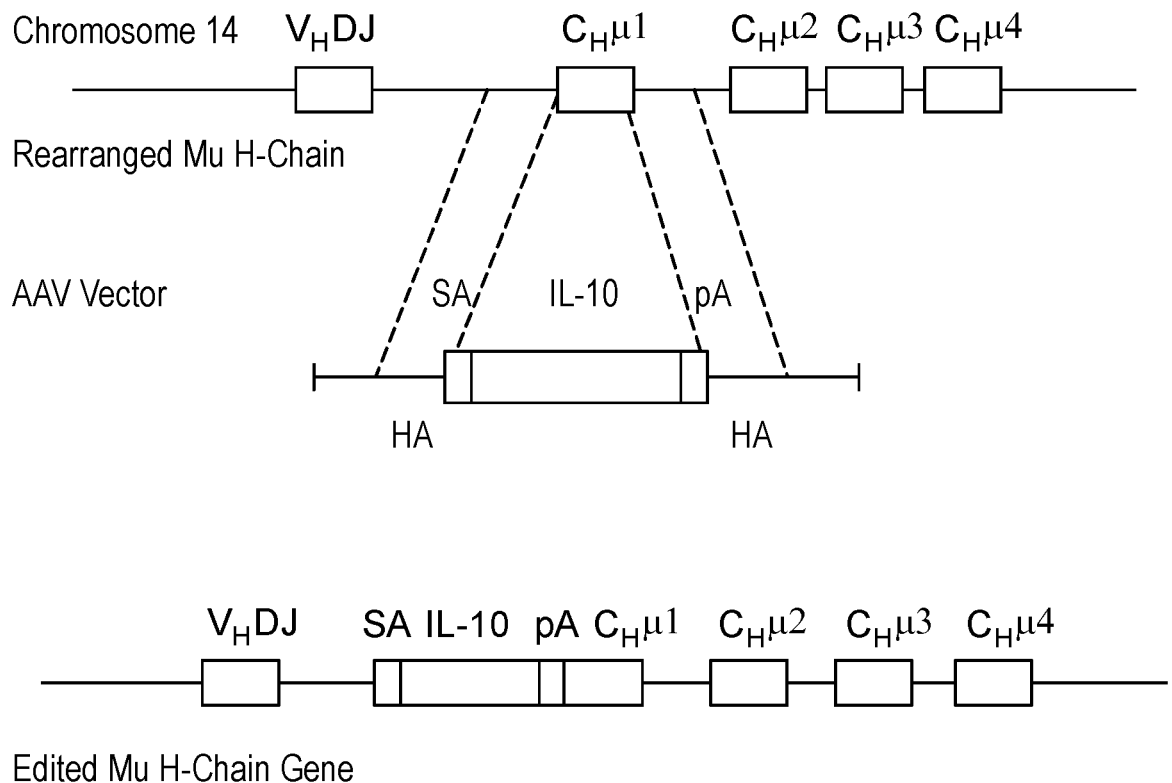
FIG. 12A is a schematic of a diagrammatic view of an example of integration of a desired expression construct at an endogenous site (Heavy Chain Ig).

FIG. 12A illustrates insertion of a gene for interleukin 10 (IL-10) at the first exon of the active, rearranged Ig heavy chain gene on chromosome 14. A rearranged Ig mu heavy chain gene with a variable region ($V_H$DJ) exon, an intron and mu constant region ($C_H\mu$) exons is shown. An AAV vector encoding an interleukin 10 (IL-10) gene is shown with a splice acceptor site (SA), a poly A addition site (pA) and flanking homology arms (HA) to target integration at the mu heavy chain gene. The edited Ig mu heavy chain gene is shown with the IL-10 gene positioned downstream of the variable region and interrupting the mu constant region gene.

Figure 12B:
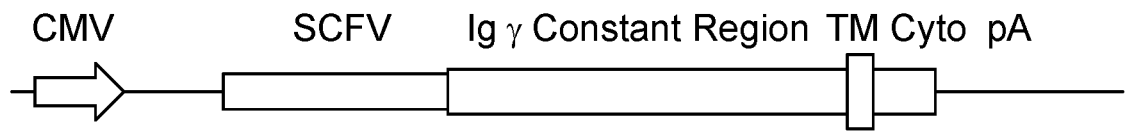
FIG. 12B is a schematic of a diagrammatic view of an example of an expression vector for use in modifying B cells as described herein.

FIG. 12B shows a lentiviral expression vector encoding a single chain membrane antibody specific for an autoantigen, myelin oligodendrocyte glycoprotein (MOG). The vector contains a cytomegalovirus promoter element (CMV) directing transcription of the single chain antibody. The single chain antibody includes a single chain Fv (SCFV) segment fused to an Ig gamma constant region gene.

Figure 13:
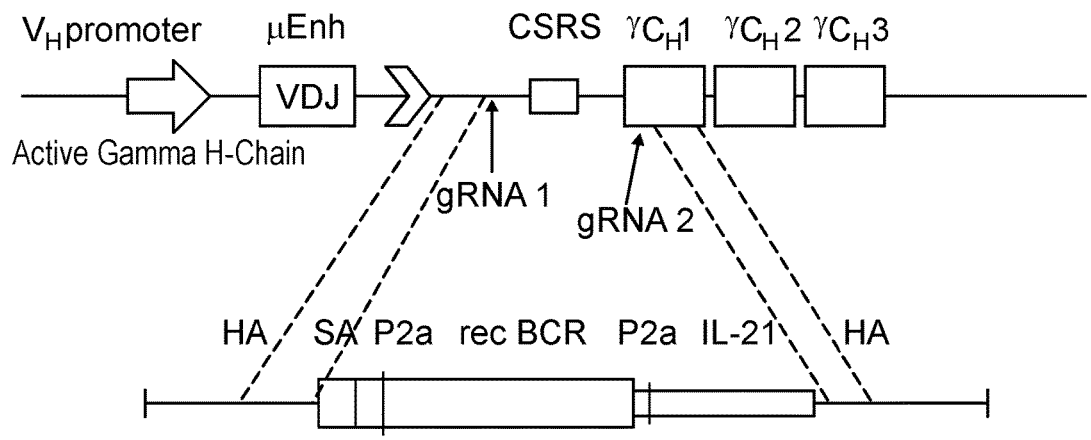
FIG. 13 is a schematic of a diagrammatic view of an example of an integration of a desired bicistronic expression construct at an endogenous site (Heavy Chain Ig).
Figure 13:
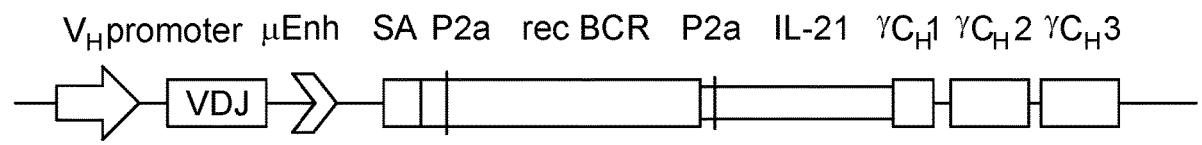

FIG. 13 illustrates integration of a bicistronic construct downstream (3') of the $V_H$ promoter and mu enhancer (µEnh) leading to disruption of the active rearranged Ig gamma heavy chain gene on chromosome 14. The location of guide RNAs (gRNA) to target CRISPR-mediated integration in the intron and γCH1 exon of the gamma heavy chain gene are indicated. The class switch recombination site (CSRS) is indicated. An AAV vector encoding a bicistronic construct is illustrated. The bicistronic construct includes genes for a recombinant B cell receptor (recBCR) and interleukin 21 (IL-21) with self-cleaving peptides (P2a) encoded before each gene. The edited gamma heavy chain gene is shown with the bicistronic construct expressed under the control of the $V_H$ promoter and mu enhancer. Expression of the gamma H-chain gene is disrupted by the bicistronic construct.

In a method for treating a disease in a vertebrate subject with an immunotherapeutic product, the recombinant B lymphocyte cell line may be autologous to one of the one or more vertebrate subjects. Alternatively, in a method for treating a disease in a vertebrate subject with an immunotherapeutic product the recombinant B lymphocyte cell line may be allogeneic to one of the one or more vertebrate subjects. In the case where the recombinant B lymphocyte cell line is allogeneic to one of the one or more vertebrate subjects. In each case when necessary, the recombinant B lymphocyte cell line can be modified to reduce or eliminate expression of MHC Class I (MHC I) proteins or mismatched HLA antigens in the recombinant B lymphocyte cell line to avoid allograft rejection and to reduce or eliminate a graft versus host disease in the recipient of the allogeneic recombinant B lymphocyte cells. See, e.g., U.S. application Ser. No. 12/804,650, and U.S. application Ser. No. 12/804,647, which are incorporated herein by reference.

A vertebrate subject is treated with unmatched, allogeneic donor recombinant B lymphocyte cells engineered to block the presentation of Major Histocompatibility Class I (MHC I) proteins on their cell surface. Allogeneic donor recombinant B lymphocyte cells are transfected with a lentiviral expression vector that directs the expression of a microRNA (miRNA) that inhibits beta2-microglobulin ($\beta$2M) protein translation and blocks MHC I assembly and presentation on the cell surface. The genetically engineered recombinant B lymphocyte cells are injected into the patient. The inhibition of MHC I production in engrafted recombinant B lymphocyte cells is controlled by a regulatory module and an effector molecule, doxycycline. In the event that the recombinant B lymphocyte cells must be eradicated, doxycycline is administered to repress expression of the miRNA, thereby allowing expression of $\beta$2M and MHC I on the cell surface and evoking an alloreactive immune response.

A vertebrate subject is treated with recombinant B lymphocyte cells that have reduced expression of Major Histocompatibility Class I (MHC I) proteins on their cell surface, in order to avoid immune rejection of the transplanted cells. The engineered recombinant B lymphocyte cells also contain a suicide mechanism that can be activated by the administration of a prodrug, ganciclovir, in the event of uncontrolled proliferation or other adverse events associated with the recombinant B lymphocyte cells.

A vertebrate subject is treated with a recombinant B lymphocyte cells that are modified to reduce their expression of mismatched HLA antigens and thus avoid allograft rejection. Recombinant B lymphocyte cells are infected with a lentivirus vector encoding microRNA (miRNA) that inhibits the expression of specific donor HLA alleles not shared by the recipient. Production of mismatched HLA-A, -B, -C, -DRBI, and -DQB1 alleles are blocked by miRNAs, and the corresponding HLA proteins are not expressed by the modified donor recombinant B lymphocyte cells.

A vertebrate subject is treated by transplantation with recombinant B lymphocyte cells. Allogeneic recombinant B lymphocyte cells are modified to reduce expression of MHC Class I (MHC I) proteins by expression of a viral gene that targets MHC I proteins for destruction. Recombinant B lymphocyte cells are transduced with a lentiviral expression vector encoding cytomegalovirus (CMV) protein, unique sequence 11 (US11), to target MHC I proteins for destruction and avoid allograft rejection (see e.g., Lin et al., *Cellular and Molecular Immunology* 4: 91-98, (2007), which is incorporated herein by reference).

In addition to secreting antibodies, as described herein, in an embodiment the one or more modified B lymphocyte cells have been engineered to secrete a non-antibody protein (e.g., glycoprotein, proteoglycan, amino acid, etc.) when prompted by engagement with the surface immunoglobulin with a specifically designed "trigger" antigen. For example, the non-antibody protein may include a neurotransmitter, hormone, cytokine, fat, vitamin, mineral, or anti-inflammatory agent.

In an embodiment, one or more neurotransmitters, such as dopamine, serotonin, acetylcholine, GABA, norepinephrine, oxytocin, etc., are secreted by the modified B lymphocyte cells.

In an embodiment, one or more neurotransmitters are secreted by one or more modified B lymphocyte cells upon ingestion, injection, implantation, or otherwise a transfer of the modified B lymphocytes to a subject. For example, it has been documented that naturally occurring B lymphocytes will home to Peyer's patches and other areas of the gastrointestinal tract upon oral ingestion (e.g., by way of breastmilk). See, for example, Cabinian et al, PLOS One. 2016; 11(6): e0156762, which is incorporated herein by reference.

Furthermore, it is known that the microbiome plays a role in cancer development, progression, and therapy. See, for example, Bhatt et al, CA Cancer J Clin 2017; 67:326-344, which is incorporated herein by reference.

Thus, in an embodiment, an oral or other formulation of a composition including one or more modified B lymphocytes as described herein can be provided to a subject for treatment of a disease or indication. In an embodiment, a composition can be delivered in another route, for example as an intramuscular injection, subcutaneous injection, sublingual administration, buccal administration, parenteral administration, anal administration, intralymphatic administration, or another route of administration that is sufficient to provide delivery of the composition to the subject for treatment.

In an embodiment, an oral or other formulations of composition including one or more modified B lymphocytes further includes one or more life, dead, or preserved strains of microorganism, such as *E. coli, Bacteroides, Bifidobacterium, Bacillus, Saccharomyces, Prevotella* tanneraie, *Neisseria lactamica, Streptococcus, Staphylococcus, Serratia, Corynebacteria, Lactobacillus*, or others. For example, in an embodiment, strains such as *L. acidophilus, B. longum, B. bifidum, B. lactis, B. infantis, B. animalis, L. rhamnosus, L. fermentum, L. plantarum, L. brevis, L. salivarius, L. paracasei, L. gasseri, L. reuteri, B. coagulans, S. salivarius*, etc.

In an embodiment, the modified B cells provide surveillance in the subject's body, such that the cells are directed to secrete a specific antigen when the cell's surface immunoglobulin receptor is triggered with the antigen selected for in the process of engineering the cells.

In order to selectively stimulate and re-stimulate the modified B cells, a particular antigen (e.g., DNP-KLH) is administered in the absence of adjuvant. The endogenous response of these modified B cells should be limited to stimulation without over-stimulation that could result in tolerance to the antigen rather than antibody secretion reaction. Further, a DNP conjugate of a peptide from KLH would likely elicit a restricted endogenous response.

In an embodiment, the modified B cells are stimulated or restimulated to use an alternate carrier (e.g., DNP-Human Serum Albumin) which should not elicit an immune response but will provide a "booster" antigen stimulation to the modified B cells.

In an embodiment, a B cell stimulation device is implanted in or on the subject in order to provide stimulation or re-stimulation of the modified B cells (or of a patient's own innate B cells). For example, the B cell stimulation device can include a microarray or microchip device with antigen (and optionally adjuvant, cytokines, chemokines, etc.) on or in the device and can be injected into a subject such that activating the antigen-carrying device allows for release of the antigen and/or adjuvant for "boosting" the activation of the modified B cells.

For example, a microchip containing one or more small, hermetically sealed compartments can be activated by remote control (eg wireless signal) to trigger the release of one or more compartments. In an embodiment, the one or more compartments can be triggered to release the antigen and/or adjuvant and/or other molecules (eg cytokines, chemokines, growth factors, etc.) based on a pre-programmed dosing schedule. In an embodiment, the one or more compartments can be triggered as desired. In an embodiment, the subject can control the trigger for the B cell stimulation device. In an embodiment another entity can control the trigger for the subject's B cell stimulation device. In an embodiment, the B cell stimulation device is placed in lymphatic tissue of a subject, including but not limited to, for example, lymph nodes, GALT, MALT, spleen, liver, etc. See FIG. 11.

In an embodiment, the B cell stimulation device can be easily implanted and/or removed in a healthcare setting. In an embodiment, the B cell stimulation device can include at least ten, at least twenty, at least fifty, at least one hundred, at least two hundred, or more doses for stimulating B cells. In an embodiment, each dose is the same in a particular B cell stimulation device. In an embodiment, multiple different doses include different contents (eg different antigen and/or different adjuvant). In an embodiment, the compartments of the B cell stimulation device is configured such that each dose can be released at a specific time (eg by predetermined program, by way of sensors detecting a specific physiological parameter that causes or warrants release of a dose, or by active intervention by the subject or another entity such as a healthcare worker or computing device).

In an embodiment, the B cell stimulation device includes multiple different antigens and/or multiple different adjuvants and/or cytokines or other molecules such as ligands or transcription factors (configured as each in its own compartment or a mix of two or more in a single compartment) and can be wirelessly released into the subject's body. In an embodiment, each compartment is independently addressable and independently activatable in any desired sequence of release. In an embodiment, the B cell stimulation device includes electronic circuitry including wireless communications (eg radio frequency), circuitry in electronic communication with each compartment for independent release of its contents, timer or clock for accurate interval spacing and/or release of contents of a compartment, and a controller in electronic communication with the various electrical components for proper functioning.

For example, a wirelessly controlled implantable microchip-based drug delivery device for delivering human parathyroid hormone fragment has been successfully tested in clinical trials in humans as a bioequivalent to daily injections. See, for example, Farra, *Science Translational Med* 22 Feb. 2012, Vol. 4, Issue 122, pp. 122ra21, which is incorporated herein by reference.

In an embodiment, a B cell stimulation device similar to the microchip device described in the citation above is configured for stimulating B cells in a subject, including the modified B cells described herein throughout. For example, a microchip array device with discrete compartments with an impermeable, thin metallic membrane is configured to retain the contents in a lyophilized form or other activatable form. For example, the metallic membrane can be removed by electrothermal ablation, which releases the contents of the compartment in a controlled manner.

In an embodiment, a B cell stimulation device is inserted subcutaneously into a subject that has already received or will receive modified B cells as described herein. In an embodiment, the B cell stimulation device is implanted into a lymphoid tissue of a subject that has already received or will receive modified B cells as described. Lymphoid tissue can include, for example, lymph nodes, tonsils, spleen, Peyer's patches, mucosa associated lymphoid tissue, bone marrow, or thymus.

In an embodiment, a B cell stimulation device can be approximately 50 mm×30 mm×10 mm (l×w×h), as described in Farra herein above, with two microchips with 10 reservoirs each. In an embodiment, the stimulation device can be approximately half this size, with a single microchip with 10 reservoirs each. In an embodiment, the stimulation device can be much smaller, for example, a single microchip with 1, 2, 3, 4, 5, 6, 7, 8, or 9 reservoirs.

In an embodiment, the B cell stimulation device includes at least one compartment with an enzyme, such as collagenase, to assist with penetration of the fibrous membrane capsule that can form around any implant in a subject's body. Typically, the fibrous tissue capsule is less than one mm thick and allows for passage of molecules through it. Id. However, if additional penetration is needed, enzymatic release prior to release of B cell stimulants can be performed. In this way, one or more compartments containing collagenase or other enzymes are released prior to release of the B cell stimulants (eg antigen, adjuvant, cytokine, other immune stimulant, etc.).

In a report of a patient who underwent CAR-T cell immunotherapy, it was noted that the patient attained complete remission of brain metastases, and upon physical biopsy of a recurrent, subcutaneous lesion, the CAR-T cells became activated or re-activated with the result that the subcutaneous tumor also regressed. See Science News, Aug. 28, 2017, online report from Massachusetts General Hospital, which is incorporated herein by reference. In an embodiment, the modified B cells described herein are stimulated or re-stimulated by physical biopsy sampling of suspected tumor tissue, or lymph node.

PROPHETIC EXAMPLES

Example 1

Recombinant Memory B Lymphocytes that Express Two Different Antibodies: 1) a B Cell Receptor (BCR) that Recognizes a Model Antigen, Dinitrophenol-Keyhole Limpet Hemocyanin (DNP-KLH), and 2) a Secreted Antibody that Neutralizes Multiple Strains of Influenza Virus An isolated recombinant B lymphocyte cell line that produces a secreted broadly neutralizing immunoglobulin to influenza virus and produces a membrane immunoglobulin to a model antigen can be utilized for cell therapy in a mammalian subject. The recombinant B lymphocyte cell line can be injected into the mammalian subject as cell therapy to provide immunological protection from infection by influenza virus. The recombinant B lymphocyte cell line can be activated in vivo or ex vivo to produce the broadly neutralizing influenza antibody by injecting the mammalian subject (or an in vitro cell culture) with model antigen, dinitrophenol-keyhole limpet hemocyanin (DNP-KLM). The timing to stimulate immunological protection from influenza virus infection in the mammalian subject can be chosen based upon the timing of an outbreak of influenza infection in the population at large.

An individual is immunized with a model antigen, dinitrophenol (DNP), to elicit memory B cells with B cell receptors (BCR) specific for the DNP model antigen. Memory B cells develop in response to immunization with DNP conjugated to a carrier protein, keyhole limpet hemocyanin (KLH). A primary immunization with 1 mg of DNP-KLH (see e.g., Biosearch Technologies DNP-KLH Product Info Sheet which is incorporated herein by reference) is injected subcutaneously in the right arm. See e.g., Rentenaar et al., *Kidney International* 62: 319-328, 2002 which is incorporated herein by reference. Approximately 12-14 days after immunization memory B cells expressing BCR specific for DNP are isolated using dinitrophenol-human serum albumin-biotin (DNP-HSA-biotin) and phycoerythrin-streptavidin (available from Biosearch Technologies, Novato, CA) and a fluorescein-anti-CD27 antibody to identify memory B cells. DNP-specific memory B cells are isolated by cell sorting with a fluorescence activated cell sorter (e.g., FACSAriaIII® available from Becton Dickinson, Franklin Lakes, NJ). For example, see U.S. Pat. No. 7,378,276 issued to Ettinger et al. on May 27, 2008 and U.S. Pat. No. 7,993,864 issued to Brown et al. on Aug. 9, 2011 which are incorporated herein by reference.

Memory B cells expressing BCRs that binds DNP are genetically engineered to express a secreted antibody which is a broadly neutralizing antibody reactive with multiple strains of influenza. Memory B cells expressing anti-DNP BCRs, containing membrane IgG antibodies, have a productively rearranged and expressed membrane immunoglobulin heavy (H) chain gene which resides on chromosome 14 (one of two parental chromosome 14 copies). However, the other parental chromosome 14 has an immunoglobulin (Ig) H chain gene that is not productively rearranged and not expressed. See FIGS. 1, 2A and 2B. This phenomenon, termed "allelic exclusion", yields individual B cells which express only one Ig heavy chain (and one Ig light (L) chain) and thus only one antibody (see e.g., Abbas et al., *Cellular and Molecular Immunology*, 7$^{th}$ Ed., Elsevier Saunders, Philadelphia, PA, 2012 which is incorporated herein by reference). To create B cells producing two different antibodies the memory B cells expressing anti-DNP BCRs are modified by replacing the non-functional, non-expressed immunoglobulin genes with functional, expressed immunoglobulin genes (for H and L chain). For example, the replacement immunoglobulin genes may encode a secreted antibody, which is a broadly neutralizing anti-influenza antibody.

In an embodiment, the IgH chain or IgL chain chromosomal loci are non-expressed Ig alleles where, for example, the endogenous rearranged $V_H$ promoter proximal to the mu enhancer is utilized for expression (due to V-J joining, the non-expressed allele will likely not have a $V_H$ promoter proximal to the Constant region).

The immunoglobulin genes encoding a broadly neutralizing antibody reactive with multiple strains of influenza virus may be isolated from the chromosomal DNA of a human B cell clone that produces the antibody. For example human B cells isolated from an individual who is immune to influenza virus infection are immortalized by infecting the isolated B cells with Epstein Barr virus (EBV). Supernatants derived from individual EBV-transformed B cell clones are tested in an immunoassay for antibodies that recognize influenza virus. Methods to immortalize B cells and to detect anti-viral antibodies are described (see e.g., Zhang et al., *Proc. Natl. Acad. Sci. USA* 107: 732-737, 2010 and Corti et al., *J. Clin. Investigation* 120: 1663-1673, 2010 which are incorporated herein by reference).

Methods to clone Ig heavy (H) chain and light (L) chain genes may be used. See e.g., U.S. Pat. No. 7,741,077 issued to Grawunder et al. on Jun. 22, 2010 and Early et al., *Proc. Natl. Acad. Sci. USA* 76: 857-861,1979 which are incorporated herein by reference. For example, an EBV-transformed B cell line expressing a human anti-influenza antibody, IgG$_1$(kappa), is grown in culture and used as a source to isolate messenger RNA (mRNA) and genomic DNA using standard methods employing phenol/chloroform. See e.g., Sambrook et al., In: *Molecular Cloning: A Laboratory Manual*, 2$^{nd}$ Ed., Cold Spring Harbor Press, Cold Spring Harbor, N.Y., 1989. The mRNA encoding the IgG, H chain and the kappa L chain are molecularly cloned following amplification using the polymerase chain reaction (PCR) and reverse transcriptase (RT). Methods and Ig gene primers to amplify Ig H chain mRNA and Ig L chain mRNA are described in U.S. Pat. No. 7,741,077 *Ibid*. The H and L chain mRNA (amplified as complementary DNA) are cloned in a plasmid vector (e.g., pCR®2.1-TOPO plasmid available from Invitrogen Corp., Carlsbad, CA). The DNA sequence of the Ig H chain variable (V) region (including the Vh, D and J segments) and the kappa L chain V-region (including the Vk and Jk segments) are determined. The V-region DNA sequences may be determined by automated DNA sequencing (DNA sequencing services are available from Charles River Laboratories International, Inc., Wilmington, MA).

To isolate the corresponding genomic Ig genes, the genomic DNA isolated from the anti-influenza B cell line (see above) is used as a template for PCR amplification of the human H chain gene and kappa L chain gene. PCR primers (oligonucleotides) to amplify the V-region genes, (including their respective promoters and flanking regions upstream (i.e., 5' of the V genes) are determined by searching a human genome database with the V-region DNA sequences established from the cloned Ig mRNA. For example, a human genome nucleotide database available from the National Center for Biotechnology Information can be searched with a computer program, BLAST, for sequences matching the H- and L-chain V-regions. A Human RefSeq Genome database and BLAST software are available online (see e.g., the world wide web at blast.ncbi.nlm.nih.gov/Blast.cgi). Primers to amplify the Ig constant regions, enhancer sequences, the H-chain membrane anchors, poly A addition sites and downstream flanking regions (i.e., 3' of the Ig genes) are described (see e.g., U.S. Pat. No. 7,741,077 *Ibid*.). The PCR-amplified, genomic fragments can be cloned in a plasmid vector such as pCR®2.1-TOPO available from Invitrogen Corp., Carlsbad, CA).

Figure 3A:
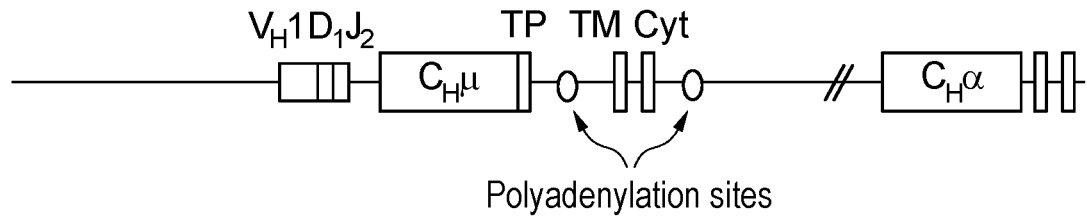
FIGS. 3A, 3B, 3C are a schematic of a diagrammatic view of replacement at immunoglobulin loci with heavy chain genes to express membrane IgG and secreted IgG.
Figure 3B:
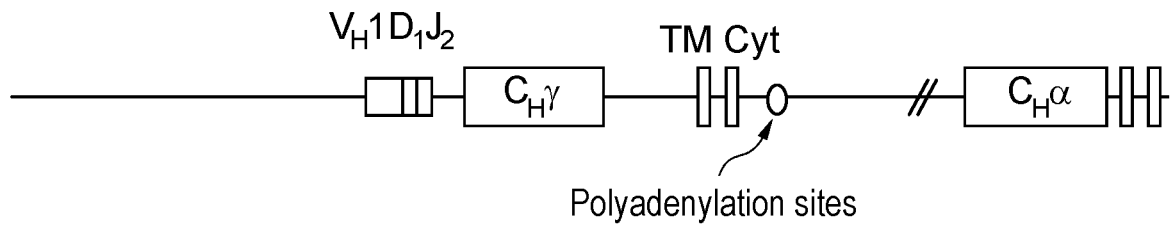
Figure 3C:
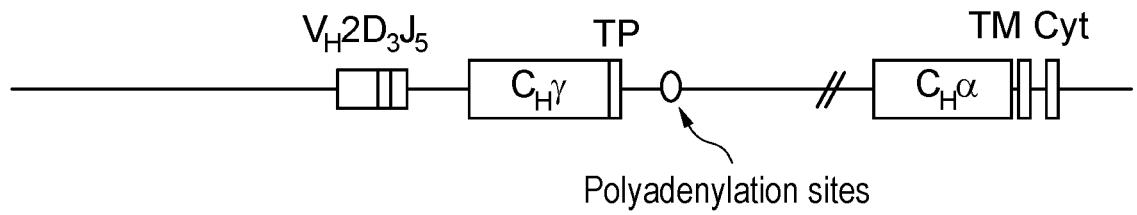
Figure 4A:
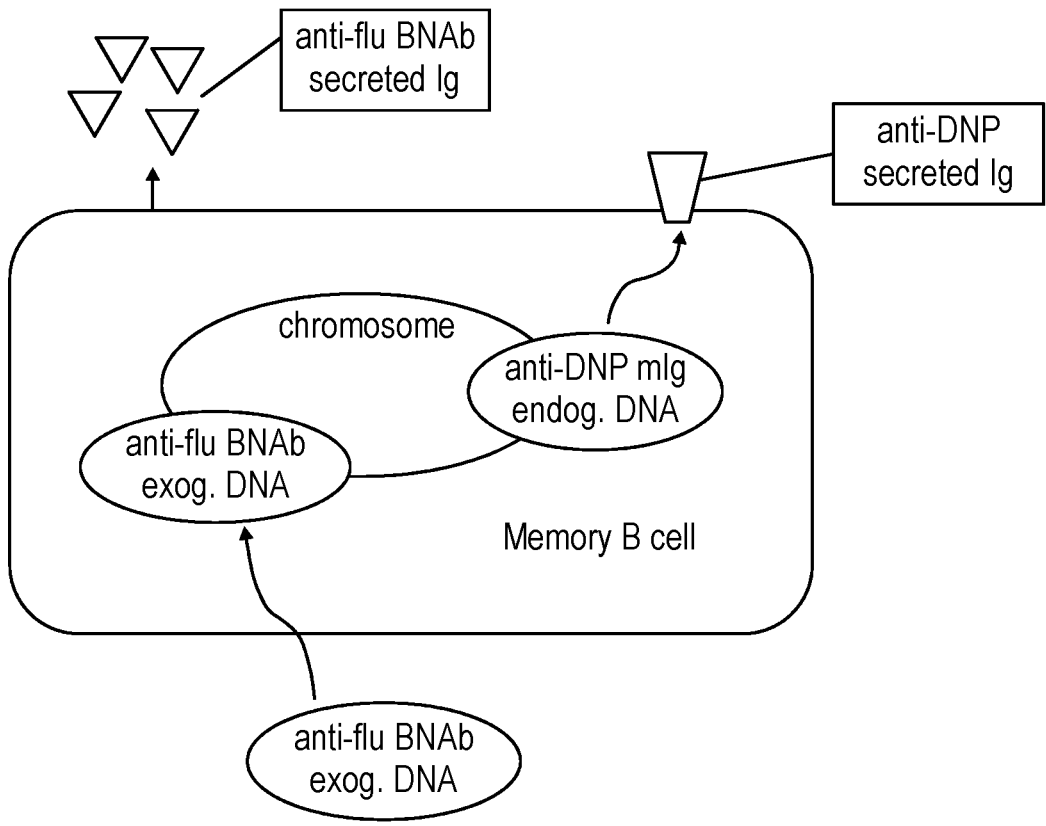
FIGS. 4A, 4B, 4C, 4D are a schematic of a diagrammatic view of protocols to produce recombinant B lymphocytes with membrane immunoglobulin to a first antigen and secreted immunoglobulin to a second antigen.
Figure 4B:
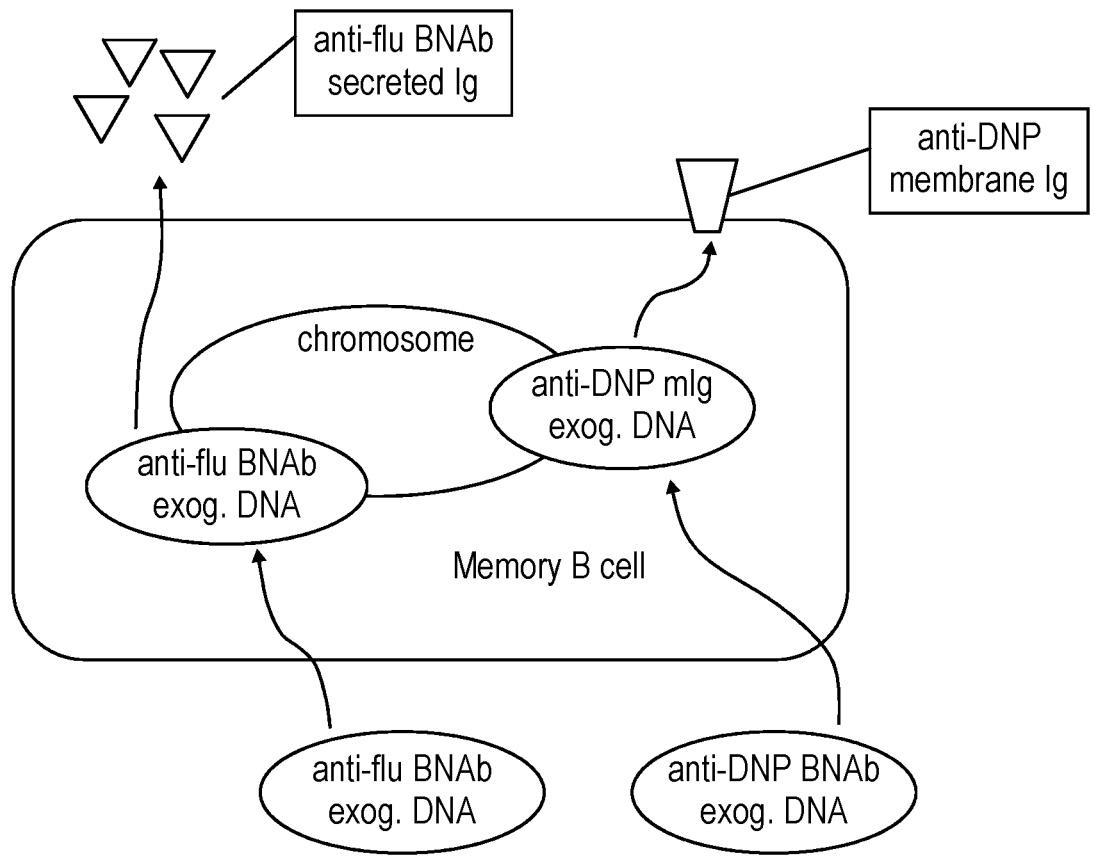
Figure 4C:
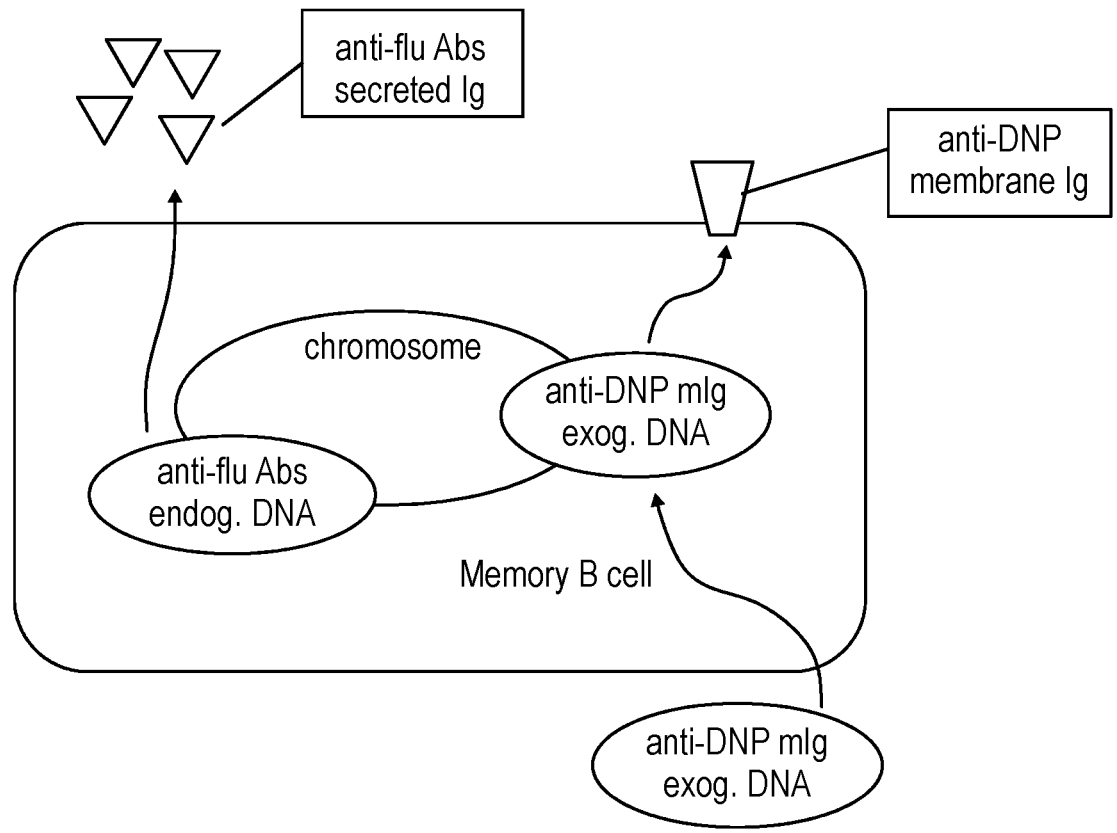
Figure 4D:
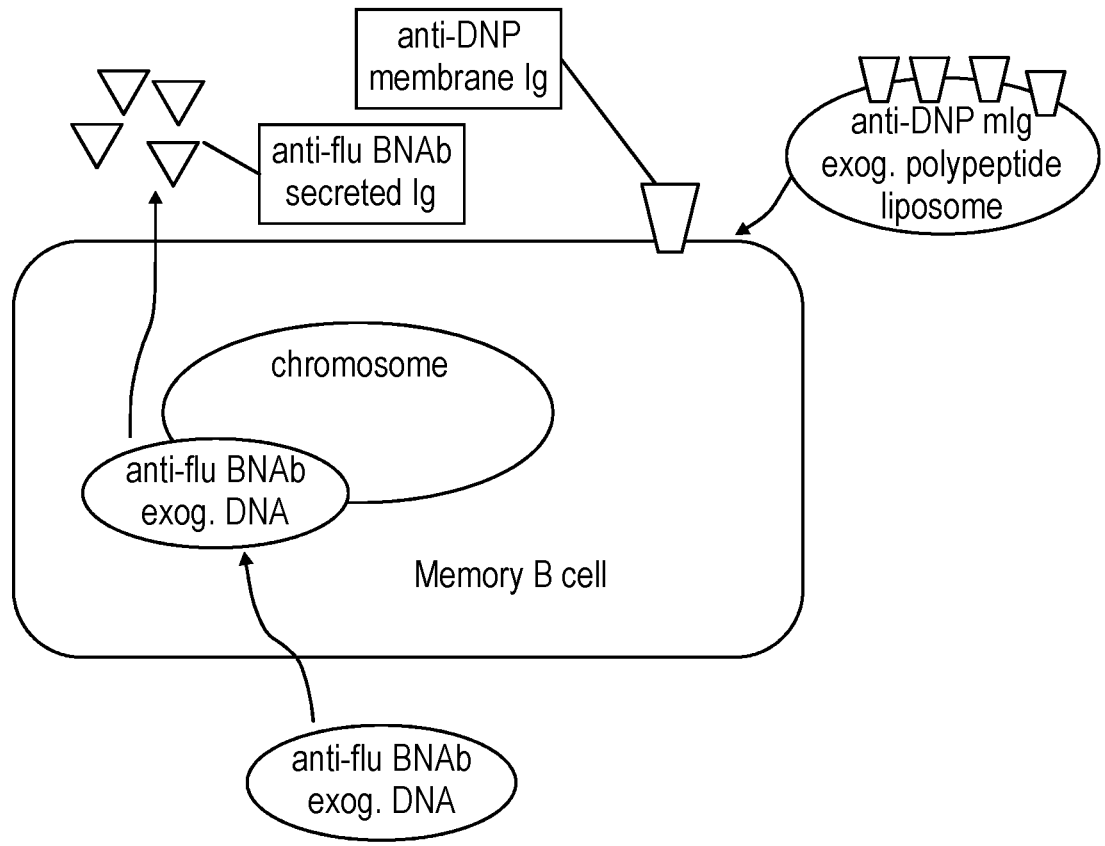
Figure 5:
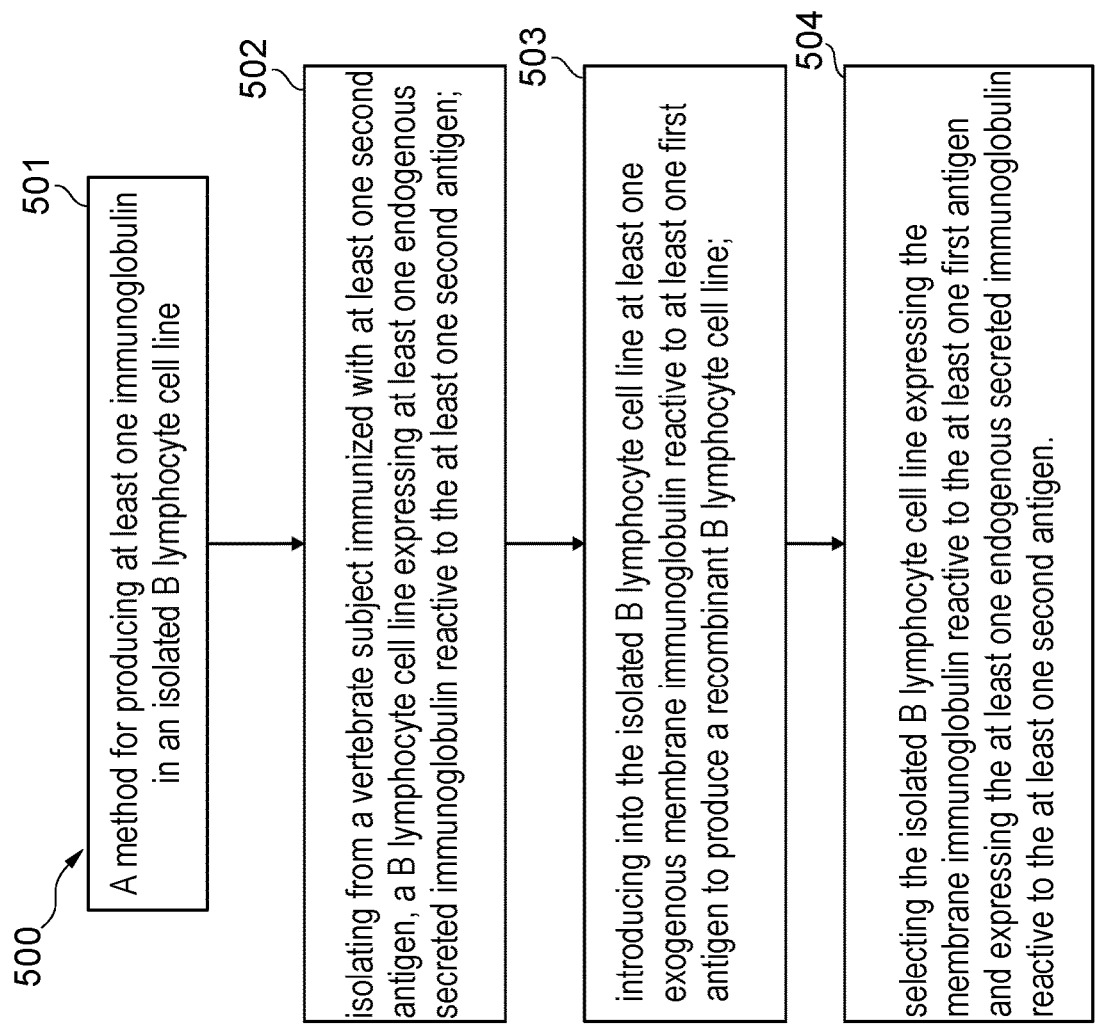
FIG. 5 is a schematic of a diagrammatic view of a method for producing an immunoglobulin in an isolated B lymphocyte cell line.
Figure 6:
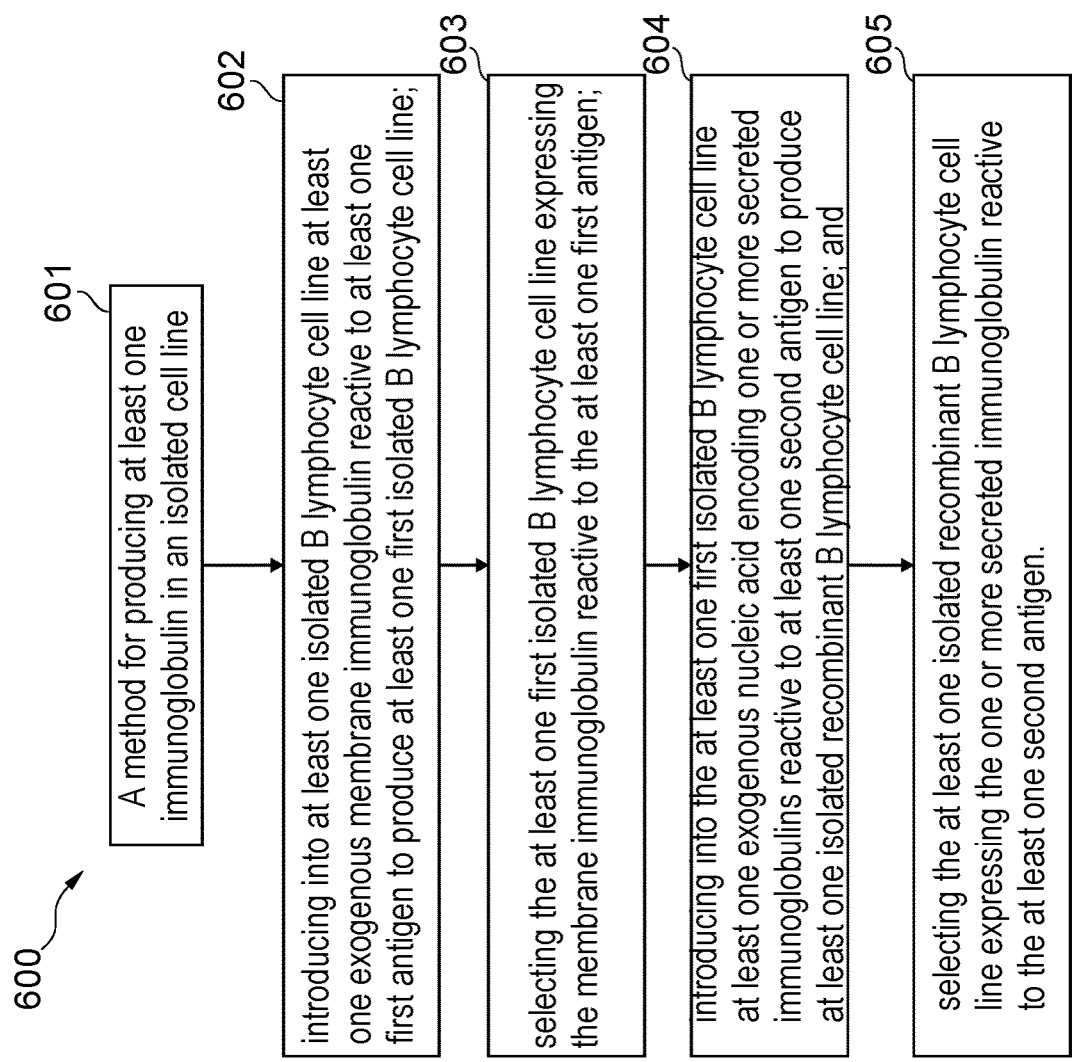
FIG. 6 is a schematic of a diagrammatic view of a method for producing an immunoglobulin in an isolated B lymphocyte cell line.
Figure 7:
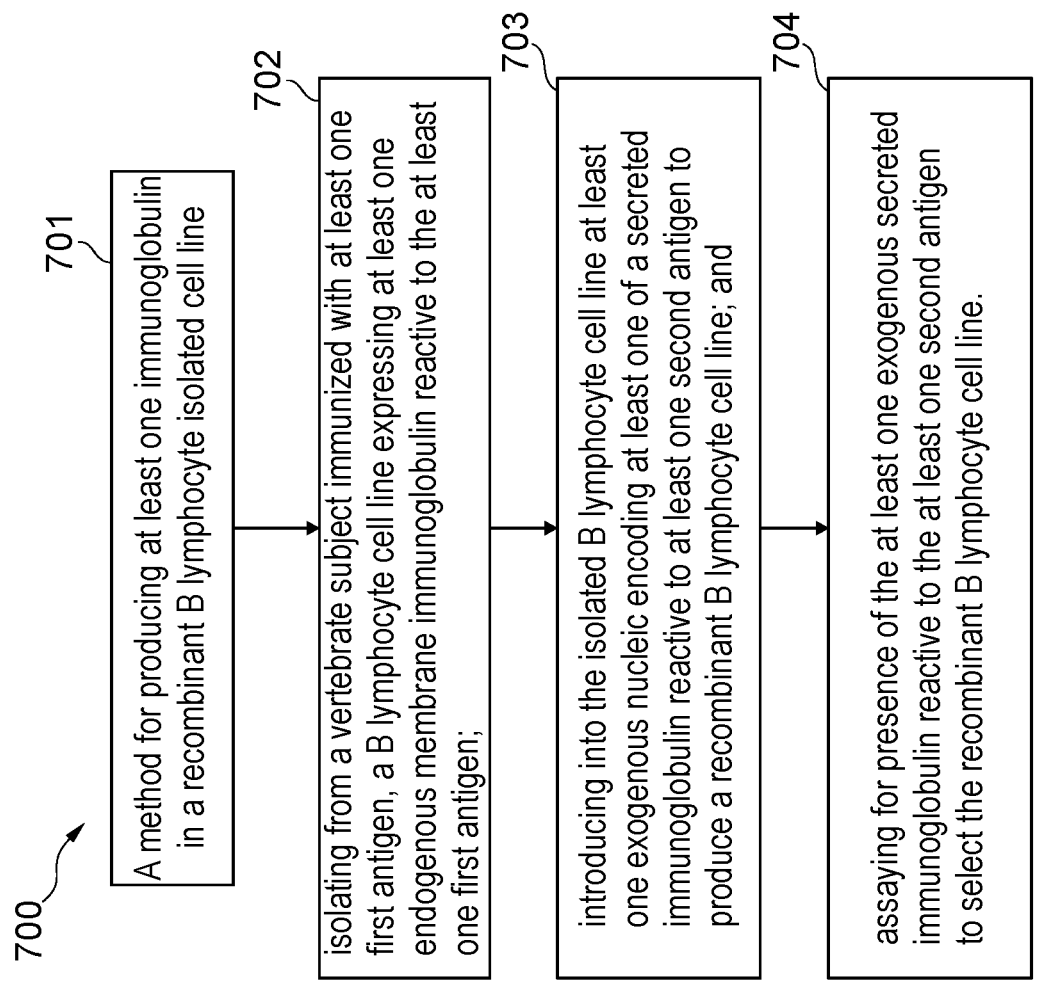
FIG. 7 is a schematic of a diagrammatic view of a method for producing an immunoglobulin in an isolated B lymphocyte cell line.

Memory B cells expressing anti-DNP membrane IgG are engineered to express Ig genes encoding a secreted IgG antibody specific for influenza. The anti-influenza IgG$_1$ H chain gene (i.e., γ$_1$-H chain gene) may be engineered to remove coding sequences for the membrane spanning domain (™), the cytoplasmic amino acids (Cyt), and a polyA addition site to yield a γ$_1$-H chain gene encoding a secreted H chain only. See FIG. 3C and Abbas et al., *Ibid*. Ig genes are engineered using standard methods in molecular biology (see e.g., Sambrook et al., In: *Molecular Cloning: A Laboratory Manual*, 2$^{nd}$ Ed., Cold Spring Harbor Press, Cold Spring Harbor, NY, 1989 which is incorporated herein by reference) to remove the membrane exons and to retain the promoter and enhancer sequences associated with the functional anti-influenza Ig genes (see e.g., Abbas et al.,

*Ibid.*). The Ig H chain and Ig L chain genes encoding the antiviral antibody may be inserted in the non-expressed Ig gene loci by using methods of homologous recombination (see e.g., U.S. Pat. No. 5,202,238 issued to Perry et al. on Apr. 13, 1993; U.S. Pat. No. 6,570,061 issued to Rajewsky and Zou on May 27, 2003 and U.S. Pat. No. 6,841,383 issued to Reff et al., on Jan. 11, 2005 which are incorporated herein by reference). Methods to identify and target DNA sequences of individual Ig gene loci in the memory B cells are known (see e.g., Suk et al., *Genome Research* published online Aug. 3, 2011. DOI/10.1101/gr.125047.111 which is incorporated herein by reference). DNA sequences determined from the nonexpressed immunoglobulin loci (i.e., nonfunctional immunoglobulin genes) are used to target recombination with the anti-influenza immunoglobulin genes.

To promote homologous recombination the Ig genes encoding the H chain and L chain for a secreted anti-influenza antibody are cloned in plasmid targeting vectors to obtain targeted integration in the corresponding nonfunctional, germline Ig loci on chromosomes 14 and 2 respectively. See FIG. 1 and FIG. 2A. For example, DNA sequences 5' of the $J_H$ segments (see FIG. 2A) are cloned upstream (5') of the anti-influenza $\gamma_1$-H chain gene in a targeting plasmid, and sequences downstream (3') of the μ-H chain membrane anchor exons are cloned downstream (3') of the $\gamma_1$-H chain gene to promote recombination at the germline H-chain locus on chromosome 14. Methods for construction of targeting vectors containing target sequences, replacement genes and selectable markers are described (see e.g., U.S. Pat. No. 5,202,238 *Ibid*., U.S. Pat. No. 6,570,061 *Ibid*., and U.S. Pat. No. 6,841,383 *Ibid*.).

Targeting vectors encoding a secreted anti-influenza antibody are used to replace the nonfunctional, germline μ-H chain gene and the nonfunctional kappa L chain gene in memory B cells expressing membrane anti-DNP IgG. The targeting vector plasmids are linearized by restriction enzyme digestion and transferred by electroporation into the memory B cells followed by selection for the targeting vector plasmids. Methods and reagents for electroporation of primary mammalian cells are described (see e.g., "Electroporation Guide" available from BioRad Inc., Hercules, CA which is incorporated herein by reference). Memory B cells, following electroporation, are cultured in tissue culture media containing selection drugs, such as G418 and methotrexate, to select for selectable marker genes, i.e., neomycin resistance gene and dihydrofolate reductase, respectively, present on the H and L chain targeting vectors. Selectable marker genes and their use are described (see e.g., U.S. Pat. No. 6,841,383 *Ibid*.). Electroporated memory B cells with resistance to both G418 and methotrexate are tested for expression of secreted IgG which binds influenza. Following transfection and selection of the memory B cells, those cells producing secreted IgG antibodies specific for influenza are identified using standard immunoassays to assess B cell supernatants (see e.g., Zhang et al., *Proc. Natl. Acad. Sci. USA* 107: 732-737, 2010 which is incorporated herein by reference).

To insure the recombinant memory B cells are safe for use in patients a suicide gene is introduced into the B cells. To stop uncontrolled proliferation (and other adverse events) by the recombinant memory B cells, a suicide gene, Herpes simplex virus-thymidine kinase gene (HSV-TK) is introduced using a retroviral expression vector. Methods to insert and express the HSV-TK gene and to activate a cytotoxic prodrug such as ganciclovir are known (see e.g., U.S. Pat. No. 6,576,464 issued to Gold and Lebkowski on Jun. 10, 2003 and U.S. Pat. No. 5,997,859 issued to Barber et al. on Dec. 7, 1999 which are incorporated herein by reference). To stop the growth of recombinant B cells deemed unsafe or contributing to an adverse event the B cells expressing HSV-TK are provided with 20 μM ganciclovir (available as Cytovene IV from Roche Laboratories, Nutley, NJ). Conversion of ganciclovir into a toxic metabolite by the B cells expressing HSV-TK results in their death. Cells not expressing HSV-TK are not harmed by ganciclovir.

The recombinant memory B cells may be activated and expanded in vitro to assess their proliferation, activation and production of the secreted anti-influenza antibody. Engineered anti-DNP memory B cells isolated as described above are cultured with DNP-HSA in vitro to activate the cells. For example, memory B cells at about $10^5$ to $10^6$ cells/mL are cultured in tissue culture flasks in standard media (e.g., RPMI 1640 serum-free media available from Sigma-Aldrich Chem. Co., St. Louis, Mo.) which contain approximately 1 μg/ml of DNP-HSA. Methods to activate memory B cells are described (see e.g., U.S. Pat. No. 7,378,276 *Ibid*.). To assess activation the cells are tested in a proliferation assay after 3-5 days in culture. Aliquots of the culture are supplemented with $^3$H-thymidine and cultured an additional 16 hours. $^3$H-thymidine uptake is measured by using a liquid scintillation counter (see e.g., U.S. Pat. No. 7,378,276 *Ibid*.). Equivalent cultures of memory B cells without DNP-HSA serve as negative controls for the proliferation assay. To assess antibody production by the activated memory B cells culture supernatants derived from 3-5 day cultures are tested by enzyme-linked immunosorbent assay (ELISA) to detect and quantitate the anti-influenza antibody. Methods to detect and quantitate anti-influenza antibodies with ELISA are described (see e.g., Khurana et al., *PLOS Med*. published online Apr. 21, 2009; doi:10.1371/journal.pmed.1000049 and Corti et al., *Science* 333: 850-856, 2011 which are incorporated herein by reference). Purified anti-influenza antibody derived from recombinant cell lines (see e.g., Wrammert et al., *Nature* 453: 667-671, 2008 which is incorporated herein by reference) may be used to create standard curves correlating absorbance and antibody concentration in ELISA assays. Supernatants from non-activated, recombinant memory B cells (i.e. cultured without DNP-HA) serve as negative control samples for the anti-influenza antibody ELISA.

The recombinant B lymphocyte cell line can be activated in vivo or ex vivo to produce the secreted broadly neutralizing influenza antibody by injecting the mammalian subject (or an in vitro cell culture) with model antigen, DNP-KLH, to activate production of the secreted antibody from the recombinant B lymphocyte cell line. Timing to stimulate immunological protection from influenza virus infection in the mammalian subject can be chosen based upon the timing of an outbreak of influenza infection in the population at large.

Example 2

Memory B Lymphocytes Engineered to Express a B Cell Receptor (BCR Recognizing Dinitrophenol (DNP) and a Secreted Antibody Recognizing Hepatitis C Virus An isolated recombinant B lymphocyte cell line that produces a secreted immunoglobulin against hepatitis C virus (HCV) and produces a membrane immunoglobulin to a model antigen can be utilized for cell therapy in a mammalian subject. The recombinant B lymphocyte cell line can be injected into the mammalian subject as adoptive cell therapy to provide immunological protection from infection by hepatitis C virus. The recombinant B lymphocyte cell line can be activated in vivo or ex vivo to produce secreted anti-HCV antibody by injecting the mammalian subject (or an in vitro cell culture) with model antigen, dinitrophenol-keyhole limpet hemocyanin (DNP-KLH). Timing to stimulate immunological protection from HCV infection in the mammalian subject can be chosen based upon the timing of exposure of the mammalian subject to HCV or based upon the appearance of symptoms in the subject.

Memory B cells expressing membrane IgG, also known as surface IgG or B cell receptor (BCR), are isolated from the peripheral blood of a patient with a chronic hepatitis C virus (HCV) infection. Polyclonal memory B cells are isolated from the patient's peripheral blood: 1) by isolating peripheral blood mononuclear cells using Ficoll Hypaque density gradients (available from Sigma Aldrich, St. Louis, MO); 2) by negative selection of total B cells using magnetic beads (available from Stem Cell Technology, Vancouver, BC), and 3) by labeling the cells with fluorescent monoclonal antibodies that recognize membrane IgG and CD27, a memory B cell marker, and performing fluorescence-activated cell sorting. See for example, U.S. Pat. No. 7,378,276 issued to Ettinger et al. on May 27, 2008 and U.S. Pat. No. 7,993,864 issued to Brown et al. on Aug. 9, 2011 which are incorporated herein by reference.

Immunoglobulin (Ig) genes encoding a membrane IgG antibody specific for DNP may be obtained from healthy volunteers who are immunized with DNP-KLH (see e.g., Biosearch Technologies: DNP-KLH Product Info Sheet which is incorporated herein by reference). Memory B cells with membrane IgG recognizing DNP are isolated by cell sorting with a fluorescence-activated cell sorter (e.g., FACSAriaIII® available from Becton Dickinson, Franklin Lakes, NJ). For example, see U.S. Pat. No. 7,378,276 Ibid. and U.S. Pat. No. 7,993,864 Ibid. Ig genes encoding an anti-DNP antibody are isolated from individual B cells (see e.g., Tiller et al., *J. Immunol. Methods* 329: 112-124, 2008 which is incorporated herein by reference). For individual anti-DNP B cells the Ig heavy (H) and corresponding Ig light (L) chain gene transcripts are amplified by reverse transcriptase-polymerase chain reaction (RT-PCR) using Superscript®III reverse transcriptase (available from Invitrogen Corp., Carlsbad, CA) and Taq DNA polymerase (available from Qiagen, Valencia, CA). Reaction conditions and oligonucleotide primers to amplify Ig H chains and Ig L chains are known (see e.g. Tiller et al., *Ibid.*). The DNA fragments encoding the Ig H and L chain variable (V) region genes are isolated and cloned in mammalian expression vectors containing Ig H and L chain constant region genes (e.g., $C\gamma_1$ and Ck). DNA sequences of the cloned anti-DNP Ig genes ($\gamma_1$-H chain and κ-L chain) are determined using a DNA sequencer (e.g., using a 3130 Genetic Analyzer available from Applied Biosystems, Carlsbad, CA). The $IgG_1$ H chain gene (i.e., $\gamma_1$-H chain gene) is engineered to remove the "tail piece" and polyadenylation site encoding the secreted form of the H chain, thus only a membrane $\gamma_1$-H chain is encoded by the engineered gene (see e.g., FIG. 3B, and Abbas et al., *Cellular and Molecular Immunology, 7th* Ed., Elsevier Saunders, Philadelphia, PA, 2012 which is incorporated herein by reference). For example, the cloned $\gamma_1$-H chain gene may be amplified by PCR with primers that amplify the $\gamma_1$-H chain constant region gene but omit the tail piece and polyadenylation site encoding the secreted form of the $\gamma_1$-H chain (see FIG. 3B). The primer may also add a RNA splice donor site to the 3' end of the $\gamma_1$-H chain gene and a unique restriction enzyme site (e.g., a site for Not I; enzyme available from New England Biolabs, Ipswich, MA). A separate DNA fragment encoding a RNA splice acceptor site, the membrane anchor exons, and the remainder of the $\gamma_1$-H chain gene are PCR-amplified using PCR primers containing restriction enzyme sites which allow reassembly of the $\gamma_1$-H gene encoding a membrane form of the $\gamma_1$-H chain. See FIG. 3B. Methods to amplify and assemble Ig genes are described (see e.g., U.S. Pat. No. 7,741,077 *Ibid.*).

Figure 2A:
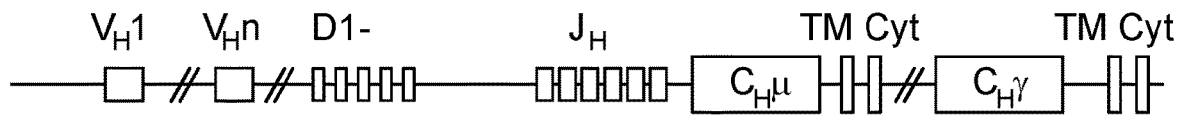
FIGS. 2A, 2B, 2C are a schematic of a diagrammatic view of nonfunctional and functional immunoglobulin heavy chain genes on chromosomes 14.

Memory B cells obtained from a patient with a chronic HCV infection are genetically engineered by replacing their functional, expressed Ig genes with Ig genes encoding a membrane IgG(κ) which recognizes DNP (see above). The Ig H and L chain genes encoding the anti-DNP antibody may be inserted in the functional, expressed Ig gene loci on chromosomes 14 and 2 by using methods of homologous recombination (see e.g., U.S. Pat. No. 5,202,238 issued to Perry et al. on Apr. 13, 1993; U.S. Pat. No. 6,570,061 issued to Rajewsky and Zou on May 27, 2003 and U.S. Pat. No. 6,841,383 issued to Reff et al., on Jan. 11, 2005 which are incorporated herein by reference). To target integration into the functional $\gamma_1$-H chain locus, targeting sequences from the intron between the $J_H$ cluster and the μ constant region gene ($C_H\mu$; see FIG. 2A) are placed 5' of the anti-DNP γ-H chain gene and sequences downstream from the γ1 membrane anchor exons are placed 3' of the γ-H chain gene (see FIG. 3A). Analogous targeting sequences (i.e., from the Jk-Ck intron and 3' of the Ck gene) are used for targeting the anti-DNP kappa L chain gene into the functional Ck gene. The targeting vectors for anti-DNP H and L chain include selectable marker genes, e.g., hygromycin resistance and histidinol dehydrogenase, respectively. Media containing hygromycin and histidinol are used to select for engineered mature B cells expressing secreted IgG anti-DNP antibody. Essential transcriptional promoter sequences and enhancer sequences necessary for Ig gene expression are retained in the Ig gene integrants (see Abbas et al., *Ibid.*). Following transfection and selection of the memory B cells, those cells producing membrane IgG antibodies specific for DNP are isolated using DNP-KLH attached to magnetic beads (protocols and separation devices are available from Miltenyi Biotec, Auburn, CA).

To create B cells producing two different antibodies the engineered memory B cells expressing an anti-DNP membrane IgG are engineered to replace their non-functional, germline Ig genes with functional Ig genes (for H and L chain). For example, the replacement Ig genes may encode a secreted antibody, an anti-HCV antibody. The Ig genes encoding an anti-viral HCV antibody may be isolated from the chromosomal DNA of a human B cell clone that produces the antiviral antibody. For example, human B cells from an individual immune to HCV are immortalized by infection with Epstein Barr virus (EBV) and supernatants derived from individual B cell clones are tested in an immunoassay for antibodies that recognize HCV. Methods to immortalize B cells and to detect anti-viral antibodies are described (see e.g., Zhang et al., *Ibid.* and Corti et al., *J. Clin. Investigation* 120: 1663-1673, 2010 which is incorporated herein by reference).

Methods may be used to clone Ig heavy (H) chain and light (L) chain genes.(see e.g., U.S. Pat. No. 7,741,077 issued to Grawunder et al. on Jun. 22, 2010 and Early et al., *Proc. Natl. Acad. Sci. USA* 76: 857-861,1979 which are incorporated herein by reference). For example, an EBV-transformed B cell line expressing a human anti-HCV antibody, IgG$_1$(kappa), is grown in culture and used as a source to isolate messenger RNA (mRNA) and genomic DNA using standard methods employing phenol/chloroform (see e.g., Sambrook et al., In: *Molecular Cloning: A Laboratory Manual*, 2$^{nd}$ Ed., Cold Spring Harbor Press, Cold Spring Harbor, N.Y., 1989). The mRNA encoding the IgG$_1$ H-chain and the kappa L-chain are molecularly cloned following amplification using the polymerase chain reaction (PCR) and reverse transcriptase (RT). Methods and Ig gene primers to amplify the H chain and L chain mRNA are described in U.S. Pat. No. 7,741,077 *Ibid*. The H and L chain mRNA (amplified as complementary DNA) are cloned in a plasmid vector (e.g., pCR®2.1-TOPO plasmid available from Invitrogen Corp., Carlsbad, CA) and the DNA sequence of the Ig H chain variable (V) region (including the Vh, D and J segments) and the kappa L chain V-region (including the Vk and Jk segments) are determined. The V-region DNA sequences may be determined by automated DNA sequencing (DNA sequencing services are available from Charles River Laboratories International, Inc., Wilmington, MA).

To isolate the corresponding genomic Ig genes, the genomic DNA isolated from the anti-HCV B cell line (see above) is used as a template for PCR amplification of the human H chain gene and kappa L chain gene. PCR primers (oligonucleotides) to amplify the V-region genes, (including their respective promoters and flanking regions upstream (i.e., 5' of the V genes) are determined by searching a human genome database with the V-region DNA sequences established from the cloned Ig mRNA. For example a human genome nucleotide database available from the National Center for Biotechnology Information can be searched with a computer program, BLAST, for sequences matching the H- and L-chain V-regions. A Human RefSeq Genome database and BLAST software are available online (see e.g., http://blast.ncbi.nlm.nih.gov/Blast.cgi). Primers to amplify the Ig constant regions, enhancer sequences, the H-chain membrane anchors, poly A addition sites and downstream flanking regions (i.e., 3' of the Ig gene) are described (see e.g., U.S. Pat. No. 7,741,077 *Ibid*.). The PCR-amplified, genomic fragments can be cloned in a plasmid vector such as pCR®2.1-TOPO available from Invitrogen Corp., Carlsbad, CA). Memory B cells expressing an anti-DNP membrane IgG antibody are engineered to express Ig genes encoding a secreted IgG antibody specific for HCV. The anti-HCV IgG H chain gene (i.e., γ-H chain gene) may be engineered to remove coding sequences for the membrane spanning domain (™); the cytoplasmic amino acids (Cyt) and a polyA addition site to yield a γ-H chain gene encoding a secreted H chain only. See FIG. 3 and Abbas et al., *Ibid*. Ig genes are engineered using standard methods in molecular biology (see e.g., Sambrook et al., In: *Molecular Cloning: A Laboratory Manual*, 2$^{nd}$ Ed., Cold Spring Harbor Press, Cold Spring Harbor, NY, 1989 which is incorporated herein by reference) to remove the membrane exons and to retain the promoter and enhancer sequences associated with the functional anti-HCV Ig genes (see e.g., Abbas et al., *Ibid*.). The Ig H and L chain genes encoding the antiviral antibody may be inserted in the non-expressed Ig gene loci by using methods of homologous recombination (see e.g., U.S. Pat. No. 5,202,238 *Ibid*., U.S. Pat. No. 6,570,061 *Ibid*. and U.S. Pat. No. 6,841,383 *Ibid*.).

To promote homologous recombination the Ig genes encoding the H chain and L chain for a secreted anti-HCV antibody are cloned in plasmid targeting vectors to obtain targeted integration in the corresponding germline Ig loci on chromosomes 14 and 2 respectively. See FIG. 1. For example, sequences 5' of the J$_H$ segments upstream from the germline μ-H chain gene (see FIG. 2: "Maternal Chromosome 14 Germline Configuration") are cloned upstream (5') of the anti-HCV γ-H chain gene in a targeting plasmid, and sequences downstream (3') of the μ-H chain membrane anchor exons are cloned downstream (3') of the γ-H chain gene to promote recombination at the germline H-chain locus on chromosome 14. Methods for construction of targeting vectors containing target sequences, replacement genes and selectable markers are described (see e.g., U.S. Pat. No. 5,202,238 *Ibid*., U.S. Pat. No. 6,570,061 *Ibid*., and U.S. Pat. No. 6,841,383 *Ibid*.).

Targeting vectors encoding a secreted anti-HCV antibody are used to replace the nonfunctional, germline μ-H chain gene and the nonfunctional kappa L chain gene in memory B cells expressing membrane anti-DNP. The targeting vector plasmids are linearized by restriction enzyme digestion and transferred by electroporation into the memory B cells followed by selection for the targeting vector plasmids. Methods and reagents for electroporation of primary mammalian cells are described (see e.g., "Electroporation Guide" available from BioRad Inc., Hercules, CA which is incorporated herein by reference). Memory B cells, following electroporation, are cultured in tissue culture media containing drugs such as G418 and methotrexate to select for selectable marker genes (i.e., neomycin resistance gene and dihydrofolate reductase, respectively) present on the H and L chain targeting vectors. Selectable marker genes and their use are described (see e.g., U.S. Pat. No. 6,841,383 *Ibid*.). Electroporated memory B cells with resistance to both G418 and methotrexate are tested for expression of secreted IgG which binds HCV. Following transfection and selection of the memory B cells, those cells producing secreted IgG antibodies specific for HCV are identified using standard immunoassays to assess B cell supernatants (see e.g., Zhang et al., *Proc. Natl. Acad. Sci. USA* 107: 732-737, 2010 which is incorporated herein by reference).

The engineered memory B cells expressing two different antibodies may be activated in vitro and assayed for proliferation and production of the secreted anti-HCV antibody. Engineered anti-DNP memory B cells are cultured in vitro with dinitrophenol-human serum albumin (DNP-HSA is available from Biosearch Technologies, Novato, CA) to activate the cells. For example, memory B cells at about 10$^5$ to 10$^6$ cells/mL are cultured at 37° C. in tissue culture flasks in standard media (e.g., RPMI 1640 serum-free media available from Sigma-Aldrich Chem. Co., St. Louis, Mo.) which contain approximately 1 μg/ml of DNP-HSA. In addition, memory B cell cultures may include 1 μg/ml of anti-CD40 antibody and 100 ng/ml of interleukin-21 (both are available from R&D Systems, Minneapolis, MN) to activate the cells and promote antibody production. Methods to activate memory B cells are described (see e.g., U.S. Pat. No. 7,378,276 *Ibid*.). To assess activation the cells are tested in a proliferation assay after 3-5 days in culture. Aliquots of the culture are supplemented with $^3$H-thymidine and cultured an additional 16 hours. $^3$H-thymidine uptake is measured by using a liquid scintillation counter (see e.g., U.S. Pat. No. 7,378,276 *Ibid*.). Equivalent cultures of memory B cells incubated without DNP-HSA serve as negative controls for the proliferation assay. To assess production of the anti-HCV antibody by the activated memory B cells, culture supernatants derived from approximately 3-5 day cultures are tested by enzyme-linked immunosorbent assay (ELISA) to detect and quantify the anti-HCV antibody. Methods to detect and quantify anti-viral antibodies with ELISA are described (see e.g., Corti et al., *Science* 333: 850-856, 2011 which is incorporated herein by reference). Virions or viral proteins are adsorbed to microtiter plates to capture anti-viral antibodies and a secondary antibody (e.g., anti-IgG) is used to detect the anti-viral antibodies. Anti-viral antibodies in the concentration range of approximately 1 ng/ml to 10,000 ng/ml may be detected using an ELISA. A purified anti-HCV antibody produced by a recombinant cell line (see e.g., Wrammert et al., Nature 453: 667-671, 2008 which is incorporated herein by reference) may be used to create standard curves for determining antibody concentration in the ELISA assay. Supernatants from engineered memory B cells that are not activated (i.e. cultured without DNP-HSA) serve as negative control samples for the anti-HCV antibody ELISA.

To insure the engineered memory B cells are safe for use in patients a suicide gene is introduced in the B cells. To stop uncontrolled proliferation (and/or other adverse events) a suicide gene, Herpes simplex virus-thymidine kinase gene (HSV-TK) is introduced into the engineered memory B cells using a retroviral expression vector. Methods to insert and express the HSV-TK gene and to activate a cytotoxic prodrug such as ganciclovir are known (see e.g., U.S. Pat. No. 6,576,464 issued to Gold and Lebkowski on Jun. 10, 2003 and U.S. Pat. No. 5,997,859 issued to Barber et al. on Dec. 7, 1999 which are incorporated herein by reference). If the engineered B cells are deemed unsafe or contributing to an adverse event the B cells expressing HSV-TK are treated with 20 µM ganciclovir (available as Cytovene IV from Roche Laboratories, Nutley, NJ). Conversion of ganciclovir into a toxic metabolite by the B cells expressing HSV-TK results in their death. Cells not expressing HSV-TK are not harmed by ganciclovir.

Engineered memory B cells expressing an anti-DNP BCR and an anti-viral (anti-HCV) secreted antibody may be expanded and used for adoptive cell therapy of the patient with chronic HCV infection. The B cells may be activated in vitro (as described above) or in vivo by administration of DNP-HSA to the patient. Immunization with approximately 100 mg DNP-KLH administered subcutaneously may be done to activate the engineered memory B cells (see e.g., Rentenaar et al., Ibid.). Multiple activations may be stimulated to respond to HCV infections.

Example 3

Mature B Lymphocytes Engineered to Express a Membrane Antibody Specific for Prostate Specific Antigen and a Second, Secreted Antibody Specific for Prostate Cancer Lipid Antigen An isolated recombinant B lymphocyte cell line that produces a secreted immunoglobulin against prostate cancer lipid antigen (PCLA) and produces a membrane immunoglobulin to prostate specific antigen (PSA) can be utilized for cell therapy to treat prostate cancer in a mammalian subject. The recombinant B lymphocyte cell line can be injected into the mammalian subject as adoptive cell therapy to provide immunological reactivity to PSA on prostate cancer cells and to process and present PSA to T lymphocytes. The recombinant B lymphocyte cell line can be activated by endogenous PSA arising in the subject to produce secreted anti-PCLA antibody. The recombinant B lymphocyte cell line can also be activated in vivo or ex vivo by injecting the mammalian subject (or an in vitro cell culture) with exogenous prostate specific antigen (PSA) to produce secreted anti-PCLA antibody. Determination of timing to stimulate immunological reactivity to prostate cancer cells in the mammalian subject can be chosen based upon the detection of prostate cancer cells in the mammalian subject.

Polyclonal mature B cells expressing B cell receptors (BCR) comprised of membrane IgM and IgD are isolated from a prostate cancer patient. Mature B cells may be obtained from peripheral blood leukocytes of the patient. For example approximately $10^9$ leukocytes may be harvested using a leukapheresis procedure (see e.g., Bensinger et al., Blood 81: 3158-3163, 1993 which is incorporated herein by reference) and approximately 5% (i.e., $5 \times 10^7$ cells) are B cells. Mature B cells are isolated from the patient's leukocytes by using antibodies specific for B cell markers CD19, IgD, CD38, and CD21 (available from Becton Dickinson/Pharmingen, San Diego, CA). Methods to purify mature B cells using magnetic beads (available from Miltenyi Biotech, Auburn, CA) and a fluorescence-activated cell sorter (FACS) are described (see e.g., U.S. Pat. No. 7,378,276 Ibid.). Mature B cells expressing membrane IgM and IgD are cultured in vitro and genetically engineered to express two different antibodies.

Mature B cells are genetically engineered to express a membrane IgG antibody specific for prostate specific antigen (PSA). PSA is a protein antigen associated with prostate cancer that may be produced using recombinant DNA methods and purified for use as an antigen (see e.g., U.S. Pat. No. 8,013,128 issued to Gudas et al. on Sep. 6, 2011 which is incorporated herein by reference). To obtain human immunoglobulin (Ig) genes encoding an antibody specific for PSA a hybridoma cell line that produces the anti-PSA antibody is constructed. For example transgenic mice with human Ig genes (e.g., XenoMouse® available from Abgenix Inc., Fremont, CA) are immunized with PSA and their B cells are fused with a myeloma cell fusion partner, e.g. SP2/0 cells (available from American Type Culture Collection, Manassas, VA) to create hybridoma cell clones expressing human antibodies (see e.g., U.S. Pat. No. 8,013,128 Ibid.). Supernatants from the hybrid clones are screened using an immunoassay to detect human IgG antibodies which bind PSA protein. Hybridoma clones producing antibodies that recognize PSA are expanded and antibodies from each clone are tested using a Biacore™ A100 instrument (available from GE Healthcare, Piscataway, NJ) to measure antibody affinity and specificity for PSA (see e.g., GE Healthcare, Application Note 84, "Early kinetic screening of hybridomas . . . ", which is incorporated herein by reference). Hybridomas expressing high affinity antibodies for PSA are selected for cloning of their human Ig genes. Methods to clone Ig heavy (H) chain and light (L) chain genes may be used. See e.g., U.S. Pat. No. 7,741,077 issued to Grawunder et al. on Jun. 22, 2010 and Early et al., Proc. Natl. Acad. Sci. USA 76: 857-861,1979 which are incorporated herein by reference. For example, a hybridoma cell line expressing a human anti-PSA antibody, $IgG_1$(kappa), is grown in culture and used as a source to isolate messenger RNA (mRNA) and genomic DNA using standard methods employing phenol/chloroform (see e.g., Sambrook et al., In: Molecular Cloning: A Laboratory Manual, $2^{nd}$ Ed., Cold Spring Harbor Press, Cold Spring Harbor, N.Y., 1989). The mRNA encoding the $IgG_1$ H-chain and the kappa L-chain are molecularly cloned following amplification using the polymerase chain reaction (PCR) and reverse transcriptase (RT). Methods and Ig gene primers to amplify the H chain and L chain mRNA are described in U.S. Pat. No. 7,741,077 Ibid. The H and L chain mRNA (amplified as complementary DNA) are cloned in a plasmid vector (e.g., pCR®2.1-TOPO plasmid available from Invitrogen Corp., Carlsbad, CA) and the DNA sequence of the Ig H chain variable (V) region (including the Vh, D and J segments) and the kappa L chain V-region (including the Vk and Jk segments) are determined. The V-region DNA sequences may be determined by automated DNA sequencing (DNA sequencing services are available from Charles River Laboratories International, Inc., Wilmington, MA). To isolate the corresponding genomic Ig genes, the genomic DNA isolated from the anti-PSA hybridoma (see above) is used as a template for PCR amplification of the human H chain gene and kappa L chain gene. PCR primers (oligonucleotides) to amplify the V-region genes, (including their respective promoters and flanking regions upstream (i.e., 5' of the V genes) are determined by searching a human genome database with the V-region DNA sequences established from the cloned Ig mRNA. For example a human genome nucleotide database available from the National Center for Biotechnology Information can be searched with a computer program, BLAST, for sequences matching the H- and L-chain V-regions. A Human RefSeq Genome database and BLAST software are available online (see e.g., the world wide web at blast.ncbi.nlm.nih.gov/Blast.cgi). Primers to amplify the Ig constant regions, enhancer sequences, the H-chain membrane anchors, poly A addition sites and downstream flanking regions (i.e., 3' of the Ig gene) are described (see e.g., U.S. Pat. No. 7,741,077 *Ibid.*). The PCR-amplified, genomic fragments can be cloned in a plasmid vector such as pCR®2.1-TOPO available from Invitrogen Corp., Carlsbad, CA). The IgG$_1$ H chain gene (i.e., $\gamma_1$-H chain gene) may be engineered to remove the "tail piece" and polyadenylation site encoding the secreted form of the H chain, thus only a membrane $\gamma_1$-H chain is encoded by the engineered gene (see e.g., FIG. 3, and Abbas et al., *Cellular and Molecular Immunology*, 7$^{th}$ Ed., Elsevier Saunders, Philadelphia, PA, 2011 which is incorporated herein by reference). For example, the cloned $\gamma_1$-H chain gene may be amplified by PCR with primers that amplify the $\gamma_1$-H chain constant region gene but omit the tail piece and polyadenylation site encoding the secreted form of the $\gamma_1$-H chain. The primer may also add a RNA splice donor site to the 3' end of the $\gamma_1$-H chain gene and a unique restriction enzyme site (e.g., a site for Not I; enzyme available from New England Biolabs, Ipswich, MA). Separate DNA fragments encoding the membrane anchor exons and the remainder of the $\gamma_1$-H chain gene are PCR-amplified using PCR primers containing restriction enzyme sites which allow reassembly of the $\gamma_1$-H gene encoding a membrane form of the $\gamma_1$-H chain. See FIG. 3. Methods to amplify and assemble Ig genes are described (see e.g., U.S. Pat. No. 7,741,077 *Ibid.*).

The Ig genes encoding the H chain and L chain for an anti-PSA membrane antibody are cloned in plasmid targeting vectors to obtain targeted integration in the corresponding nonfunctional germline Ig loci on chromosomes 14 and 2 respectively. See FIG. 1. For example, sequences 5' of the $J_H$ genes (see FIG. 2A) are cloned upstream (5') of the anti-PSA $\gamma_1$-H chain gene in a targeting plasmid, and sequences downstream (3') of the µ-H chain membrane anchor exons (TM and Cyt) are cloned downstream (3') of the $\gamma_1$-H chain gene to promote recombination at the germline H-chain locus on chromosome 14. Methods for construction of targeting vectors containing target sequences, replacement genes and selectable markers are described (see e.g., U.S. Pat. No. 5,202,238 issued to Perry et al. on Apr. 13, 1993; U.S. Pat. No. 6,570,061 issued to Rajewsky and Zou on May 27, 2003, and U.S. Pat. No. 6,841,383 issued to Reff et al. on Jan. 11, 2005 which are incorporated herein by reference). Targeting vectors constructed to replace the nonfunctional germline µ-H chain gene and the nonfunctional kappa L chain gene in mature B cells are transferred into mature B cells in vitro. The targeting vector plasmids are linearized by restriction enzyme injection and transferred by electroporation into the mature B cells followed by selection for the targeting vector plasmids. Methods and reagents for electroporation of primary mammalian cells are described (see e.g., "Electroporation Guide" available from BioRad Inc., Hercules, CA which is incorporated herein by reference). Mature B cells, following electroporation are cultured in tissue culture media containing drugs such as G418 and methotrexate to select for selectable marker genes (i.e., neomycin resistance gene and dihydrofolate reductase, respectively) present on the H and L chain targeting vectors. Selectable marker genes and their use are described (see e.g., U.S. Pat. No. 6,841,383 *Ibid.*) Electroporated mature B cells with resistance to both G418 and methotrexate are tested for expression of membrane IgG which binds PSA. For example, engineered mature B cells expressing membrane IgG specific for PSA are isolated using magnetic beads with PSA attached, and the cells are propagated in vitro prior to transfection with Ig genes for a second antibody specific for a different prostate tumor associated antigen.

Mature B cells expressing an anti-PSA membrane IgG antibody are engineered to express Ig genes encoding a secreted IgG antibody specific for prostate cancer lipid antigen (PCLA). Methods to extract PCLA and to obtain a monoclonal antibody specific for PCLA are known (see e.g., Zhang et al., *Proc. Natl. Acad. Sci.* USA 107: 732-737, 2010 which is incorporated herein by reference). A human IgG antibody specific for PCLA and the corresponding Ig genes may be obtained as described above (see e.g., U.S. Pat. No. 7,741,077 *Ibid.* and Early et al., *Ibid.*). The anti-PCLA IgG H chain gene (i.e., $\gamma$-H chain gene) may be engineered to remove coding sequences for the membrane spanning domain and the cytoplasmic amino acids to yield a $\gamma$-H chain gene encoding a secreted H chain only. See FIG. 3 and Abbas et al., *Ibid.* The anti-PCLA Ig genes are integrated into the functionally rearranged Ig gene loci of the mature B cell which include the µ-H chain gene on chromosome 14 and the kappa L chain gene on chromosome 2 (e.g., see FIG. 2; only the H chain gene is shown). Targeted integration of the anti-PCLA $\gamma$-H chain gene and L chain gene into the corresponding functional H and L chain gene loci (i.e. chromosomes 14 and 2 respectively) is done using methods of homologous recombination as described above (see U.S. Pat. No. 6,570,061 *Ibid.*, and U.S. Pat. No. 6,841,383 *Ibid.*). To target integration into the functional µ-H chain locus, targeting sequences from the intron between the $J_H$ cluster and the µ constant region gene ($C_Hµ$) are placed 5' of the anti-PCLA $\gamma$-H chain gene and sequences downstream from the µ membrane anchor exons are placed 3' of the $\gamma$-H chain gene (see FIG. 2). Analogous targeting sequences (i.e., from the Jk-Ck intron and 3' of the Ck gene) are used for targeting the anti-PCLA kappa light chain gene to the functional Ck gene. The targeting vectors for anti-PCLA H and L chain include different selectable marker genes, hygromycin resistance and histidinol dehydrogenase, respectively. Media containing hygromycin and histidinol is used to select for engineered mature B cells expressing secreted IgG anti-PCLA antibody. Essential transcriptional promoter sequences and enhancer sequences necessary for Ig gene expression are retained in the Ig gene integrants (see Abbas et al., *Ibid.*). Following transfection and selection of the mature B cells, those cells producing secreted IgG antibodies specific for PCLA are identified using standard immunoassays to assess B cell supernatants (see e.g., Zhang et al., Ibid.). The engineered mature B cells are cultured in vitro and stimulated with PSA to activate the cells and to stimulate secretion of anti-PCLA IgG antibodies.

To insure the engineered mature B cells are safe for use in patients a suicide gene is introduced in the B cells. To stop uncontrolled proliferation (and/or other adverse events) a suicide gene, Herpes simplex virus-thymidine kinase gene (HSV-TK) is introduced into the engineered memory B cells using a retroviral expression vector. Methods to insert and express the HSV-TK gene and to activate a cytotoxic prodrug such as ganciclovir are known (see e.g., U.S. Pat. No. 6,576,464 issued to Gold and Lebkowski on Jun. 10, 2003 and U.S. Pat. No. 5,997,859 issued to Barber et al. on Dec. 7, 1999 which are incorporated herein by reference). If the engineered B cells are deemed unsafe or contributing to an adverse event the B cells expressing HSV-TK are treated with 20 μM ganciclovir (available as Cytovene IV from Roche Laboratories, Nutley, NJ). Conversion of ganciclovir into a toxic metabolite by the B cells expressing HSV-TK results in their death. Cells not expressing HSV-TK are not harmed by ganciclovir.

The isolated recombinant B lymphocytes are administered to prostate cancer patients to provide antibodies to PCLA and to process and present PSA to T cells. Autologous B cells engineered to express anti-PSA membrane IgG and anti-PCLA secreted IgG are cultured in vitro with approximately 1 μg/mL PSA for approximately 3 to 5 days and then washed in serum-free media prior to injection. Approximately 5-10×10$^8$ B cells are injected intravenously and the concentration of anti-PCLA antibodies and the number of engineered B cells in the peripheral blood of the patient are monitored with immunoassays and flow cytometry respectively.

Example 4

Memory B Lymphocytes from Patients Vaccinated with Influenza Vaccine are Provided with Membrane Antibodies Specific for DNP and Activated by Administration of DNP-HSA An isolated recombinant B lymphocyte cell line that produces a secreted broadly neutralizing immunoglobulin to influenza virus and produces a membrane immunoglobulin to a model antigen can be utilized for cell therapy in a mammalian subject. The recombinant B lymphocyte cell line can be injected into the mammalian subject as cell therapy to provide immunological protection from infection by influenza virus. The recombinant B lymphocyte cell line can be activated in vivo or ex vivo to produce the broadly neutralizing influenza antibody by injecting the mammalian subject (or an in vitro cell culture) with model antigen, dinitrophenol-keyhole limpet hemocyanin (DNP-KLH). The timing to stimulate immunological protection from influenza virus infection in the mammalian subject can be chosen based upon the timing of an outbreak of influenza infection in the population at large.

An individual is immunized with an influenza vaccine to obtain memory B cells with B cell receptors (BCR) specific for influenza virus. Memory B cells develop in response to immunization with a subunit vaccine for influenza virus which may elicit broadly neutralizing antibodies (see e.g., Ekiert et al., Science 324: 246-251, 2009 which is incorporated herein by reference). A primary immunization with 1 mg of influenza virus vaccine, for example, a conserved epitope from the viral hemagglutinin (HA) protein is injected subcutaneously in the right arm. Approximately 12-14 days after immunization memory B cells expressing BCR specific for influenza are isolated using influenza HA protein-biotin and phycoerythrin (PE)-streptavidin and a fluorescein-anti-CD27 antibody to identify memory B cells (biotin, streptavidin and antibodies are available from Becton Dickinson/Pharmingen, San Diego, CA). Influenza-specific memory B cells are isolated by cell sorting with a fluorescence activated cell sorter (e.g., FACSAriaIII® available from Becton Dickinson, Franklin Lakes, NJ). For example, see U.S. Pat. No. 7,378,276 issued to Ettinger et al. on May 27, 2008 and U.S. Pat. No. 7,993,864 issued to Brown et al. on Aug. 9, 2011 which are incorporated herein by reference. Memory B cells expressing membrane IgG specific for an influenza HA epitope are cultured in vitro and expanded prior to transfection with a membrane immunoglobulin specific for dinitrophenol (DNP). For example, memory B cells at about 10$^5$ to 10$^6$ cells/mL are cultured at 37° C. in tissue culture flasks in standard media (e.g., RPMI 1640 serum-free media available from Sigma-Aldrich Chem. Co., St. Louis, Mo.) which contain approximately 1 μg/ml of influenza HA peptide (see e.g., Ekiert et al., Ibid.) In addition, memory B cell cultures may include 1 μg/ml of anti-CD40 antibody and 100 ng/ml of interleukin-21 (both are available from R&D Systems, Minneapolis, MN) to activate the cells (see e.g., U.S. Pat. No. 7,378,276 Ibid.). A membrane immunoglobulin specific for DNP is produced using recombinant DNA methods and inserted in the membrane of memory B cells producing anti-influenza antibodies. Immunoglobulin (Ig) genes encoding a membrane IgG antibody specific for DNP may be obtained from healthy volunteers who are immunized with DNP-KLH (see e.g., Biosearch Technologies DNP-KLH Product Info Sheet which is incorporated herein by reference). Memory B cells with membrane IgG recognizing DNP are isolated by cell sorting with a fluorescence-activated cell sorter (e.g., FACSAriaIII® available from Becton Dickinson, Franklin Lakes, NJ). For example, see U.S. Pat. No. 7,378,276 Ibid. and U.S. Pat. No. 7,993,864 Ibid.

Immunoglobulin genes encoding an anti-DNP antibody are isolated from individual B cells (see e.g., Tiller et al., J. Immunol. Methods 329: 112-124, 2008 which is incorporated herein by reference). For each individual anti-DNP B cell the Ig heavy (H) and corresponding Ig light (L) chain gene transcripts are amplified by reverse transcriptase-polymerase chain reaction (RT-PCR) using Superscript®III reverse transcriptase (available from Invitrogen Corp., Carlsbad, CA) and Taq DNA polymerase (available from Qiagen, Valencia, CA). Reaction conditions and oligonucleotide primers to amplify Ig H chains and Ig L chains are known (see e.g. Tiller et al., Ibid.). The DNA fragments encoding the Ig H and Ig L chain variable (V) region genes are isolated and cloned in mammalian expression vectors containing Ig H and Ig L chain constant region genes (e.g., Cγ1 and Ck). DNA sequences of the cloned anti-DNP Ig genes (γ1-H chain and κ-L chain) are determined using a DNA sequencer (e.g., using a 3130 Genetic Analyzer available from Applied Biosystems, Carlsbad, CA). The IgG, H chain gene (i.e., $\gamma_1$-H chain gene) is engineered to remove the "tail piece" and polyadenylation site encoding the secreted form of the H chain, thus only a membrane $\gamma_1$-H chain is encoded by the engineered gene (see e.g., FIG. 3B, and Abbas et al., Cellular and Molecular Immunology, 7$^{th}$ Ed., Elsevier Saunders, Philadelphia, PA, 2012 which is incorporated herein by reference). For example, the cloned $\gamma_1$-H chain gene may be amplified by PCR with primers that amplify the $\gamma_1$-H chain constant region gene but omit the tail piece and polyadenylation site encoding the secreted form of the $\gamma_1$-H chain. A separate DNA fragment encoding the $\gamma_1$ membrane anchor exons, and the remainder of the $\gamma_1$-H chain gene are PCR-amplified using PCR primers containing restriction enzyme sites which allow reassembly of the $\gamma_1$-H gene encoding a membrane form of the $\gamma_1$-H chain. See FIG. 3B. Methods to amplify and assemble Ig genes are described (see e.g., U.S. Pat. No. 7,741,077 Ibid.).

The genetically engineered immunoglobulin genes encoding the anti-DNP membrane antibody are expressed in a mammalian cell line and the membrane IgG is purified from the cell line. For example, a kappa (κ) L chain gene and the modified γ-1 H chain gene are inserted in a lentiviral expression vector using standard recombinant DNA methods (see e.g., U.S. Patent Publication No. 2007/0116690 by Yang et al. published on May 24, 2007 which is incorporated herein by reference). The viral vector is used to transfect Chinese Hamster Ovary (CHO) cells (available from American Type Culture Collection, Manassas, VA) which are engineered to express membrane immunoglobulin. Methods to express membrane immunoglobulins may be used. See e.g., Price et al., *J. Immunol. Methods* 343: 28-41, 2009 which is incorporated herein by reference. To identify and isolate CHO clones expressing the anti-DNP membrane IgG a phycoerythrin-conjugated anti-human IgG antibody was used to label CHO cells and sort them using FACS (see e.g., Price et al., *Ibid.*). A CHO cell line producing anti-DNP membrane IgG is isolated and expanded and membrane IgG is purified from CHO cell lysates using an immunoaffinity column. An affinity column constructed from protein A-Sepharose (available from Sigma-Aldrich Co., St. Louis, MO) is used to purify membrane IgG from lysates of the engineered CHO cells. For example cells may be lysed in a buffer containing: 0.15 M NaCl, 0.01 M TrisHCl, pH 8.2, 1 mM EDTA, 2 mM phenylmethylsulfonyl fluoride, 0.5% Nonidet P-40 and 1 mg/mL HSA (see e.g., Schneider et al., *J. Biol. Chem.* 257: 10766-10769, 1982 which is incorporated herein by reference). The purified anti-DNP membrane IgG is used to construct liposomes which are fused to memory B cells specific for influenza antigen (see above).

Liposomes containing anti-DNP membrane IgG are constructed from phospholipids and purified anti-DNP membrane IgG antibodies. The liposomes with incorporated anti-DNP membrane IgG antibodies may be fused with memory B cells specific for influenza virus to obtain memory B cells with anti-DNP membrane immunoglobulin incorporated into the B cell membrane. Liposomes may be prepared from cholesterol and L-α-phosphatidylcholine. See e.g., U.S. Patent Publication No. 2005/0208120, which is incorporated herein by reference. Cholesterol and L-α-phosphatidyl choline are combined at a molar ratio of 2:7 in chloroform and the chloroform is evaporated away using an argon stream. The liposomes are resuspended in a 140 mM NaCl, 10 mM Tris HCl, 0.5% deoxycholate at pH 8 and sonicated for three minutes. Purified anti-DNP membrane antibodies (see above) are inserted into the liposomes by combining the membrane IgG with liposomes at a 1:10 molar ratio and dialyzing for 72 hours at 4° C versus phosphate buffered saline. The liposomes are characterized to assess liposome size and the amount of anti-DNP membrane IgG protein incorporated into the liposomes. Liposome size is determined using dynamic light scattering and flow cytometry (see e.g., U.S. Patent Application No. 2005/0208120 by Albani which is incorporated herein by reference). For example, liposomes containing anti-DNP antibodies may have a mean diameter of approximately 50 nanometers. To measure anti-DNP IgG protein on the liposomes the liposomes are analyzed on a flow cytometer after staining with FITC-labeled anti-IgG antibody. Liposomes are sorted based on FITC fluorescence, forward scatter and side scatter to isolate and count liposomes with IgG. Anti-DNP IgG protein on the liposomes is measured using an enzyme-linked immunosorbent assay (ELISA). Methods to analyze liposomes by flow cytometry and to measure IgG and other proteins by ELISA are known (see e.g., U.S. Patent Application No. 2005/0208120, *Ibid*.).

Liposomes containing anti-DNP membrane IgG are fused with memory B cells specific for influenza virus (see above) to obtain memory B cells with anti-DNP B cell receptor. Purified liposomes with anti-DNP BCR on their surface are electrofused with the memory B cells (see e.g., Zimmermann et al., *IEEE Transactions On Plasma Science* 28: 72-82, 2000 which is incorporated herein by reference). For example a 1:1 ratio of liposomes to memory B cells are suspended in a hypo-osmolar buffer containing 0.1 mM Ca-acetate, 0.5 mM Mg-acetate and 1 mg/ml bovine serum albumin. The osmolarity is adjusted to approximately 75 mOsm and approximately 200 μL of the cell suspension containing approximately $2\times10^4$ to $2\times10^5$ cells is placed in an electrofusion chamber (electrofusion generators and chambers are available from BTX Instrument Division, Harvard Apparatus, Inc. Holliston, MA). The cells are aligned by applying an alternating field of 5 V amplitude and 2 MHz frequency for approximately 30 seconds. Then fusion is initiated by applying a rectangular fusion pulse of 20V to 40V amplitude and of 15 usec duration. The alternating field is applied again for 30 seconds to maintain cells and liposomes in position while fusion occurs. The cells are transferred to culture flasks and grown for 2 to 5 weeks.

The fused memory B cells are characterized to assess their anti-DNP BCRs and their production of anti-influenza antibodies. The fused memory B cells are tested for membrane anti-DNP antibodies using fluorescent DNP-HSA and FACS analysis. Methods to assess membrane anti-DNP IgG antibodies using flow cytometry are described above (see Example 2). The fused memory B cells may be activated in vitro to produce anti-influenza antibodies when stimulated with DNP-HSA, and the production of secreted anti-influenza virus antibodies may be measured using an ELISA based upon influenza viral hemagglutinin protein or influenza virions. Methods to measure anti-influenza antibodies and memory B cell activation are known (see e.g., U.S. Pat. No. 7,378,276 *Ibid*. and Example 1).

The human patient at risk of influenza viral infection is given recombinant fused memory B cells as a therapeutic and prophylactic cell therapy which can be activated in vivo. The recombinant memory B cells are activated in vivo by administration of DNP-HSA to the patient when an anti-influenza antibody response is needed. For example, approximately $10^8$-$10^9$ fused B cells may be injected as a prophylactic when the patient is healthy prior to "flu season." The fused memory B cells may be activated when needed by intracutaneous injection of 100 μg of DNP-HSA to the patient. For example, the fused memory B cells may be activated after the patient is exposed to influenza virus or at the first signs of infection. The production of anti-influenza antibodies may be monitored by sampling the patient's peripheral blood and performing ELISA with influenza virions as the antigen. Moreover, the presence of broadly neutralizing antibodies for multiple strains of influenza virus can be determined by ELISA based on conserved epitopes from influenza virus (see e.g., Ekiert et al., *Ibid*.)

Example 5

Construction of Autologous Memory B Lymphocytes Engineered to Produce Two Different Anti-*Staphylococcus aureus* Antibodies An isolated recombinant B lymphocyte cell line that produces two different secreted immunoglobulins to methicillin-resistant *Staphylococcus aureus* (MRSA) and produces a membrane immunoglobulin to a third *S. aureus* antigen can be utilized for cell therapy in a mammalian subject. The recombinant B lymphocyte cell line can be injected into the mammalian subject as cell therapy to provide immunological protection from infection by MRSA. The recombinant B lymphocyte cell line can be activated in vivo or ex vivo to produce antibody to MRSA by injecting the mammalian subject (or an in vitro cell culture) with *S. aureus* antigen. The timing to stimulate immunological protection from MRSA infection in the mammalian subject can be chosen based upon the exposure of the subject to MRSA or the appearance of symptoms of MRSA infection.

A patient infected with methicillin-resistant *Staphylococcus aureus* (MRSA) who has suffered recurring episodes of infection is treated with his own long-lived, memory B cells which have been genetically engineered to express two different anti-*S. Aureus* monoclonal antibodies (MAb). Memory B cells expressing membrane IgG (also known as surface IgG or B cell receptor (BCR)) are isolated from the peripheral blood of the patient with a recurrent MRSA infection. Polyclonal memory B cells with unknown antigen specificities are isolated from the patient's peripheral blood: 1) by isolating peripheral blood mononuclear cells using Ficoll Hypaque density gradients (available from Sigma Aldrich, St. Louis, MO); 2) by negative selection of total B cells using magnetic beads (available from Stem Cell Technology, Vancouver, BC), and 3) by labeling the cells with fluorescent monoclonal antibodies that recognize IgG and CD27, a memory B cell marker, and performing fluorescence-activated cell sorting. See for example, U.S. Pat. No. 7,378,276 issued to Ettinger et al. on May 27, 2008 and U.S. Pat. No. 7,993,864 issued to Brown et al. on Aug. 9, 2011 which are incorporated herein by reference. The purified memory B cells are modified using genetic engineering methods to introduce immunoglobulin (Ig) genes encoding two different anti-*S. aureus* antibodies.

Ig genes encoding a first anti-*S. aureus* IgG antibody are isolated from a hybridoma cell line which produces the antibody. Methods to construct a hybridoma cell line producing an IgG antibody specific for poly-N-acetylglucosamine (PNAG) which is protective against *S. aureus* are described (see e.g., Kelly-Quintos et al., *Infection and Immunity* 74: 2742-2750, 2006 which is incorporated herein by reference). For example transgenic mice with human Ig genes (e.g., XenoMouse® available from Abgenix Inc., Fremont, CA) are immunized with PNAG and their B cells are fused with a myeloma cell fusion partner, e.g. SP2/0 cells (available from American Type Culture Collection, Manassas, VA) to create hybridoma cell clones expressing human antibodies (see e.g., U.S. Pat. No. 8,013,128 *Ibid.*) Hybridomas expressing high affinity antibodies for PNAG are selected for cloning of their Ig genes. Methods to clone Ig heavy (H) chain and light (L) chain genes are known (see e.g., U.S. Pat. No. 7,741,077 issued to Grawunder et al. on Jun. 22, 2010 and Early et al., *Proc. Natl. Acad. Sci. USA* 76: 857-861,1979 which are incorporated herein by reference). For example, a hybridoma cell line expressing an anti-PNAG antibody, $IgG_1$ (kappa), is grown in culture and used as a source to isolate messenger RNA (mRNA) and genomic DNA using standard methods employing phenol/chloroform (see e.g., Sambrook et al., In: *Molecular Cloning: A Laboratory Manual*, $2^{nd}$ Ed., Cold Spring Harbor Press, Cold Spring Harbor, N.Y., 1989). The mRNA encoding the $IgG_1$ H-chain and the kappa L-chain are molecularly cloned following amplification using the polymerase chain reaction (PCR) and reverse transcriptase (RT). Methods and Ig gene primers to amplify the H chain and L chain mRNA are described in U.S. Pat. No. 7,741,077 *Ibid*. The H and L chain mRNA (amplified as complementary DNA) are cloned in a plasmid vector (e.g., pCR®2.1-TOPO plasmid available from Invitrogen Corp., Carlsbad, CA) and the DNA sequence of the Ig H chain variable (V) region (including the Vh, D and J segments) and the kappa L chain V-region (including the Vk and Jk segments) are determined. The V-region DNA sequences may be determined by automated DNA sequencing (DNA sequencing services are available from Charles River Laboratories International, Inc., Wilmington, MA).

To isolate the corresponding genomic Ig genes, the genomic DNA isolated from the anti-PNAG hybridoma, as isolated above, is used as a template for PCR amplification of the H chain gene and kappa L chain gene. PCR primers (oligonucleotides) to amplify the V-region genes, (including their respective promoters and flanking regions upstream (i.e., 5' of the V genes) are determined by searching a human genome database with the V-region DNA sequences established from the cloned Ig mRNA. For example a human genome nucleotide database available from the National Center for Biotechnology Information can be searched with a computer program, BLAST, for sequences matching the H- and L-chain V-regions. A Human RefSeq Genome database and BLAST software are available online (see e.g., the world wide web at blast.ncbi.nlm.nih/gov/blast.cgi). Primers to amplify the Ig constant regions, enhancer sequences, the H-chain membrane anchors, polyA addition sites and downstream flanking regions (i.e., 3' of the Ig gene) are described (see e.g., U.S. Pat. No. 7,741,077 *Ibid*.). The PCR-amplified, genomic fragments can be cloned in a plasmid vector such as pCR®2.1-TOPO available from Invitrogen Corp., Carlsbad, CA). The $IgG_1$ H chain gene (i.e., $\gamma_1$-H chain gene) may be engineered to remove the "tail piece" and polyadenylation site encoding the secreted form of the H chain, thus only a membrane $\gamma_1$-H chain is encoded by the engineered gene (see e.g., FIG. 3B, and Abbas et al., *Cellular and Molecular Immunology*, $7^{th}$ Ed., Elsevier Saunders, Philadelphia, PA, 2011 which is incorporated herein by reference). For example, the cloned $\gamma_1$-H chain gene may be amplified by PCR with primers that amplify the $\gamma_1$-H chain constant region gene but omit the tail piece and polyadenylation site encoding the secreted form of the $\gamma_1$-H chain. Separate DNA fragments encoding the membrane anchor exons and the remainder of the $\gamma_1$-H chain gene are PCR-amplified using PCR primers containing restriction enzyme sites which allow reassembly of the $\gamma_1$-H gene encoding a membrane form of the $\gamma_1$-H chain. See FIG. 3B. Methods to amplify and assemble Ig H and L chain genes are described (see e.g., U.S. Pat. No. 7,741,077 *Ibid*.).

Figure 2B:
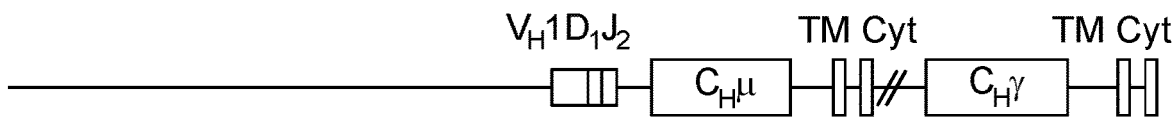
Figure 2C:
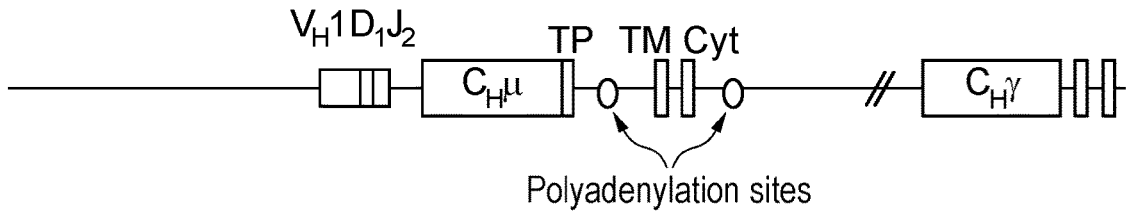

The Ig genes encoding the heavy (H) chain and light (L) chain of the anti-PNAG antibody are cloned in targeting plasmid vectors to allow targeted integration at and replacement of the corresponding functionally rearranged Ig H and Ig L chain genes on chromosomes 14 and 2 respectively (e.g., See FIG. 1). Methods to target genes to Ig loci using homologous recombination are known (see e.g., U.S. Pat. No. 5,202,238 issued to Perry et al. on Apr. 13, 1993; U.S.

Pat. No. 6,570,061 issued to Rajewsky and Zou on May 27, 2003 and U.S. Pat. No. 6,841,383 issued to Reff et al. on Jan. 11, 2005 which are incorporated herein by reference). To target integration into the functional $\gamma_1$-H chain locus, targeting sequences from the intron between the $J_H$ cluster and the $\mu$ constant region gene ($C_H\mu$; see FIG. 2A) are placed 5' of the anti-PNAG γ-H chain gene and sequences downstream from the γ1 membrane anchor exons are placed 3' of the γ-H chain gene (see FIG. 3A). Analogous targeting sequences (i.e., from the $J_K$-$C_K$ intron and 3' of the $C_k$ gene) are used for targeting the anti-PNAG kappa light chain gene into the functional $C_k$ gene. The targeting vectors for anti-PNAG H and L chain include selectable marker genes, e.g., hygromycin resistance and Zeocin™ bleomycin resistance, respectively. Media containing hygromycin B and Zeocin™ bleomycin are used to select for engineered memory B cells expressing membrane IgG anti-PNAG antibody (Protocols, selection agents and selectable markers are available from Invitrogen, Carlsbad, CA). Essential transcriptional promoter sequences and enhancer sequences necessary for Ig gene expression are retained in the Ig replacement genes (see Abbas et al., Ibid.). Following transfection, homologous recombination and selection, recombinant memory B cells expressing membrane IgG specific for S. aureus PNAG are isolated using magnetic beads with PNAG attached (magnetic beads and protocols are available from Miltenyi Biotech Inc., Auburn, CA). Memory B cells expressing the anti-PNAG membrane antibody are cultured in vitro prior to transfection with Ig genes encoding a second antibody specific for a different S. aureus antigen.

Memory B cells are produced using recombinant DNA methods to express a membrane antibody specific for PNAG and are further genetically engineered to express a second anti-S. aureus MAb. A monoclonal antibody (MAb) specific for the immunodominant staphylococcal antigen A (IsaA) is expressed in the memory B cells. To obtain an anti-IsaA MAb with prophylactic and therapeutic activity for S. aureus infections a hybridoma cell line is constructed using purified recombinant IsaA protein to immunize mice and select hybridoma clones (see e.g., Lorenz et al., *Antimicrob. Agents Chemoth.* 55: 165-173, 2011 which is incorporated herein by reference). To clone anti-IsaA antibody variable region genes messenger RNA is extracted from a selected hybridoma cell line and used as a template for complementary DNA synthesis with reverse transcriptase (RT) and amplification using polymerase chain reaction (PCR) (i.e., RT-PCR). Methods to amplify and clone the variable regions for heavy and light chain in an antibody expression vector are described (see e.g., Kelly-Quintos et al., Ibid.) For example, a plasmid expression vector encoding a complete gamma (γ)-1 H chain and a lambda (λ) L chain may be constructed using restriction enzymes and standard molecular biology methods (see e.g., Sambrook et al., Ibid.). To facilitate transfection and expression of the anti-IsaA antibody in memory B cells the $\gamma_1$-H chain gene and the λ-L chain gene may be transferred to a lentiviral vector (see e.g., U.S. Pat. No. 7,939,059 issued to Yang et al. on May 10, 2011 which is incorporated herein by reference). Infection of memory B cells with the recombinant lentivirus results in integration of the vector sequences at random sites (i.e., not targeted) in the genomic DNA of the memory B cells and production of the secreted $IgG_1$ (2) anti-IsaA antibody. Protocols and lentiviral expression vectors are available from Invitrogen Corp., Carlsbad, CA; see e.g., User Manual: "ViraPower™ HiPerfom™ Lentiviral Expression System" which is incorporated herein by reference. For example a flask of memory B cells is infected with titered recombinant lentivirus stock so as to yield a multiplicity of infection of approximately 1.0 transducing units per cell. The cells and lentivirus are incubated overnight at 37° C. in 5% $CO_2$; then, the lentivirus containing media is replaced by fresh media and incubated overnight. On the third day the cells are placed in selective media (e.g., media containing blasticidin is available from Invitrogen Corp., Carlsbad, CA) to select for stably transduced cells containing the lentiviral vector. Clones of memory B cells resistant to blasticidin are also placed under selection for hygromycin B and Zeocin™ to select clones expressing both anti-MRSA antibodies. To identify and purify memory B cells expressing both anti-S. aureus antibodies memory B cells with surface IgG specific for PNAG are purified using magnetic beads (available from Miltenyi Biotec Inc., Auburn, CA) and cultured in vitro with PNAG. Methods to obtain PNAG and culture conditions for human memory B cells are described (see e.g., Kelly-Quintos et al., Ibid. and U.S. Pat. No. 7,378,276, Ibid.). Supernatants from the cultures are tested for anti-IsaA IgG antibody with an ELISA (see e.g., Lorenz et al., Ibid.) and memory B cells producing anti-IsaA antibody are selected and expanded for adoptive immunotherapy.

The human patient at risk of MRSA infection is given recombinant memory B cells as a therapeutic and prophylactic cell therapy which can be activated in vivo. The recombinant memory B cells are activated in vivo by administration of S. aureus antigen to the patient when an anti-MRSA antibody response is needed. For example, approximately $10^8$-$10^9$ recombinant B cells may be injected as a prophylactic when the patient is healthy or has been recently infected with MRSA. The recombinant memory B cells may be activated when needed by intracutaneous injection of 100 µg of S. aureus antigen to the patient. For example, the memory B cells may be activated after the patient is exposed to MRSA or at the first signs of infection. The production of anti-MRSA antibodies may be monitored by sampling the patient's peripheral blood and performing ELISA with MRSA antigens as the target antigens.

Example 6

Adoptive Immunotherapy of a Drug-Resistant Bacterial Infection with Autologous Memory B Lymphocytes Engineered to Produce Two Different Anti-*Staphylococcus aureus* Antibodies An isolated recombinant B lymphocyte cell line that produces two different secreted immunoglobulins to methicillin-resistant *Staphylococcus aureus* (MRSA) and produces a membrane immunoglobulin to a S. aureus antigen can be utilized for cell therapy in a mammalian subject. The recombinant B lymphocyte cell line can be injected into the mammalian subject as cell therapy to provide immunological protection from infection by MRSA. The recombinant B lymphocyte cell line can be activated in vivo or ex vivo to produce antibody to MRSA by injecting the mammalian subject (or an in vitro cell culture) with S. aureus antigen. The timing to stimulate immunological protection from MRSA infection in the mammalian subject can be chosen based upon the timing of an outbreak of MRSA infection in the population at large.

To protect and treat a patient with recurrent MRSA infections the patient is given autologous recombinant B cells. The patient's memory B cells are genetically engineered to express two antibodies recognizing two S. aureus antigens: poly-N-acetyl glucosamine (PNAG) and immunodominant S. aureus antigen (IsaA). The recombinant memory B cells are activated and expanded in vitro in culture media (e.g., RPMI 1640, Sigma-Aldrich, St. Louis, MO) containing: cognate antigen, PNAG, at approximately 100 ng/mL and activating cytokines, e.g., interleukin-2 (Roche, Indianapolis, IN), interleukin-4, interleukin-21 and an anti-CD40 antibody (R&D Systems, Minneapolis, MN). After approximately 5 days of culture the memory B cells are harvested, washed and concentrated prior to infusion in the patient. Approximately $5 \times 10^8$ recombinant B cells are infused in the patient and the expansion and persistence of the recombinant B cells are followed by sampling the patient's peripheral blood. Methods to infuse and track genetically engineered lymphocytes are described (see e.g., Kalos et al., *Sci. Transl. Med.* 3, 95ra73, 2011; DOI: 10.1126/scitrans1med.3002842 which is incorporated herein by reference). For example, quantitative PCR analysis on genomic DNA obtained from the patient's whole blood may be used to determine the copy number of the anti-PNAG Ig genes and the anti-IsaA Ig genes per microgram of genomic DNA. Approximately 100-200 ng of genomic DNA is analyzed with ABI Taqman technology (available from Life Technologies Corp., Carlsbad, CA). PCR primers specific for the transfected Ig genes are validated by analysis of control genomic DNA spiked with known copy numbers of the anti-*S. aureus* Ig genes. The number of genetically engineered B cells persisting in the peripheral blood may also be assessed using flow cytometry and fluorescently labeled PNAG in combination with an anti-IgG antibody. For example, phycoerythrin (PE)-conjugated PNAG and fluorescein isothiocyanate (FITC)-conjugated anti IgG are used to stain the recombinant B cells and count them. Protocols, reagents and instrumentation for flow cytometry are available from Becton Dickinson, Franklin Lakes, NJ. In addition, the level of anti-IsaA IgG (λ) antibody in the patient's peripheral blood may be analyzed using an ELISA. The ELISA may be constructed with recombinant purified IsaA protein and anti-IgG or anti-λL-chain antibodies. Methods to construct and perform an ELISA are known (see e.g., Kelly-Quintos et al., *Ibid.*).

The recombinant memory B cells may be activated in vivo as well as in vitro to produce anti-*S. aureus* antibodies. The memory B cells may be activated in vivo by PNAG released from *S. aureus* infecting the patient or by injection of purified PNAG. Methods to purify PNAG from *S. aureus* are known (see e.g., Lorenz et al., *Ibid.*). The memory B cells are activated in vivo by binding of PNAG to their B cell receptors (BCR) and by interaction with T cells and cytokines (see e.g., Abbas et al., *Ibid.*). To enhance the activation of the recombinant memory B cells the PNAG may be administered with an immunologic adjuvant (e.g., aluminum hydroxide). Repeated activations of the memory B cells may be performed in response to recurrent MRSA infections.

The human patient at risk of MRSA infection is administered recombinant memory B cells as a therapeutic and prophylactic cell therapy which can be activated in vivo. The recombinant memory B cells are activated in vivo by administration of PNAG antigen to the patient when an anti-MRSA antibody response is needed. For example, approximately $10^8$-$10^9$ recombinant B cells may be injected as a prophylactic when the patient is healthy or has been recently infected with MRSA. The recombinant memory B cells may be activated when needed by intracutaneous injection of 100 µg of PNAG to the patient. For example, the memory B cells may be activated after the patient is exposed to MRSA or at the first signs of infection. The production of anti-MRSA antibodies may be monitored by sampling the patient's peripheral blood and performing ELISA with MRSA antigens as the target antigens. Moreover, the presence of antibodies for MRSA can be determined by ELISA based on conserved epitopes from MRSA (see e.g., Ekiert et al., *Ibid.*).

Example 7

Construction of Cytotoxic B Cells with a Recombinant B Cell Receptor

B lymphocytes produce antibodies in response to binding antigens from infectious disease microorganisms, or cancer cells, but when co-stimulated with antigens and selected cytokines they may also produce cytotoxic molecules. For example, stimulation of B cells with the cytokine, interleukin-21 (IL-21) and antigen can result in the production of cytotoxic molecules (e.g., granzyme B) which may cause cell death. Cytotoxic B cells that are useful for adoptive cell therapy are constructed by engineering a recombinant B cell receptor (BCR) which recognizes a disease associated antigen and signals to elicit expression of cytotoxic effector functions.

A recombinant B cell receptor is constructed with a single chain antibody, membrane immunoglobulin (Ig) domains, and the cytoplasmic domain of the IL-21 receptor. In this case, the single chain antibody, a single chain variable fragment (SCFv), is specific for a tumor associated antigen, prostate cancer lipid antigen (PCLA). The SCFv is linked to membrane Ig heavy chain domains including: Hinge (H), constant region 3 ($C_H3$), transmembrane (TM) and cytoplasmic (Cyto) domains which participate in signaling for B cell activation, and lastly, to the IL-21 receptor cytoplasmic domain which signals to elicit cytotoxicity functions from the B cell. See FIG. 8A. Thus, the gene transfer and expression of the recombinant B cell receptor in these engineered B cells produces modified B cells that are responsive to the antigen PCLA. Upon exposure to PCLA on cancer cells, the modified B cells produce cytotoxic effector molecules, such as granzyme B, and kill prostate cancer cells expressing PCLA.

The immunoglobulin (Ig) genes encoding an antibody that binds PCLA are isolated and engineered to construct a recombinant BCR gene for transfer and expression in a diseased subject's own B cells. PCLA, a glycolipid antigen associated with prostate cancer is obtained from prostate cancer cell lines and used as an antigen. The glycolipid antigen is used to select a single chain antibody variable fragment (SCFv) which binds PCLA. SCFv containing Ig variable region genes connected by a linker peptide have been described and can be adapted to this embodiment and methods to select antibodies from phage display single chain variable fragment (SCFv) libraries can be utilized. A SCFv protein (and the corresponding SCFv gene) which avidly binds PCLA on prostate cancer cells is selected for construction of a recombinant BCR.

The anti-PCLA SCFv gene is attached to segments encoding domains of membrane $IgG_1$ heavy (H)-chain to create a recombinant B cell receptor. The hinge segment 1008, the carboxy-terminal heavy chain constant region domain ($C_H3$) 1010, the transmembrane domain (™) 1015, and the cytoplasmic domain 1020 of membrane $IgG_1$ heavy chain are encoded at the 3' end of the SCFv 1005 gene. See FIG. 8A. Detailed methods to construct membrane IgG H-chains can be adapted to this embodiment. The $IgG_1$ transmembrane and cytoplasmic domains are a 52 amino acid segment that interacts with the associated transmembrane B cell signaling proteins, Igα and Igβ, that comprise the B cell receptor [(see e.g., Abbas et al., *Cellular and Molecular Immunology*, 7th Edition, pp. 159-161, 2012, Elsevier, Philadelphia, PA)].

The last segment of the recombinant B cell receptor contains the cytoplasmic domain of the interleukin-21 (IL-21) receptor 1025. The IL-21 receptor can signal to elicit cytotoxic effector functions in B cells. For example, co-stimulation of human B cells with an anti-Ig antibody (i.e., stimulation of membrane IgG) and IL-21 elicits expression of cytotoxic effectors such as granzyme B and perforin. The cytoplasmic domain of the IL-21 receptor protein has been identified, and the structure and signaling of the IL-21 receptor have been described. See FIG. 8A for a model of the recombinant B cell receptor protein.

DNA segments encoding the SCFv, IgG constant domains and the IL-21 receptor cytoplasmic domain are amplified from DNA clones using the polymerase chain reaction or synthesized (e.g., Custom DNA synthesis is available from Life Technologies Corp., Grand Island, NY 14072). The segment encoding the anti-PCLA SCFv may be amplified from the phage clone selected above. Immunoglobulin constant region, transmembrane domain and cytoplasmic domain sequences can be synthesized by automated DNA synthesis based on publicly available sequences, and the IL-21 receptor sequence and subdomains are available. The gene encoding the recombinant B cell receptor may be assembled from the DNA segments using the splice overlap extension method.

The recombinant B cell receptor gene is inserted in a mammalian cell expression vector for transfer into human B cells. An expression vector with cytomegalovirus (CMV) promoter elements, a selectable marker gene and poly A addition signals is described. See FIG. 8B. The plasmid vector directs expression of the recombinant B cell receptor under the control of the CMV promoter and carries a selectable marker gene to allow selection of B cells expressing the vector with a drug (e.g., Neo expression confers resistance to G418; both resistance gene, Neo, and drug, G418, are available from In VivoGen, San Diego, CA). The plasmid vector encoding the recombinant B cell receptor is transfected into primary human B cells (isolated from peripheral blood) using a device, kit and protocol available from Lonza Inc., Allendale, NJ 07401 (see e.g., Human B Cell Protocol Nucleofector® Kit, which is incorporated herein by reference). Transfected, G418-resistant B cells expressing the recombinant B cell receptor are identified by flow cytometry using antibodies specific for the SCFv present in the recombinant B cell receptor. Alternatively PCLA antigen may be used to identify B cells expressing the recombinant B cell receptor, for example, by identifying and sorting cells by flow cytometry.

B cells expressing the recombinant B cell receptor are tested in vitro for cytotoxic effector function following stimulation. Cytotoxic B cells expressing the anti-PCLA recombinant BCR are stimulated with antibodies specific for the SCFv or Ig H-chain constant region components (e.g., anti-human IgG) of the recombinant BCR, and cell culture supernatants are analyzed for the presence of Granzyme B by using an immunoassay. A Granzyme B ELIspot assay kit (available from Cell Sciences, Canton, MA) may be used to determine the number of Granzyme B producing cells in a culture. An Immunospot Analyzer and Immunospot 3 software (CTL Cellular Technology Ltd., Cleveland, OH) can be used to detect and count the Granzyme B producing modified B cells.

To determine target cell killing by the recombinant cytotoxic B cells, a flow cytometry-based assay is used to determine the percentage of target cells which are apoptotic after exposure to recombinant cytotoxic B cells. For example, approximately 250,000 recombinant cytotoxic B cells are added to 10,000 prostate cancer cells (e.g., PC3 cell line which expresses PCLA). After co-culture for approximately 3 days, target cell (i.e., PC3) apoptosis is determined by staining with annexin V and propidium iodide; the percentage of apoptotic cells is determined by flow cytometry. A matched negative control culture with a target cell line not expressing PCLA (e.g., HeLa) is compared to the PC3 culture. Also, cultures with different ratios of effector cells (recombinant cytotoxic B cells) to target cells (PC3 cells) are analyzed. For example, cultures with Effector:Target ratios of 5:1, 10:1, 25:1 and 50:1 are analyzed for target cell apoptosis and viability. A plot of target cell viability versus Effector:Target cell ratio can indicate cytotoxic effector function by the recombinant cytotoxic B cells.

Example 8

Construction of Cytotoxic B Cells with a Recombinant B Cell Receptor and Coordinate Perforin Expression Modified B cells that exhibit cytotoxicity responsive to a prostate cancer tumor antigen are engineered with a recombinant B cell receptor and an inducible gene for perforin which promote cytotoxicity for the target cells. Stimulation of B cells with the cytokine, interleukin-21 (IL-21) and antigen can result in the production of cytotoxic molecules (e.g., granzyme B) which may cause cell death. However, expression of perforin, an important cytotoxic effector molecule may be lacking in B cells. Therefore, in order to provide coordinated production of perforin, an expression cassette for perforin is placed under the control of Ig heavy chain variable region ($V_H$) promoter/enhancer sequences. Engineered cytotoxic B cells with coordinate expression of granzyme B and perforin are cytotoxic for target cells, i.e., prostate cancer cells.

A recombinant B cell receptor is constructed with a single chain antibody, membrane immunoglobulin (Ig) domains, and the cytoplasmic domain of the IL-21 receptor. The single chain antibody, a single chain variable fragment (SCFv), is specific for a tumor associated antigen, prostate cancer lipid antigen (PCLA). The SCFv is linked to membrane Ig heavy chain domains including: Hinge (H), constant region 3 ($C_H3$), transmembrane (TM) and cytoplasmic domains, which participate in signaling B cell activation, and lastly, to the IL-21 receptor cytoplasmic domain which signals to elicit cytotoxicity functions from the B cell. See FIG. 8A. Gene transfer and expression of the recombinant B cell receptor expression vector (see FIG. 8B) generates B cells that express the recombinant receptor, respond to PCLA, and produce cytotoxic effector molecules such as granzyme B. A detailed description of the recombinant B cell receptor is given in Prophetic Example 1 above.

Moreover the expression vector and transfection methods to obtain B cells expressing the recombinant B cell receptor are given (see Prophetic Example 1). Recombinant B cells respond to antigen (i.e., PCLA or tumor cells bearing PCLA on their surface) by signaling via the recombinant BCR to activate transcription at the active Ig H and L loci. For example, signaling by the recombinant BCR via interaction with Igα and Igβ may result in B cell activation and differentiation, and signaling via the IL-21 cytoplasmic domain may lead to granzyme B production. In addition, to further promote the cytotoxicity of the recombinant B cell, the human perforin gene is introduced at the active functional Ig H chain locus under the control of the Ig $V_H$ promoter and Ig enhancer elements.

Cytotoxic B cells are engineered to express the human perforin gene from the active functional Ig heavy chain locus and under the control of Ig $V_H$ promoter sequences and an Ig enhancer element. The gene encoding human perforin is publicly available. The approximately 1668 nucleotide complementary DNA (cDNA) encoding human perforin is amplified using the polymerase chain reaction (PCR) and oligonucleotide primers to add terminal sequences homologous to 5' and 3' flanking sequences of the active, rearranged Ig gamma H-chain gene in the recombinant B cell line. See FIG. 3A. For example, the perforin cDNA is amplified with a 5' primer containing approximately 30 nucleotides homologous to upstream sequence flanking the active $V_H$ gene (see e.g., $V_H 1D_1 J_2$ in FIG. 3A), and a 3' primer containing approximately 30 nucleotides homologous to sequence downstream from the active constant region gene (see e.g., $C_H \gamma$ in FIG. 3A). The amplified perforin gene with ends homologous to the active Ig H-chain gene on chromosome 14 is integrated by homologous recombination to replace the γH chain gene (see FIG. 8C). Engineering and site-specific integration of genes at the active Ig heavy chain locus in an isolated recombinant cell line are described [(see e.g., U.S. Pat. No. 9,175,072, Ibid.)]. Perforin expression by transfected B cells may be determined using an Elispot assay which enumerates perforin producing cells in vitro following stimulation of the cells. Materials and protocols for a human perforin Elispot assay are available from Cell Sciences, Inc., Canton, MA (see Data sheet: Human Perforin Elispot Kit, available online at www.cellsciences.com which is incorporated herein by reference).

To determine target cell killing by recombinant cytotoxic B cells expressing perforin, a flow cytometry-based assay is used to determine the percentage of target cells which are apoptotic after exposure to recombinant cytotoxic B cells. For example, approximately 250,000 recombinant cytotoxic B cells are added to 10,000 prostate cancer cells (e.g., PC3 cell line which expresses PCLA). After co-culture for approximately 3 days, target cell (i.e., PC3) apoptosis is determined by staining with annexin V and propidium iodide; the percentage of apoptotic cells is determined by flow cytometry. A matched negative control culture with a target cell line not expressing PCLA (e.g., HeLa) is compared to the PC3 culture. Also, cytotoxic B cells not transfected with the perforin gene are compared in the cytotoxicity assay. Cultures with different ratios of effector cells (recombinant cytotoxic B cells) to target cells (PC3 cells) are analyzed. For example, cultures with Effector:Target ratios of 5:1, 10:1, 25:1 and 50:1 are analyzed for target cell apoptosis and viability. A plot of target cell viability versus Effector:Target cell ratio can indicate cytotoxic effector function by the recombinant cytotoxic B cells.

Example 9

Engineered B Lymphocytes Express a Recombinant B-Cell Receptor Specific for Prostate Cancer Lipid Antigen and a Secreted Antibody Specific for Prostate Specific Stem Cell Antigen An isolated recombinant B lymphocyte cell line that expresses a recombinant B cell receptor (BCR) specific for prostate cancer lipid antigen (PCLA) and secretes an antibody recognizing prostate stem cell antigen (PSCA) is constructed for therapy of prostate cancer. The recombinant B lymphocyte cell line is infused in a subject to provide B cells that are not only cytotoxic for tumor cells but also produce a therapeutic antibody that recognizes prostate cancer cells. Recombinant B lymphocyte cells bind PCLA on prostate cancer cells via an engineered recombinant BCR and are activated to produce cytotoxic effectors (e.g., Granzyme B) and to secrete anti-PSCA antibody.

The recombinant B cells provide cellular and humoral immunity targeted to prostate cancer cells. The recombinant B lymphocyte cell line can also be stimulated in vivo or ex vivo by injecting the mammalian subject (or an in vitro cell culture) with exogenous PCLA to elicit cytotoxic effectors and to produce secreted anti-PSCA antibody. Determination of timing to stimulate immunological reactivity to prostate cancer cells in the mammalian subject can be chosen based upon the detection of prostate cancer cells in the mammalian subject.

Polyclonal memory B cells expressing B cell receptors (BCR) of membrane IgG are isolated from a prostate cancer patient. Polyclonal memory B cells are isolated from the patient's peripheral blood: 1) by isolating peripheral blood mononuclear cells using Ficoll Hypaque density gradients (available from Sigma Aldrich. St. Louis. Mo.); 2) by negative selection of total B cells using magnetic beads (available from Stem Cell Technology Vancouver, BC), and 3) by labeling the cells with fluorescent monoclonal antibodies that recognize membrane IgG and CD27, a memory B cell marker, and performing fluorescence-activated cell sorting. Memory B cells expressing membrane IgG are cultured in vitro and genetically engineered to express a recombinant B cell receptor and a secreted anti-PCSA antibody.

Memory B cells are genetically engineered to express a recombinant BCR specific for PCLA and a secreted IgG antibody specific for prostate stem cell antigen (PSCA). An isolated recombinant cell line is constructed that includes a recombinant BCR. The recombinant BCR binds PCLA on prostate cancer cells and signals intracellularly to the B cell to elicit expression and release of cytotoxic effector molecules such as Granzyme B as described above in Prophetic Example 6. The recombinant cell line may be selected using drug selection, e.g., G418, and flow cytometry to identify clones expressing the recombinant BCR (see e.g., Prophetic Example 6 above).

Immunoglobulin genes encoding an anti-PSCA antibody (i.e., Ig heavy chain and light chain genes) are integrated at the active, rearranged Ig heavy chain locus on chromosome 14 (see FIG. 3A), and the active, rearranged kappa light chain locus on chromosome 2, respectively. Methods and materials to obtain anti-PSCA antibodies are available. For example, to target integration of anti-PSCA antibody genes into the functional γ1-H chain locus, targeting sequences from the intron between the $J_H$ exons and the γ constant region gene ($C_H\gamma$; see FIG. 3A) are placed 5' of the anti-PSCA $\gamma_1$-H chain gene and targeting sequences selected downstream (3') from the γ1-H chain cytoplasmic exon are placed 3' of the $\gamma_1$-H chain gene (see FIG. 3A). Analogous targeting sequences (i.e., from the Jk-Ck intron and 3' of the Ck gene) are used for targeting the anti-PSCA kappa L chain gene into the functional Ck gene. The targeting vectors for anti-PSCA H and L chain include selectable marker genes, e.g., hygromycin resistance and histidinol dehydrogenase, respectively. Media containing hygromycin and histidinol are used to select for engineered memory B cells expressing the targeting vectors encoding a secreted IgG anti-PSCA antibody.

Following transfection and selection of the recombinant memory B cells, those cells producing secreted IgG antibodies specific for PSCA are identified using standard immunoassays to assess B cell supernatants. The engineered memory B cells are cultured in vitro and stimulated with PCLA to activate the cell cytotoxicity and to stimulate secretion of anti-PSCA IgG antibodies. Laboratory methods to purify PCLA, the lipid antigen, can be adapted for this embodiment. Also, isolated recombinant cell lines expressing the recombinant B cell receptor and anti-PSCA antibodies are tested in a cytotoxicity assay with target cells expressing PCLA and PSCA. For example, PC3, a prostate tumor cell line bearing PCLA can be transduced with a vector encoding PSCA and tested in vitro in cytotoxicity assays with engineered cytotoxic B cell lines. Methods and materials for transducing PC3 cells are described, and details of the cytotoxicity assay are described above. See Prophetic Example 6.

Example 10

Construction of Cytotoxic B Cells for Prostate Cancer by Transfection of B Cells with Transcription Factors Cytotoxic B cells are produced by engineering memory B cells expressing B cell receptors (BCR) specific for prostate cancer lipid antigen (PCLA). The B cells are transfected with a viral vector encoding transcription factors which control the expression of cytotoxic effector molecules including granzyme B and perforin. Engineered cytotoxic B cells that recognize and kill prostate cancer cells can be used for adoptive cell therapy in prostate cancer patients.

Memory B cells expressing B cell receptors recognizing PCLA are constructed with immunoglobulin (Ig) genes encoding an anti-PCLA antibody. The engineered Ig genes are inserted at the actively transcribed heavy (H) and light (L) chain loci on human chromosomes 14 and 2. Polyclonal memory B cells expressing B cell receptors (BCR) of membrane IgG are isolated from a prostate cancer patient. Polyclonal memory B cells are isolated from the patient's peripheral blood: 1) by isolating peripheral blood mononuclear cells using Ficoll Hypaque density gradients (available from Sigma Aldrich. St. Louis. Mo.); 2) by negative selection of total B cells using magnetic beads (available from Stem Cell Technology Vancouver, BC), and 3) by labeling the cells with fluorescent monoclonal antibodies that recognize membrane IgG and CD27, a memory B cell marker, and performing fluorescence-activated cell sorting. Memory B cells expressing membrane IgG are cultured in vitro and genetically engineered to express a B cell receptor specific for PCLA.

Immunoglobulin genes encoding an anti-PCLA antibody (i.e., Ig heavy chain and light chain genes) are integrated at the active, rearranged Ig heavy chain locus on chromosome 14 (see FIG. 3A), and the active, rearranged kappa light chain locus on chromosome 2, respectively. Anti-PCLA antibodies are obtained, and the corresponding Ig genes are isolated, engineered and site-specifically integrated at the active Ig heavy chain and light chain loci in an isolated recombinant cell line. For example, to target integration of anti-PCLA membrane Ig H-chain gene into the functional, rearranged γ-H chain locus: Targeting sequences upstream (5') from the variable region exon (VH1D1J2; see FIG. 3A) and downstream (3') from the gamma-H chain constant region exon (CHγ; see FIG. 3A) are placed 5' and 3' respectively, of the engineered, membrane γ-H chain gene (see FIG. 3B). Analogous targeting sequences (i.e., from 5' of VkJk exon and 3' of the Ck gene) are used for targeting the anti-PCLA kappa L chain gene into the functional Ck gene on Chromosome 2.

Engineered B cells expressing membrane IgG specific for PCLA are transduced with a viral vector encoding three transcription factors essential for cytotoxic B cell function. Three transcription factors regulate the expression of cytotoxic effector molecules such as granzyme B. Transcription factors: T-bet, Runx3 and Eomes are essential for the expression of granzyme B and perforin in the context of cytotoxic T cell differentiation. A tricistronic vector encoding T-bet, Runx3 and Eomes is constructed using a Sendai virus vector which transduces human B cells. See FIG. 8D. Transfection and expression of the vector in the engineered B cells can be monitored by immunostaining with antibody-enzyme conjugates specific for T-bet, Runx3 and Eomes (e.g., anti-Eomes, anti-T-bet and anti-Runx3 antibodies are available from Abcam, Cambridge, MA), and expression of Granzyme B and perforin can be detected by reverse transcriptase-polymerase chain reaction (RT-PCR) of RNA from the transfected cells.

Engineered cytotoxic B cells expressing membrane IgG specific for PCLA are tested for cytotoxic effector function versus prostate cancer cell lines. For example, PC3, a prostate tumor cell line bearing PCLA can be used as a target cell in a flow cytometric assay that detects apoptotic cells following exposure to the engineered cytotoxic B cells (see Prophetic Example 2 above).

Engineered cytotoxic B cells expressing membrane IgG recognizing PCLA can also be tested in vivo in a xenogeneic mouse model of human prostate cancer. For example, PC3, human prostate tumor cells are implanted subcutaneously in immunodeficient mice (e.g., NSG mice available from Jackson Labs, Bar Harbor, ME) and the mice are treated with the engineered cytotoxic B cells. The mice are evaluated with respect to tumor size, body weight and survival. Control tumor cell lines can include tumors not expressing PCLA. Moreover, the survival or expansion of cytotoxic B cells in the mice following infusion or injection in control mice or PC3 tumor-bearing mice is evaluated and recorded.

Example 11

Modified Memory B Lymphocytes to Treat Prostate Cancer

Memory B lymphocytes are isolated from a prostate cancer patient and engineered to express an anti-PCLA (prostate cancer lipid antigen) membrane Ab (antibody) and a chemokine receptor, CXCR3. A gene encoding a single chain anti-PCLA Ab is integrated at the active, rearranged kappa light (L)-chain locus on chromosome 2, and disrupts endogenous Ig kappa L-chain expression. The CXCR3 gene is integrated at the endogenous active, rearranged immunoglobulin (Ig) heavy (H)-chain locus and disrupts endogenous Ig H-chain expression. Engineered B cells that home to prostate cancer tumors by virtue of CXCR3-mediated chemotaxis (see e.g., Sackstein et al., *Laboratory Investigation* 97: 669-697, 2017 which is incorporated herein by reference) are used for adoptive cell therapy of prostate cancer. Tumor-localized, engineered B cells provide therapeutic anti-PCLA antibodies to tumor cells at elevated local concentrations.

Memory B cells are engineered to express a single chain membrane Ab for PCLA (prostate cancer lipid antigen) under the control of the endogenous Ig kappa promoter and/or enhancer sequences by insertion in the endogenous rearranged, active kappa light chain gene locus using CRISPR technology (Clustered Regularly Interspaced Short Palindromic Repeats). The immunoglobulin (Ig) genes encoding an antibody that binds PCLA are isolated and engineered to construct a recombinant Ig gene for transfer and expression in a diseased subject's own B cells. PCLA, a glycolipid antigen associated with prostate cancer is obtained from prostate cancer cell lines and used as an antigen. The glycolipid antigen is used to select a single chain antibody variable fragment (SCFv) which binds PCLA. SCFv containing Ig variable region genes connected by a linker peptide have been described and can be adapted to this embodiment.

Methods to select antibodies from phage display single chain variable fragment (SCFv) libraries can be utilized. A SCFv protein (and the corresponding SCFv gene) which avidly binds PCLA on prostate cancer cells is selected for construction of a recombinant single chain Ab. The anti-PCLA SCFv is connected to a $\gamma_1$-H chain constant region gene that encodes the transmembrane and cytoplasmic domains of the $\gamma_1$-H chain. The anti-PCLA single chain Ab gene is incorporated in an AAV vector (Adeno-Associated Virus vector) and is flanked by homology arms for integration at the kappa L-chain locus on chromosome 2 (see e.g., Eyquem et al., Nature 543, 113-117, 2017 which is incorporated herein by reference). Homology arms that target the active endogenous Ig kappa-chain gene flank the anti-PCLA Ab gene to direct integration into the kappa L-chain locus and disrupt endogenous kappa L-chain expression. See FIG. 9A for more details.

Synthetic RNAs encoding a guide RNA targeting the integration site and a messenger RNA encoding Cas9 endonuclease are introduced by electroporation into memory B cells. Approximately 2 hours later the cells are transduced with the AAV-PCLA Ab vector. (Synthetic guide RNAs and Cas9 mRNA are available from Trilink Biotechnologies, San Diego, CA, and AAV vectors are available from Cell Biolabs, Inc., San Diego, CA).

Memory B cells are engineered to also express a gene for CXCR3 at the active Ig H-chain locus on chromosome 14. Simultaneous integration of the anti-PCLA Ab and CXCR3 genes using CRISPR technology can be performed to expedite and optimize engineering of memory B cells (see e.g., Le Cong et al., Science 339: 819-823, 2013 which is incorporated herein by reference). A gene encoding CXCR3 is available from GenScript, Piscataway, NJ. Site-specific integration of the CXCR3 gene at the active H-chain locus is accomplished using CRISPR technology (see e.g., Eyquem et al., Nature 543: 113-117, 2017 which is incorporated herein by reference). An adenovirus-associated viral (AAV) vector is designed to encode the human CXCR3 gene flanked by homology arms targeting the Ig H-chain CH1 exon on Chromosome 14, in order to disrupt the active Ig H-chain gene and insert a functional CXCR3 gene. See FIG. 9B for more details.

Synthetic RNAs encoding guide RNAs targeting the integration site and a messenger RNA encoding Cas9 endonuclease are introduced by electroporation into memory B cells isolated from the prostate cancer patient. Approximately 2 hours later the cells are transduced with the AAV-CXCR3 vector. (Synthetic guide RNAs and Cas9 mRNA are available from Trilink Biotechnologies, San Diego, CA, and AAV vectors are available from Cell Biolabs, Inc., San Diego, CA). Genetically engineered B cells are grown in vitro using culture media containing cytokines such as IL-21 and co-stimulators such as oligodeoxynucleotide, CpG and anti-CD40 Ab (see e.g., Kwakkenbos et al., Nature Medicine 16: 123-128, 2010 which is incorporated herein by reference).

B cells expressing CXCR3 from the disrupted Ig H-chain locus are identified and isolated using flow cytometry. B cells that stain with fluorescent anti-CXCR3 Ab and are not stained by fluorescent anti-IgM antibody are selected by cell sorting and cultured in vitro. Fluorescent anti-CXCR3 and anti-human IgM Abs are available from ABCAM, Cambridge, MA. B cells staining positive with CXCR3 Ab are tested in vitro for expression of CXCR3 mRNA using RT-PCR; B cells negative for CXCR3 and/or positive for IgM are tested as negative controls. Each B cell sample is tested plus and minus stimulation with B cell activators (e.g., IL-21, anti-CD40 and CpG).

To evaluate biological function of the CXCR3 gene in engineered B cells, an in vitro chemotaxis assay is performed with CXCL10, a ligand for CXCR3. Engineered B cells are introduced onto a permeable membrane in a transwell plate. The chamber below the membrane is filled with culture medium containing CXCL10 and following incubation for several hours the migration of engineered B cells to the lower chamber is scored by staining the B cells in situ. Control plates omit CXCL10, or use non-transfected B cells or IgM-positive B cells. Methods and materials to perform the chemotaxis assay are described (see e.g., Conley-LaComb et al., Ibid. and Xia et al., Oncotarget 7: 60461-474, 2016 which are incorporated herein by reference).

The recombinant memory B cells are activated and expanded in vitro in culture media (e.g., RPMI 1640, Sigma-Aldrich, St. Louis, MO) containing: cognate antigen, PCLA, at approximately 100 ng/mL and activating cytokines, e.g., interleukin-2 (Roche, Indianapolis, IN), interleukin-4, interleukin-21 and an anti-CD40 antibody (R&D Systems, Minneapolis, MN).

After approximately 5 days of culture the memory B cells are harvested, washed and concentrated prior to infusion in the patient. Approximately $5 \times 10^8$ recombinant B cells are infused and the expansion and persistence of the recombinant B cells are followed by sampling the patient's peripheral blood. Methods to infuse and track genetically engineered lymphocytes are described (see e.g., Kalos et al., Sci. Transl. Med. 3, 95ra73, 2011; DOI: 10.1126/scitranslmed.3002842 which is incorporated herein by reference).

Example 12

Construction of Engineered Memory B Lymphocytes to Modulate Autoimmunity

Memory B lymphocytes obtained from a patient with multiple sclerosis (MS) are engineered to express a membrane antibody (Ab) that recognizes myelin oligodendrocyte glycoprotein (MOG), and to produce an anti-inflammatory cytokine, interleukin 10 (IL-10). The engineered B cells bind MOG and respond by producing IL-10. A gene for an anti-MOG membrane Ab is expressed under the control of a constitutive promoter, and a gene encoding IL-10 is integrated at the endogenous Ig heavy (H)-chain locus of memory B cells and expressed under the control of the endogenous rearranged immunoglobulin variable heavy ($V_H$) promoter and/or enhancer elements.

A gene encoding IL-10 is inserted at the endogenous active Ig H-chain locus on chromosome 14 using CRISPR technology. For example a complementary DNA (cDNA) encoding human IL-10 (available from Harvard Medical School, Boston, MA) is incorporated in an adenovirus associated virus (AAV) vector (e.g., AAV vectors are available from Cell Biolabs, Inc., San Diego, CA). The human IL-10 cDNA is flanked by a splice acceptor (SA) sequence, a poly A addition site (pA) and homology arms (HA) to target recombination at the Ig H-chain locus on Chromosome 14. See FIG. 12A for more details.

A guide RNA targeting the $C_H\mu1$ exon of the μ H-chain gene results in a double-stranded DNA break that disrupts μ H-chain expression and promotes insertion of the IL-10 gene. See FIG. 12A for more details.

Methods to construct guide RNAs for targeted insertion are described (see e.g., Eyquem et al., Ibid. and Zheng et al., BioTechniques 57:115-124, 2014 which is incorporated herein by reference), and synthetic guide RNAs and Cas9 mRNA are available from Trilink Biotechnologies, San Diego, CA. Memory B cells expressing membrane IgM are obtained and purified from the peripheral blood of a MS patient. Memory B cells are obtained by cell sorting using anti-IgM and anti-CD27 antibodies. For example, see Tangye et al., J. Immunology 179, 13-19, 2007 which is incorporated herein by reference). Methods and materials for electroporation and viral transduction of lymphocytes are described (see e.g., Eyquem et al., Ibid.). Memory B cells that lack membrane IgM on their surface are tested for their production of IL-10. Membrane IgM negative, IL-10 positive B cells are expanded and activated prior to lentivirus transduction.

A lentiviral vector is constructed to direct expression of an anti-MOG membrane Ab on memory B cells. For example, a single chain, membrane Ab gene may be constructed with a gene encoding a human single chain variable fragment (SCFv) specific for MOG (obtained from a SCFv phage library). The SCFv gene is joined to a human Ig γ 1 constant region gene which includes: the hinge region, $C_H1$-$C_H3$, the transmembrane domain (TM) and the cytoplasmic tail (Cyto) (see e.g., Xu et al., Cell Research 24, 651-654, 2014 which is incorporated herein by reference). See FIG. 12B.

The anti-MOG membrane Ig gene is preceded by a constitutive promoter, (e.g., the human cytomegalovirus promoter (CMV) and cloned in a lentiviral vector suitable for transduction of B lymphocytes (see e.g., Bovia et al., Blood 101, 1727-1733, 2003 which is incorporated herein by reference). Methods and reagents to activate and transduce human B lymphocytes are described (Bovia et al., Ibid.). B lymphocytes expressing membrane IgG are detected and purified using anti-human IgG antibodies (available from ABCAM Inc., Cambridge, MA) and flow cytometry.

Engineered B cells expressing a membrane IgG specific for MOG are tested in vitro to assess functionality. For example, the engineered B cells are grown with media containing MOG glycoprotein to activate their membrane IgG receptors and media samples are collected and assayed for IL-10. Control cultures containing human serum albumin, or no additional protein are also tested. Positive control cultures containing anti-human IgG are also tested for IL-10 concentration. Standard enzyme-linked immunosorbent assays for IL-10 and recombinant human MOG protein are available from R&D Systems, Inc., Minneapolis, MN. Initial in vitro cultures to demonstrate the functionality of the engineered B cells establish the dose-response curve to MOG protein and the kinetics of IL-10 production. Such dosages can be adapted for animal studies and clinical trials in human subjects.

Example 13

Construction of Cytotoxic B Cells to Treat HIV

Genes encoding a recombinant B cell receptor (BCR) and interleukin 21 (IL-21) are inserted at the immunoglobulin (Ig) heavy (H)-chain locus in memory B cells to disrupt the endogenous, active gamma (γ) H-chain gene and to engage the Ig variable region (VH) promoter and H-chain enhancer elements. Genomic targeting with CRISPR/Cas9 technology, including specific guide RNAs restricts DNA DS breaks and gene insertion to the rearranged γ H-chain gene expressed by each IgG-positive memory B cell.

A bicistronic gene composed of a recombinant BCR gene and a gene for IL-21 are inserted in the rearranged, active γ H-chain gene on chromosome 14 in IgG-positive memory B cells. Polyclonal memory B cells expressing membrane IgG are isolated from the peripheral blood of a patient using magnetic bead separations and flow cytometry to isolate IgG-positive, CD27-positive, B cells (see e.g., Ettinger et al., Ibid. and Brown et al., Ibid.). Targeted disruption and integration at multiple different active Ig γ H-chain genes is accomplished using a CRISPR/Cas9 system with two guide RNAs and a template gene for homologous recombination. Methods and materials to delete a DNA segment and replace it with donor gene(s) of interest are described (see e.g., Zheng et al., BioTechniques 57, 115-124, 2014 which is incorporated herein by reference). For example, guide RNAs (gRNAs) targeting two conserved sites in each rearranged γ H-chain gene are designed to target: (1) a site in VDJ-Cγ intron which is downstream (3') of the Ig mu enhancer (μEnh) but upstream (5') of the class switch recombination site (CSRS); and (2) a site near the first exon (CHγ1) of the γ constant region gene. See FIG. 13 for more details.

The design of guide RNAs and selection of target sites to give optimal specificity and efficient deletion of genomic segments is described (see e.g., Zheng et al., Ibid.).

An AAV vector containing a bicistronic DNA construct encoding a recombinant BCR and IL-21 is constructed with homology arms that flank the deletion in the γ 1-H chain gene. See FIG. 13 for more details.

A P2a peptide is encoded 5' of the BCR and the IL-21 genes. Bicistronic constructs with P2a self-cleaving peptides are described (see e.g., Kim et al., PLOS ONE 6(4): e18556, 2011; doi:10.1371/journal.pone.0018556 which is incorporated herein by reference). The recombinant BCR may be constructed from a broadly neutralizing Ab for HIV (see e.g., Balazs et al., Nature 481, 81-84, 2012 which is incorporated herein by reference) and expressed as a single chain variable fragment (SCFV).

The engineered memory B cells are incubated with HIV envelope protein and media samples are collected at 1, 2, 4, and 8 hours and the amount of IL-21 is determined using an immunoassay (e.g., enzyme-linked immunosorbent assay, (ELISA)). An IL-21 ELISA kit is available from RayBiotech, Inc., Norcross, GA. Negative control cultures without HIV env protein or with a control protein, (e.g., human serum albumin) are compared to the HIV env-stimulated cultures. Positive control cultures are run using anti-IgG antibodies to stimulate the engineered B cells.

Engineered memory B cells are tested for cytotoxic effector function in vitro using engineered mammalian cells expressing HIV env protein. A mammalian cell line, e.g., HEK 293 is transfected with an expression vector encoding HIV-1 gp41 (gp41 cDNA is available from Bioclone Inc., San Diego, CA) and a cell line (gp41/HEK) expressing gp41 on the cell surface is selected using an anti-gp41 monoclonal antibody, Mab. Co-culture of engineered memory B cells with gp41/HEK target cells is followed by monitoring cell viability, e.g., Trypan Blue staining, assessing apoptosis and measuring release lactic dehydrogenase. Moreover, the release of Granzyme B into the media can be measured using an ELISA. The cellular cytotoxicity measured against gp41/HEK cells versus control HEK 293 cells is obtained at various ratios of cytotoxic B cell effectors to target cells (e.g., 1:1, 2:1, 4:1, 10:1, 20:1, 40:1).

Each recited range includes all combinations and sub-combinations of ranges, as well as specific numerals contained therein.

All publications and patent applications cited in this specification are herein incorporated by reference to the extent not inconsistent with the description herein and for all purposes as if each individual publication or patent application were specifically and individually indicated to be incorporated by reference for all purposes.

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having ordinary skill in the art will recognize that there are various vehicles by which processes and/or systems and/or other technologies disclosed herein can be effected (e.g., hardware, software, and/or firmware), and that the preferred vehicle will vary with the context in which the processes and/or systems and/or other technologies are deployed. For example, if a surgeon determines that speed and accuracy are paramount, the surgeon may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies disclosed herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those having ordinary skill in the art will recognize that optical aspects of implementations will typically employ optically-oriented hardware, software, and or firmware.

In a general sense the various aspects disclosed herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices disclosed herein, or a microdigital processing unit configured by a computer program which at least partially carries out processes and/or devices disclosed herein), electrical circuitry forming a memory device (e.g., forms of random access memory), and/or electrical circuitry forming a communications device (e.g., a modem, communications switch, or optical-electrical equipment). The subject matter disclosed herein may be implemented in an analog or digital fashion or some combination thereof.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

The herein described components (e.g., steps), devices, and objects and the description accompanying them are used as examples for the sake of conceptual clarity and that various configuration modifications using the disclosure provided herein are within the skill of those in the art. Consequently, as used herein, the specific examples set forth and the accompanying description are intended to be representative of their more general classes. In general, use of any specific example herein is also intended to be representative of its class, and the non-inclusion of such specific components (e.g., steps), devices, and objects herein should not be taken as indicating that limitation is desired.

With respect to the use of substantially any plural or singular terms herein, the reader can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A modified B cell of expressing:
   at least one exogenously incorporated membrane immunoglobulin or a recombinant receptor that at least does one of binding to a first antigen and is stimulated by a first antigen;
   at least one exogenously incorporated reassigned biological agent, and
   at least one endogenous secreted immunoglobulin reactive to a second antigen.

2. The modified B cell of claim 1, wherein the at least one exogenously incorporated membrane immunoglobulin includes at least one exogenously incorporated nucleic acid encoding the at least one exogenous membrane immunoglobulin.

3. The modified B cell of claim 2, wherein the exogenously incorporated nucleic acid encoding the at least one membrane immunoglobulin is integrated in one or more chromosomal loci in the isolated B lymphocyte cell line.

4. The modified B cell of claim 3, wherein the chromosomal loci include at least one of the Ig H chain or Ig L chain chromosomal loci located on the non-expressed Ig allele.

5. The isolated modified B cell of claim 3, wherein integration of at least one exogenous nucleic acid encoding the exogenous membrane immunoglobulin includes disruption of expression of the B cell endogenous immunoglobulin.

6. The modified B cell of claim 3, wherein the at least one exogenously incorporated membrane immunoglobulin or a recombinant receptor that at least does one of binding to the first antigen and is stimulated by a first antigen and effects the production of the at least one endogenous secreted immunoglobulin reactive to the second antigen.

7. The modified B cell of claim 1, wherein the at least one exogenously incorporated membrane immunoglobulin includes at least two exogenously incorporated nucleic acids encoding the at least one exogenous membrane immunoglobulin.

8. The modified B cell of claim 1, wherein the at least one exogenously incorporated membrane immunoglobulin includes nucleic acids encoding one heavy chain (H) immunoglobulin and one light chain (L) immunoglobulin.

9. A modified B cell that is modified for expressing:
- at least one exogenously incorporated membrane immunoglobulin or recombinant receptor that that one of least binds to a first antigen and is stimulated by a first antigen;
- at least one exogenously incorporated reassigned biological agent; and
- at least one exogenously incorporated nucleic acid encoding secreted immunoglobulin that at least does one of binding to a second antigen and is stimulated by a second antigen.

10. The isolated modified B cell of claim 9, wherein the exogenously incorporated nucleic acid encoding the at least one membrane immunoglobulin is integrated in one or more chromosomal loci in the isolated modified B cell.

11. The modified B cell of claim 10, wherein the chromosomal loci include at least one of the Ig H chain or Ig L chain chromosomal loci.

12. The isolated modified B cell of claim 11, wherein integration of at least one exogenous nucleic acid encoding the exogenous membrane immunoglobulin includes disruption of expression of the B cell endogenous immunoglobulin.

13. The modified B cell of claim 9, wherein the at least one exogenously incorporated membrane immunoglobulin includes at least two exogenously incorporated nucleic acids encoding the at least one exogenous membrane immunoglobulin.

14. The modified B cell of claim 13, wherein the at least one exogenously incorporated membrane immunoglobulin includes nucleic acids encoding two heavy chain (H) immunoglobulins and two light chain (L) immunoglobulins.

15. The modified B cell of claim 9, wherein the at least one exogenously incorporated membrane immunoglobulin includes nucleic acids encoding one heavy chain (H) immunoglobulin and one light chain (L) immunoglobulin.

16. The modified B cell of claim 9, wherein the modified B cell is included in a polyclonal population of B lymphocytes.

17. The modified B cell of claim 9, wherein the modified B cell is included in a monoclonal population of B lymphocytes.

18. The modified B cell of claim 9, wherein the exogenously incorporated nucleic acid encoding secreted immunoglobulin is encoded by an exogenously incorporated nucleic acid integrated into at least one chromosomal loci in the modified B cell including one or more non-Ig L or non-Ig H chromosomal loci.

19. The modified B cell of claim 18, the exogenously incorporated nucleic acid is within a chromosomal locus of the B cell endogenous immunoglobulin H-chain and/or L-chain.

20. A modified B cell capable of for expressing at least one exogenously incorporated membrane immunoglobulin or a recombinant receptor that is reactive to a first antigen;
- and at least one endogenous secreted immunoglobulin reactive to a second antigen;
- at least one exogenously incorporated reassigned biological agent;
- and at least one exogenously incorporated membrane receptor configured to directly or indirectly induce expression of at least one cytotoxic effector molecule.

21. The modified B cell of claim 20, wherein the membrane receptor configured to directly or indirectly induce at least one cytotoxic effector molecule includes at least one chimeric receptor exhibiting at least a portion of at least one cytokine receptor.

22. An modified B cell for expressing at least one exogenously incorporated membrane immunoglobulin or a recombinant receptor that is reactive to a first antigen;
- and at least one exogenous secreted immunoglobulin reactive to a second antigen;
- at least one exogenously incorporated reassigned biological agent;
- and at least one exogenously incorporated membrane receptor configured to directly or indirectly induce expression of at least one cytotoxic effector molecule.

23. The modified B cell of claim 22, wherein the membrane receptor configured to directly or indirectly induce at least one cytotoxic effector molecule includes at least one chimeric receptor exhibiting at least a portion of at least one cytokine receptor.

* * * * *